United States Patent
Rettig et al.

(10) Patent No.: US 12,162,818 B2
(45) Date of Patent: *Dec. 10, 2024

(54) INHIBITORS OF THE N-TERMINAL DOMAIN OF THE ANDROGEN RECEPTOR

(71) Applicants: The Regents of the University of California, Oakland, CA (US); The United States Government represented by the Department of Veterans Affairs, Washington, DC (US)

(72) Inventors: Matthew Rettig, Los Angeles, CA (US); Michael E. Jung, Los Angeles, CA (US); D. Elshan Nakath G. Ralalage, Los Angeles, CA (US); Jiabin An, Los Angeles, CA (US)

(73) Assignees: The Regents of the University of California, Oakland, CA (US); The United States Government represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,027

(22) Filed: Jan. 13, 2022

(65) Prior Publication Data
US 2022/0380298 A1   Dec. 1, 2022

Related U.S. Application Data

(63) Continuation of application No. 16/478,914, filed as application No. PCT/US2018/014516 on Jan. 19, 2018, now Pat. No. 11,261,152.

(60) Provisional application No. 62/562,217, filed on Sep. 22, 2017, provisional application No. 62/448,729, filed on Jan. 20, 2017.

(51) Int. Cl.
| | |
|---|---|
| C07C 225/16 | (2006.01) |
| A61P 35/00 | (2006.01) |
| C07C 33/48 | (2006.01) |
| C07C 49/223 | (2006.01) |
| C07C 235/34 | (2006.01) |
| C07C 235/78 | (2006.01) |
| C07C 321/20 | (2006.01) |
| C07D 207/08 | (2006.01) |
| C07D 211/32 | (2006.01) |
| C07D 241/04 | (2006.01) |
| C07D 265/30 | (2006.01) |
| C07D 303/32 | (2006.01) |
| C07D 303/40 | (2006.01) |
| C07D 307/52 | (2006.01) |
| C07D 333/24 | (2006.01) |

(52) U.S. Cl.
CPC ............ *C07C 225/16* (2013.01); *A61P 35/00* (2018.01); *C07C 33/486* (2013.01); *C07C 49/223* (2013.01); *C07C 235/34* (2013.01); *C07C 235/78* (2013.01); *C07C 321/20* (2013.01); *C07D 207/08* (2013.01); *C07D 211/32* (2013.01); *C07D 241/04* (2013.01); *C07D 265/30* (2013.01); *C07D 303/32* (2013.01); *C07D 303/40* (2013.01); *C07D 307/52* (2013.01); *C07D 333/24* (2013.01)

(58) Field of Classification Search
CPC .................................................. C07C 225/16
See application file for complete search history.

(56) References Cited

U.S. PATENT DOCUMENTS

| | | | |
|---|---|---|---|
| 3,050,520 | A | 8/1962 | Erner et al. |
| 3,739,015 | A | 6/1973 | Hashimoto et al. |
| 3,956,374 | A | 5/1976 | Shepard et al. |
| 4,013,643 | A | 3/1977 | Nysted |
| 8,034,974 | B2 | 10/2011 | Sibi et al. |
| 11,261,152 | B2 | 3/2022 | Rettig et al. |
| 2002/0161262 | A1 | 10/2002 | Sattlegger et al. |
| 2011/0218342 | A1 | 9/2011 | Sibi et al. |

(Continued)

FOREIGN PATENT DOCUMENTS

| | | |
|---|---|---|
| CH | 581152 A5 | 10/1976 |
| CN | 101076336 A | 11/2007 |

(Continued)

OTHER PUBLICATIONS

RN 103593-12-0 in STN Registry (1986).*

(Continued)

*Primary Examiner* — Brian E McDowell

(74) *Attorney, Agent, or Firm* — Foley Hoag LLP; David P. Halstead

(57) ABSTRACT

The present disclosure provides compounds of Formula (VIIb) and methods for inhibiting or degrading the N-terminal domain of the androgen receptor, as well as methods for treating cancers such as prostate cancer.

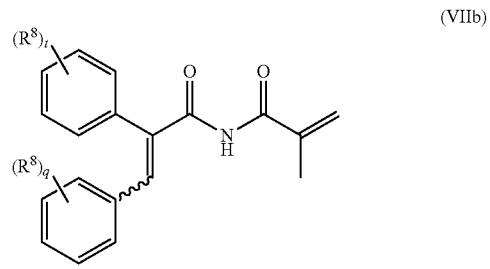

(VIIb)

15 Claims, 11 Drawing Sheets

(56) References Cited

U.S. PATENT DOCUMENTS

| | | | |
|---|---|---|---|
| 2013/0336962 | A1 | 12/2013 | Andersen et al. |
| 2019/0382335 | A1 | 12/2019 | Rettig et al. |
| 2022/0177418 | A1 | 6/2022 | Rettig et al. |

FOREIGN PATENT DOCUMENTS

| | | |
|---|---|---|
| CN | 103764604 A | 4/2014 |
| CN | 104610272 A | 5/2015 |
| CN | 104788381 A | 7/2015 |
| DE | 2334507 A1 | 1/1974 |
| EP | 0134578 A2 | 3/1985 |
| GB | 693128 A | 6/1953 |
| JP | H03216625 A | 9/1991 |
| WO | WO-95/00486 A1 | 1/1995 |
| WO | WO-96/25405 A1 | 8/1996 |
| WO | WO-01/05743 A1 | 1/2001 |
| WO | WO-01/98250 A1 | 12/2001 |
| WO | WO-2002/50007 A2 | 6/2002 |
| WO | WO-2006/044379 A2 | 4/2006 |
| WO | WO-2009/158257 A2 | 12/2009 |
| WO | WO-2012/103457 A2 | 8/2012 |
| WO | WO-2012/117421 A1 | 9/2012 |
| WO | WO-2013/005049 A1 | 1/2013 |
| WO | WO-2015/166042 A1 | 11/2015 |
| WO | WO-2018/136792 A1 | 7/2018 |
| WO | WO-2020/205470 A1 | 10/2020 |

OTHER PUBLICATIONS

Aggarwal et al., "Catalytic Asymmetric Nazarov Reactions Promoted by Chiral Lewis Acid Complexes" Org Lett, 5(26): 5075-5078 (2003).
Babu et al., "Acetyl analogs of combretastatin A-4: synthesis and biological studies" Bioorganic and Medicinal Chemistry, 19(7):2359-2367 (2011).
Cunha et al., "On the Reactivity of ?-(Triphenylphosphoranylidene)-benzylphenylketene with Nitrogen Compounds. Synthetic and Mechanistic Implications" J. Braz. Chem. Soc, 13(5): 687-691 (2002).
Gazvoda et al., "2,3-Diarylpropenoic acids as selective non-steroidal inhibitors of type-5 17 ?-hydroxysteroid dehydrogenase (AKR1C3)" European Journal of Medicinal Chemistry, 62: 89-97 (2013).
Gilchrist et al., "Ring-opening of 2,5-diaryl-3-lithiofurans" Journal of the Chemical Society—Perkin Transactions 1, 9:989-993 (1976).
Hu et al., "Nickel-Catalyzed Decarbonylative Borylation of Amides: Evidence for Acyl C—N Bond Activation" Angewandte Chemie, 55:8718-8722 (2016).
Kumar et al., "Synthesis of combretastatin analogs: evaluation of in vitro anticancer activity and molecular docking studies" Medicinal Chemistry Research, 21 :3720-3729 (2012).
CAS Registry No. 1327786-45-7 (2011).
CAS Registry No. 1348090-61-8 (2011).
CAS Registry No. 1349044-98-9 (2011).
CAS Registry No. 1349440-40-9 (2011).
CAS Registry No. 2209369-99-1 (2018).
Chavda et al., "On the Synthesis and Anticancer Testing of α, β-Unsaturated Ketones as Analogs of Combretastatin-A4," Lett Drug Des Discov, 6(7): 531-537 (2009).
Codington et al., "Reactions with α-Acetyl-4'-Chlorostilbene," J Org Chem, 17(7): 1023-1026 (1952).
Database Registry (STN) RN 1135191-33-1, [online], Apr. 16, 2009, [Retrieved on Sep. 7, 2021].
Database Registry (STN) RN 199788-52-8, [online], Jan. 15, 1998, [Retrieved on Sep. 7, 2021].
Database Registry (STN) RN 801161-95-5, [online], Dec. 22, 2004, [Retrieved on Sep. 7, 2021].
Database Registry (STN) RN 904250-43-7, [online], Aug. 24, 2006, [Retrieved on Sep. 7, 2021].
Database Registry (STN) RN 906726-80-5, [online], Sep. 15, 2006, [Retrieved on Sep. 7, 2021].
Dimmock et al., "Anticonvulsant properties of some Mannich bases of conjugated arylidene ketones," Journal of Pharmaceutical Sciences, 81(5): 436-440 (1992).
Elshan et al., "Molecules targeting the androgen receptor (AR) signaling axis beyond the AR-ligand binding domain," Medicinal Research Reviews, 39(3): 910-960 (2018).
Elshan et al., "Synthesis of beta-Amino Diaryldienones using the Mannich reaction," Organic Letters, 21(11): 4039-4043 (2019).
Extended European Search Report for EP Application No. 18742116.9 dated Sep. 18, 2020.
Fine et al., "Reexamination of the claisen-schmidt condensation of phenylacetone with aromatic aldehydes," The Journal of Organic Chemistry, 38(9): 1747-1749 (1973).
Gupta et al., "Intramolecular Dehydrogenative Coupling of 2, 3-Diaryl Acrylic Compounds: Access to Substituted Phenanthrenes," The Journal of Organic Chemistry, 81(13): 5663-5669 (2016).
International Preliminary Report on Patentability for International Application No. PCT/US2018/014516 issued Jul. 23, 2019.
International Search Report and Written Opinion for International Application No. PCT/US2018/014516 dated May 7, 2018.
International Search Report and Written Opinion for International Application No. PCT/US2020/025120 dated Jun. 24, 2020.
Karki et al., "Synthesis and biological evaluation of some stilbene derivatives," Medicinal Chemistry Research, 20(8): 1349-1356 (2010).
Karpaviciene et al., "Synthesis and antiproliferative activity of α-branched α, β-unsaturated ketones in human hematological and solid cancer cell lines," Eur J Med Chem, 98: 30-48 (2015).
Katritzky et al., "Preparation of N-(alpha,bata-unsaturated acyl)-sulfonamides," Arkivoc, iv(4): 115-124 (2009).
Lesieur et al., "Versatile relay and cooperative palladium(0) N-heterocyclic carbene/copper(I) N-heterocyclic carbene catalysis for the synthesis of tri- and tetrasubstituted alkenes," ChemCatChem, 7(14): 2108-2112 (2015).
Lipshutz et al., "Metalation studies of trisubstituted oxazoles," J Org Chem, 46(7): 1410-1413 (1981).
RN 741607-32-9 Registry ED Entered STN: Sep. 8, 2004.
RN 782399-84-2 Registry ED Entered STN: Nov. 16, 2004.
RN 857340-47-7 Registry ED Entered STN: Jul. 28, 2005.
RN 929709-48-8 Registry ED Entered STN: Apr. 11, 2007.
Siwapinyoyos et al., "Novel route to alpha-methylene cyclopentenones. High-yield synthesis of methylenomycin B," The Journal of Organic Chemsitry, 47(3): 598-599 (1982).
Steinhuebel et al., "Asymmetric hydrogenation of protected allylic amines," Organic Letters, 12(18): 4201-4203 (2010).
Stoddart et al., "A Novel Structural Framework for α1A/D-Adrenoceptor Selective Antagonists Identified Using Subtype Selective Pharmacophores," PLoS One, 6(5): e19695 (2011).
Streicher et al., "Stilbene induced inhibition of androgen receptor dimerization: implications for AR and AR delta LBD-signalling in human prostate cancer cells," PLoS One, 9(6): e98566 (2014).
Topolovcan et al., "Synthesis of 1, 2-Disubstituted Cyclopentadienes from Alkynes Using a Catalytic Haloallylation/Cross-Coupling/Metathesis Relay," Organic Letters, 18(15): 3634-3637 (2016).
Walter et al., "Stilbene-Based Inhibitors of Estrone Sulfatase with a Dual Mode of Action in Human Breast Cancer Cells," Arch Pharm, 337(12): 634-644 (2004).
Wang et al., "Alkyl bromides as mild hydride sources in Ni-catalyzed hydroamidation of alkynes with isocyanates," J Am Chem Soc, 138(48): 15531-15534 (2016).
Wei et al., "Practical metal-free synthesis of chalcone derivatives via a tandem cross-dehydrogenative-coupling/elimination reaction," Green Chemistry, 15(11): 3165-3169 (2013).
Xue et al., "Ambient arylmagnesiation of alkynes catalysed by ligandless nickel (ii)," Chem Comm, 49(86): 10121-10123 (2013).
Yasmin et al., "A simple one-pot synthesis of 2-Aryl-5-alkyl-substituted oxazoles by Cs2CO3-mediated reactions of aromatic primary amides with 2,3-Dibromopropene," Synlett, 17: 2825-2827 (2009).
Zhang et al., "A New Chalcone Derivative (E)-3-(4-Methoxyphenyl)-2-methyl-1-(3,4,5-trimethoxyphenyl)prop-2-en-1-one Suppresses Prostate Cancer Involving p53-mediated Cell Cycle Arrests and Apoptosis," Anticancer Research, 2012, vol. 32, p. 3689-3698.

(56) References Cited

OTHER PUBLICATIONS

Zinc408907509, PubChem CID: 12514387; PubChem SID: 332263147 (2017).

Žvak et al., "Nucleophilic substitution reaction of keto-allylic systems with a heterocyclic ring in γ-position," Collect Czech Chem Commun, 49(8): 1764-1773 (1984).

International Search Report and Written Opinion for Application No. PCT/US2024/015756 dated Jun. 13, 2024.

Pubchem CID 135254864, Create Date: Dec. 15, 2018. [retrieved on Dec. 15, 2018.]. Retrieved from the Internet. <URL: https://pubchem.ncbi.nlm.nih.gov/compound/135254864>.

* cited by examiner

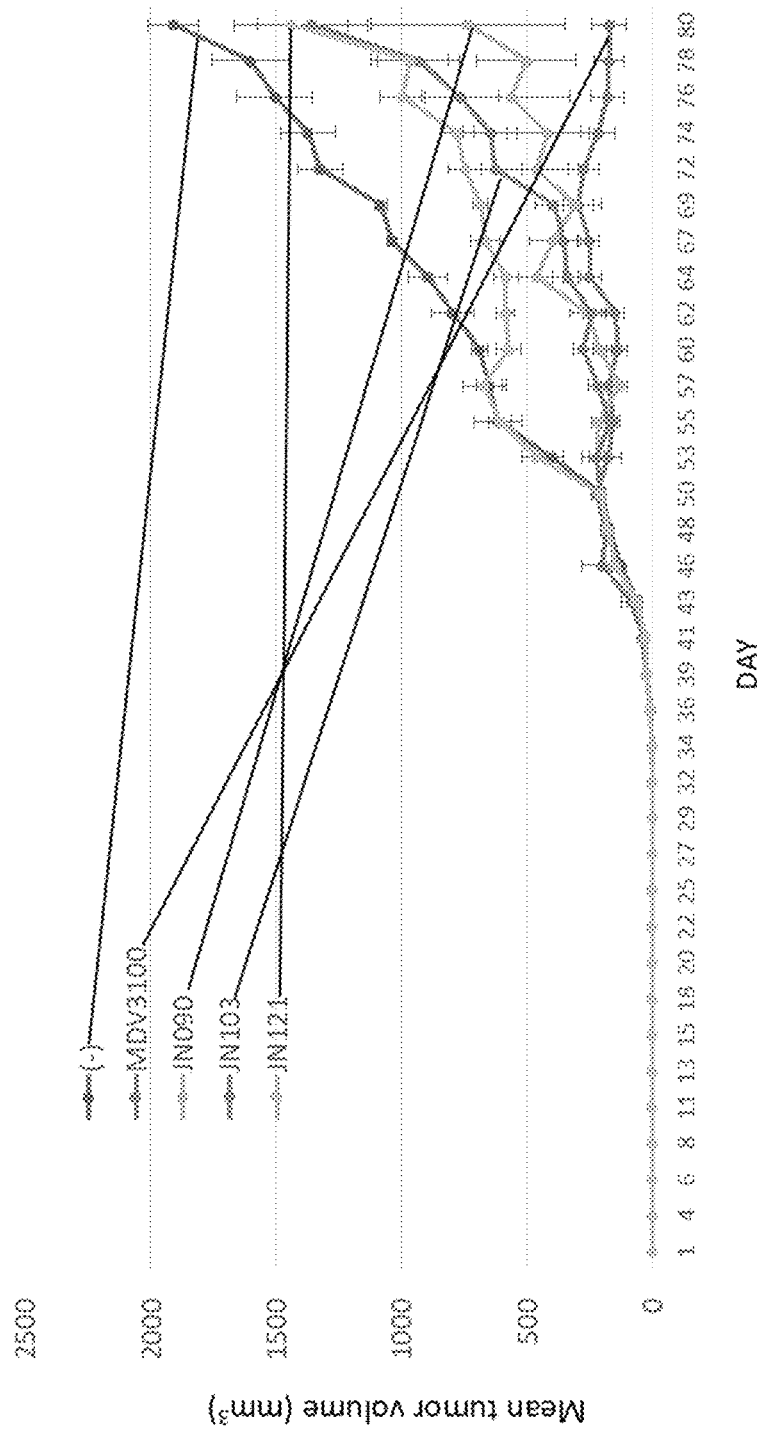

INHIBITORS OF THE N-TERMINAL DOMAIN OF THE ANDROGEN RECEPTOR

RELATED APPLICATIONS

This application is a continuation of U.S. patent application Ser. No. 16/478,914, filed Jul. 18, 2019, which is a U.S. National Stage Application of International Application No. PCT/US18/14516, filed on Jan. 19, 2018, which claims the benefit of U.S. Provisional Patent Application No. 62/448,729, filed on Jan. 20, 2017, and U.S. Provisional Patent Application No. 62/562,217, filed on Sep. 22, 2017. The contents of each of these applications is incorporated herein incorporated by reference in its entirety.

STATEMENT REGARDING FEDERALLY SPONSORED RESEARCH

This invention was made with government support under CA164331, and CA092131 awarded by the National Institutes of Health.The government has certain rights in the invention. This work was supported by the U.S. Department of Veterans Affairs, and the Federal government has certain rights in the invention.

BACKGROUND OF THE INVENTION

Prostate cancer is the most common cancer and the second leading cause of cancer death in Western men. When the cancer is confined locally, the disease can usually be treated by surgery or radiation. However, 30% of prostate cancers treated that way relapse with distant metastatic disease, and some patients have advanced disease at diagnosis. Advanced disease is treated by castration and/or administration of antiandrogens, the so-called androgen deprivation therapy. Castration lowers the circulating levels of androgens and reduces the activity of androgen receptor (AR). Administration of antiandrogens blocks AR function by competing away androgen binding, thereby reducing the AR activity. Although initially effective, these treatments quickly fail and the cancer becomes hormone refractory, or castration resistant.

Castration resistant prostate cancer (CRPC) is typified by persistent expression and transcriptional activity of the androgen receptor (AR). Over the last decade, pre-clinical models, correlative studies involving patient material, and clinical studies have provided the evidence to support the notion that inhibiting the AR represents a viable approach to effectively treat CRPC. Accordingly, improved inhibitors of the AR are needed.

SUMMARY OF THE INVENTION

In certain aspects, the present invention provides compounds having the structure of formula I, II, III, IV, V, V, VII, VIII, or a pharmaceutically acceptable salt thereof:

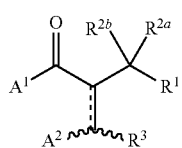
(I)

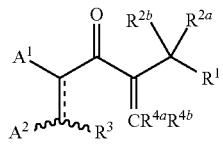
(II)

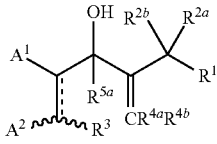
(III)

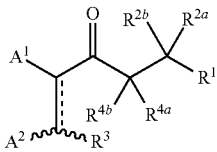
(IV)

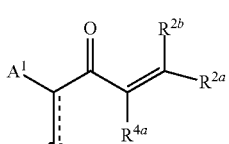
(V)

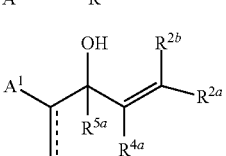
(VI)

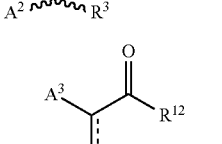
(VII)

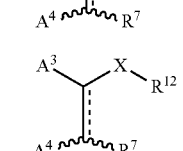
(VIII)

wherein:
 represents a single or double bond;
$A^1$ is aryl or heteroaryl;
$A^2$ is aryl or heteroaryl;
$A^3$ is aryl or heteroaryl;
$A^4$ is aryl or heteroaryl;
$R^1$ is selected from H, $N(R^{1a}R^{1b})$, N-linked heterocyclyl, or N-linked heteroaryl;
$R^{1a}$ and $R^{1b}$ are independently selected from alkyl, aryl, and aralkyl;
$R^{2a}$ and $R^{2b}$ are independently selected from H, alkyl, or aryl;
$R^3$ is selected from H, alkyl, or halo;
$R^{4a}$ and $R^{4b}$ are independently selected from H, alkyl, or halo;
$R^{5a}$ is selected from H, alkyl, or halo;
$R^{12}$ is hydroxyl, alkyl, alkenyl, alkyloxy, alkylamino, alkylacyl, acylamino, amino, or heterocylyl, and is optionally substituted with one or more $R^8$.
$R^7$ is H, alkyl or halo;
each $R^8$ is independently selected halo, hydroxyl, hydroxyalkyl, alkenyl, acylamino, thioether, oxiranyl, aryl, or aralkyl; optionally substituted with one or more $R^9$;

each $R^9$ is hydroxyl, alkyl or alkenyl; and

X is $CH_2$ or oxygen.

In certain embodiments, the present invention provides compounds having the structure of formula Ia, IIa, IIIa, IVa, Va, or VIa:

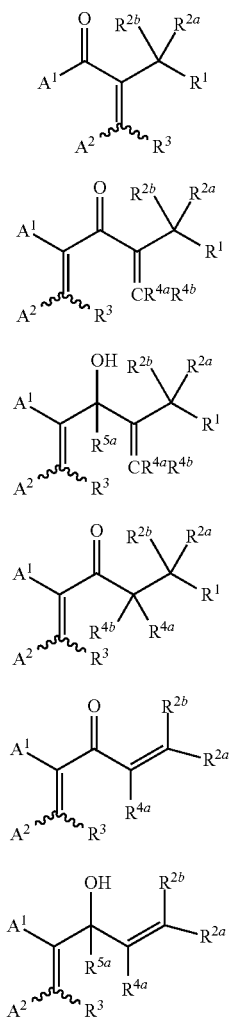

wherein:

$A^1$ is aryl or heteroaryl;

$A^2$ is aryl or heteroaryl;

$R^1$ is selected from H, $N(R^{1a}R^{1b})$, N-linked heterocyclyl, or N-linked heteroaryl;

$R^{1a}$ and $R^{1b}$ are independently selected from alkyl, aryl, and aralkyl;

$R^{2a}$ and $R^{2b}$ are independently selected from H, alkyl, or aryl;

$R^3$ is selected from H, alkyl, or halo;

$R^{4a}$ and $R^{4b}$ are independently selected from H, alkyl, or halo; and $R^{5a}$ is selected from H, alkyl, or halo.

In certain embodiments, the present invention provides compound having the structure of formula VIIa or VIIIa:

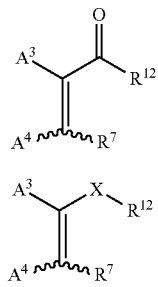

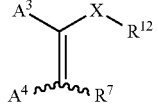

wherein:

$A^3$ is aryl or heteroaryl;

$A^4$ is aryl or heteroaryl;

$R^{12}$ is hydroxyl, alkyl, alkenyl, alkyloxy, alkylamino, alkylacyl, acylamino, or heterocylyl, and is optionally substituted with one or more $R^8$;

$R^7$ is H, alkyl or halo;

each $R^8$ is independently halo, hydroxyl, hydroxyalkyl, acylamino, thioether, oxiranyl, aryl, or aralkyl; optionally substituted with one or more $R^9$;

each $R^9$ is hydroxyl, alkyl or alkenyl; and

X is $CH_2$ or oxygen.

In certain preferred embodiments of Formula VIIa, $R^{12}$ includes a moiety capable of forming a covalent bond with a nucleophile, such as an amine or a thiol, under physiologic conditions. In certain such embodiments, $R^{12}$ comprises an oxiranylalkyl group (e.g., which may be directly linked to the carbonyl to form a ketone or indirectly linked through an oxygen or (preferably) nitrogen atom, thereby forming an ester or amide), e.g., oxiranylmethyl or oxiranylethyl. In other such embodiments, $R^{12}$ comprises a haloalkyl group (e.g., which may be directly linked to the carbonyl to form a ketone or indirectly linked through an oxygen or (preferably) nitrogen atom, thereby forming an ester or amide), e.g., a chloroethyl or chloropropyl group, which may be further substituted with one or more hydroxy groups. In yet other such embodiments, $R^{12}$ comprises an enone, such as an acrylamide or methacrylamide substituent (e.g., attached via the nitrogen atom of the amide).

In certain preferred embodiments of Formula VIIIa, $R^{12}$ includes a moiety capable of forming a covalent bond with a nucleophile, such as an amine or a thiol, under physiologic conditions. In certain such embodiments, $R^{12}$ comprises an oxiranylalkyl group (e.g., which may be directly linked to X or indirectly linked through a carbonyl (thereby forming an ester or ketone)), e.g., oxiranylmethyl or oxiranylethyl. In other such embodiments, $R^{12}$ comprises a haloalkyl group (e.g., which may be directly linked to X or indirectly linked through a carbonyl (thereby forming an ester or ketone), and may be further substituted with one or more hydroxy groups), e.g., a chloroethyl or chloropropyl group. In yet other such embodiments, $R^{12}$ comprises an enone, such as an acrylamide or methacrylamide substituent (e.g., attached via the nitrogen atom of the amide).

Exemplary compounds of Formulas I, II, III, IV, V, VI, VII and VIII include the compounds depicted in Table I.

The invention further relates to pharmaceutical compositions of the subject compounds, as well as methods of using these compounds or compositions in the treatment of cancer, such as prostate cancer.

BRIEF DESCRIPTION OF THE DRAWINGS

FIG. 12B. In vivo effects of JN series compounds. JN090, JN103, and JN121 inhibit the growth of LNCaP-AR model in castrated nude mice. Mice were administered JN090 (20 mg/kg), JN103 (20 mg/kg), JN121 (20 mg/kg), vehicle, or enzalutamide at 10 mg/kg (MDV3100) (M-F).

DETAILED DESCRIPTION

Figure 1:
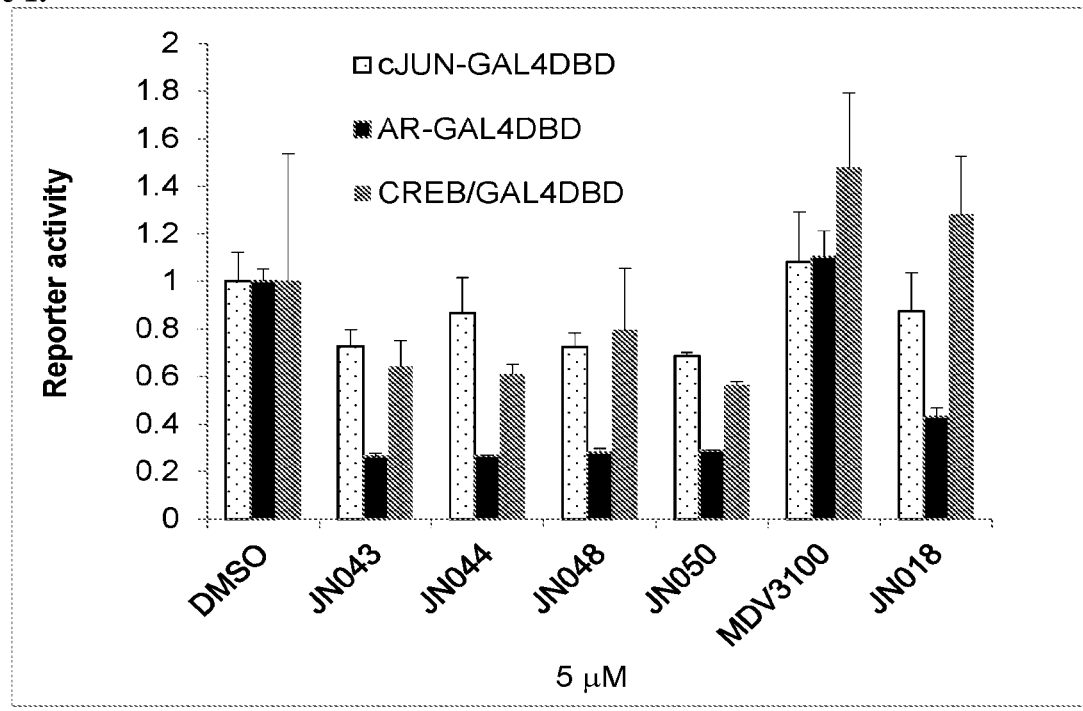
FIG. 1. shows the inhibitory effect of exemplary compounds of the invention on the JUN-TAD (left column for each compound), the AR-TAD (center column for each compound), and the CREB-TAD (right column for each compound).

In certain aspects, the present disclosure provides compounds of formula I, II, III, IV, V, VI, VII, VIII, or a pharmaceutically acceptable salt thereof:

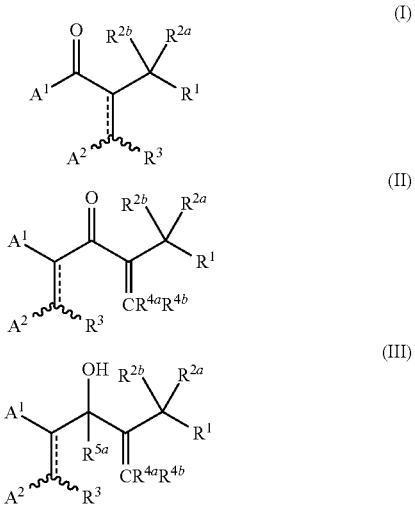

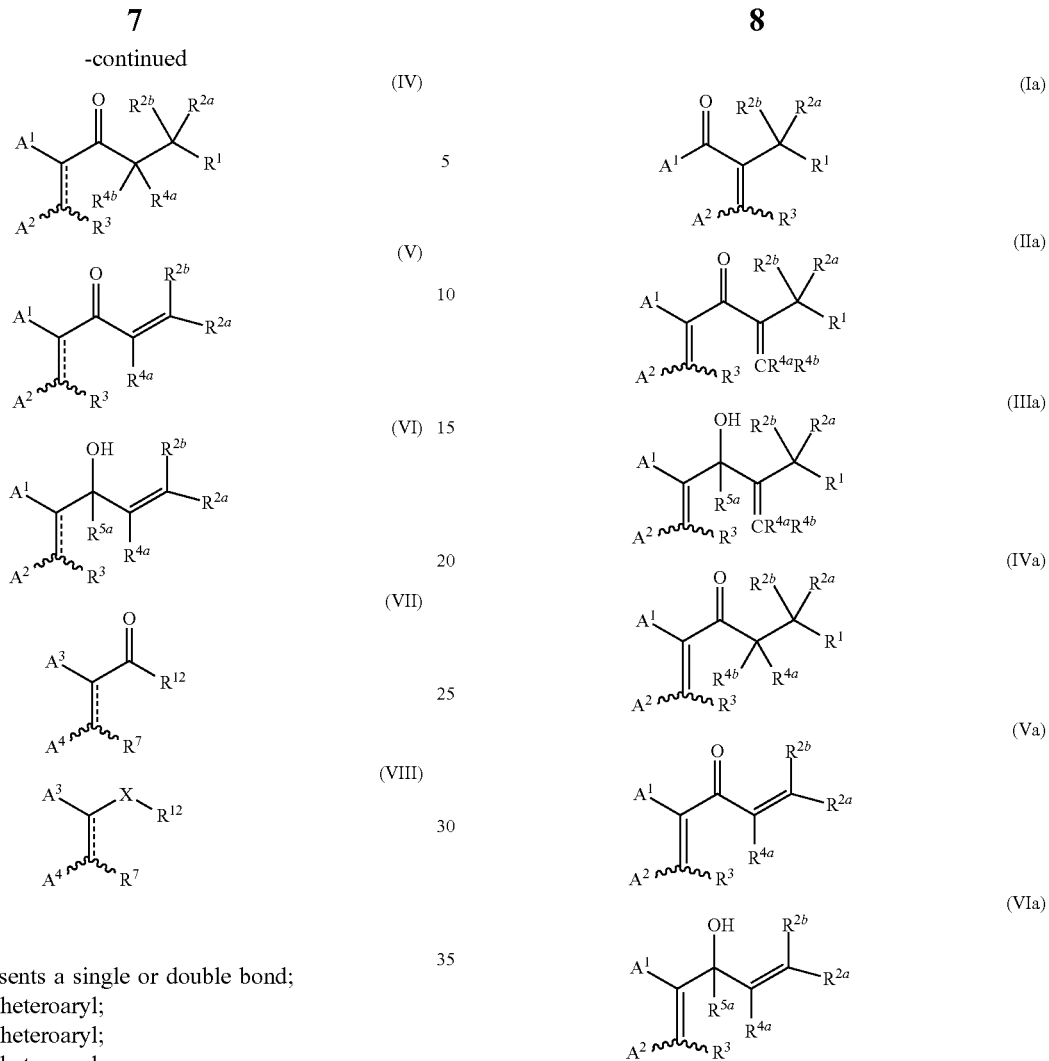

wherein
═══ represents a single or double bond;
A¹ is aryl or heteroaryl;
A² is aryl or heteroaryl;
A³ is aryl or heteroaryl;
A⁴ is aryl or heteroaryl;
R¹ is selected from H, N(R¹ᵃR¹ᵇ), N-linked heterocyclyl, or N-linked heteroaryl;
R¹ᵃ and R¹ᵇ are independently selected from alkyl, aryl, and aralkyl;
R²ᵃ and R²ᵇ are independently selected from H, alkyl, or aryl;
R³ is selected from H, alkyl, or halo;
R⁴ᵃ and R⁴ᵇ are independently selected from H, alkyl, or halo;
R⁵ᵃ is selected from H, alkyl, or halo;
R¹² is hydroxyl, alkyl, alkenyl, alkyloxy, alkylamino, alkylacyl, acylamino, amino, or heterocylyl, and is optionally substituted with one or more R⁸;
R⁷ is H, alkyl or halo;
each R⁸ is independently halo, hydroxyl, hydroxyalkyl, alkenyl, acylamino, thioether, oxiranyl, aryl, or aralkyl; optionally substituted with one or more R⁹;
each R⁹ is hydroxyl, alkyl or alkenyl; and
X is CH₂ or oxygen.

In certain embodiments, ═══ represents a single bond. In certain preferred embodiments, ═══ represents a double bond.

In certain embodiments, the present disclosure provides compounds of formula Ia, IIa, IIIa, IVa, Va, VIa, or a pharmaceutically acceptable salt thereof:

wherein:
A¹ is aryl or heteroaryl;
A² is aryl or heteroaryl;
R¹ is selected from H, N(R¹ᵃR¹ᵇ), N-linked heterocyclyl, or N-linked heteroaryl;
R¹ᵃ and R¹ᵇ are independently selected from alkyl, aryl, and aralkyl;
R²ᵃ and R²ᵇ are independently selected from H, alkyl, or aryl;
R³ is selected from H, alkyl, or halo;
R⁴ᵃ and R⁴ᵇ are independently selected from H, alkyl, or halo; and
R⁵ᵃ is selected from H, alkyl, or halo.

In certain embodiments, the compound is represented by formula Ia. In certain embodiments, the compound is represented by formula IIa. In certain embodiments, the compound is represented by formula IIIa. In certain embodiments, the compound is represented by formula IVa. In certain embodiments, the compound is represented by formula Va. In certain embodiments, the compound is represented by formula VIa.

In certain embodiments of formula I, II, III, IV, V, VI, Ia, IIa, IIIa, IVa, Va, and VIa, A¹ and A² are cis- to one another. In other embodiments, A¹ and A² are trans- to one another.

In certain embodiments of formula I, II, III, IV, V, VI, Ia, IIa, IIIa, IVa, Va, and VIa, A² is not 4-chlorophenyl; A¹ is not unsubstituted phenyl; $R^1$ is not N-benzyl methyl amino; $R^{2a}$ and $R^{2b}$ are not both H; or $R^3$ is not H.

In certain embodiments of formula II and IIa, the compound is not JN018.

In certain embodiments of formula I, II, III, IV, V, VI, Ia, IIa, IIIa, IVa, Va, and VIa, $A^1$ and $A^2$ are phenyl. In certain embodiments, $A^1$ is heteroaryl. In certain embodiments, $A^2$ is heteroaryl.

In certain embodiments, $A^1$ is unsubstituted or substituted by at least one $R^5$, wherein each $R^5$ is independently selected from halo, alkyl, or alkoxy. In certain embodiments, $A^1$ is unsubstituted. In certain embodiments, $A^1$ is substituted by at least one $R^5$. In certain embodiments, $A^1$ is substituted by one or two $R^5$.

In certain embodiments, $A^2$ is unsubstituted or substituted by at least one $R^5$, wherein each $R^6$ is independently selected from halo, alkyl, or alkoxy. In certain embodiments, each $R^6$ is independently selected from alkyl, or alkoxy. In certain embodiments, $A^2$ is unsubstituted. In certain embodiments, $A^2$ is substituted by at least one $R^6$. In certain embodiments, $A^2$ is substituted by one or two $R^6$. In certain preferred embodiments, $A^2$ is selected from methylphenyl, trifluoromethylphenyl, fluorophenyl, chlorophenyl, or dichlorophenyl.

In certain embodiments of formula I, II, III, IV, Ia, IIa, IIIa, and IVa, $R^1$ is $N(R^{1a}R^{1b})$. In certain preferred embodiments, $R^{1a}$ is alkyl and $R^{1b}$ is aralkyl. In certain such embodiments, $R^1$ is $N(R^{1a}R^{1b})$, $R^{1a}$ is methyl and $R^{1b}$ is benzyl.

In certain embodiments, $R^{1a}$ and $R^{1b}$ are independently selected from alkyl. In certain embodiments, $R^{1a}$ and $R^{1b}$ are isobutyl. In certain preferred embodiments, $R^{1a}$ and $R^{1b}$ are methyl.

In certain embodiment, $R^1$ is N-linked heterocyclyl or heteroaryl.

In certain embodiments, $R^1$ is unsubstituted or substituted with at least one $R^7$, wherein each $R^7$ is independently selected from alkyl or aryl. In certain embodiments, $R^1$ is unsubstituted. In certain preferred embodiments, $R^1$ is pyrrolidine, piperidine, or piperazine.

In certain embodiments $R^1$ is H.

In certain embodiments of formula I, II, III, IV, V, VI, Ia, IIa, IIIa, IVa, Va, and VIa, $R^{2a}$ and $R^{2b}$ are H.

In certain embodiments, $R^{2a}$ and $R^{2b}$ are independently selected from alkyl and halo.

In certain embodiments of formula I, II, III, IV, V, VI, Ia, IIa, IIIa, IVa, Va, and VIa, $R^3$ is H.

In certain embodiments, $R^3$ is alkyl or halo.

In certain embodiments, the compound is represented by formula (II) and $R^{4a}$ and $R^{4b}$ are H.

In certain embodiments of formula I, II, Ia and IIa, the compound is represented by formula Ib or IIb:

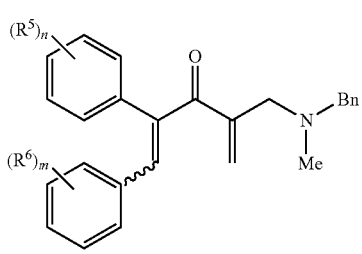

(Ib)

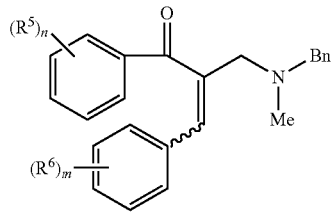

(IIb)

wherein:
each $R^5$ is independently selected from halo, alkyl, or alkyloxy;
each $R^6$ is independently selected from halo, alkyl, or alkyloxy;
n is 0, 1, 2, 3, 4, or 5; and
m is 0, 1, 2, 3, 4, or 5.

In certain embodiments of formula (Ib) and (IIb), n is 0. In certain embodiments, m is 1 and $R^6$ is selected from fluoro, chloro, bromo, methyl, trifluoromethyl, or methoxy. In certain embodiments, $R^6$ is selected from fluoro, bromo, methyl, trifluoromethyl, or methoxy.

In certain embodiments of formula (Ib) and (IIb), n is 1, 2, 3, 4, or 5.

In certain embodiments, the compound has structure of formula VII or VIII, or a pharmaceutically acceptable salt thereof:

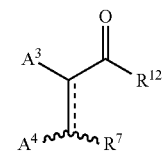

(VII)

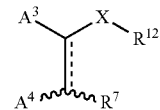

(VIII)

wherein:
═══ represents a single or double bond;
$A^3$ is aryl or heteroaryl;
$A^4$ is aryl or heteroaryl;
$R^{12}$ is hydroxyl, alkyl, alkenyl, alkyloxy, alkylamino, alkylacyl, acylamino, amino, or heterocyclyl, and is optionally substituted with one or more $R^8$; $R^7$ is H, alkyl or halo;
each $R^8$ is independently halo, hydroxyl, hydroxyalkyl, alkenyl, acylamino, thioether, oxiranyl, aryl, or aralkyl; optionally substituted with one or more $R^9$;
each $R^9$ is hydroxyl, alkyl, alkoxy, or alkenyl; and
X is $CH_2$ or oxygen.

In certain embodiments of formula VII, VIII, VIIa and VIIIb, $R^{12}$ is amino, and is optionally substituted with one or more $R^8$, selected from alkyl.

In certain embodiments, $R^{12}$ is acylamino, optionally substituted with one or more $R^8$, selected from alkenyl.

In certain embodiments, $R^{12}$ is heterocylyl, such as tetrahydropyrimidinyl, and is optionally substituted with one or more $R^8$, selected from phenyl.

In certain embodiments of formula VII, VIII, VIIa and VIIIb, $R^8$ is optionally substituted with one or more $R^9$, selected from alkoxy.

In certain preferred embodiments of formula VII and VIII, the compound has the structure of formula VIIa or VIIIa or a pharmaceutically acceptable salt thereof:

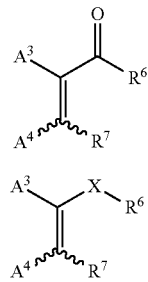

(VIIa)

(VIIIa)

wherein:
A$^3$ is aryl or heteroaryl;
A$^4$ is aryl or heteroaryl;
R$^{12}$ is hydroxyl, alkyl, alkenyl, alkyloxy, alkylamino, alkylacyl, acylamino, or heterocylyl, and is optionally substituted with one or more R$^8$.
R$^7$ is H, alkyl or halo;
each R$^8$ is independently halo, hydroxyl, hydroxyalkyl, acylamino, thioether, oxiranyl, aryl, or aralkyl; optionally substituted with one or more R$^9$;
each R$^9$ is hydroxyl, alkyl or alkenyl; and
X is CH$_2$ or oxygen.

In certain embodiments, the compound is represented by formula VIIa.

In certain embodiments of formula VIIa, R$^{12}$ is alkyl substituted with at least one R$^8$. In certain embodiments, R$^{12}$ is acylamino, and is optionally substituted with one or more R$^8$. In certain embodiments, R$^{12}$ is alkenyl, such as allyl, and is optionally substituted with one or more R$^8$. In certain embodiments, R$^{12}$ is substituted with one R$^8$ group selected from halo. In certain embodiments, R$^{12}$ is substituted with hydroxyl. In certain preferred embodiments, R$^{12}$ is substituted with one R$^8$ group selected from halo and one hydroxyl.

In certain embodiments, R$^{12}$ is substituted with oxiranyl. In certain preferred embodiments, R$^{12}$ is oxiranylmethyl.

In certain embodiments, R$^{12}$ is substituted with alkyl. In certain embodiments, R$^{12}$ is substituted with hydroxyalkyl. In certain embodiments, R$^{12}$ is substituted with thioether, such as benzylthiomethyl.

In certain embodiments of formula VIIa, R$^9$ is alkenyl. In certain embodiments, R$^{12}$ is alkenyl, and is optionally substituted with one or more R$^8$.

In certain embodiments of formula VII and VIIa, the compound is represented by formula VIIb:

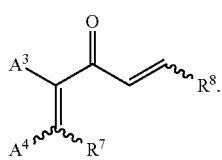

(VIIb)

In certain embodiments of formula VIIb, R$^8$ is hydroxyalkyl, such as hydroxymethyl.

In certain embodiments, the compound is represented by formula VIII. In certain preferred embodiments of formula VIII, the compound is represented by formula VIIIa.

In certain embodiments of formula VIII and VIIIa, X is oxygen. In certain embodiments, X is CH$_2$.

In certain embodiments of formula VIII and VIIIa, R$^{12}$ is amino. In certain embodiments, R$^{12}$ is alkylacyl. In certain embodiments, R$^{12}$ is hydroxyl. In certain embodiments, R$^{12}$ is

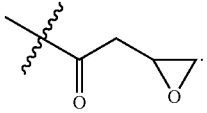 [SMILES: *C(=O)CC1CO1]

In certain embodiments, R$^{12}$ is acylamino, optionally substituted with one or more R$^8$ selected from alkenyl. In certain embodiments, R$^8$ is oxiranyl.

In certain embodiments of formula VIII and VIIIa, A$^3$ is unsubstituted. In certain embodiments, A$^3$ is 4-fluorophenyl. In certain embodiments, A$^3$ is trifluorophenyl, such as 2,4,6-trifluorophenyl. In certain embodiments, A$^3$ is heteroaryl, such as thiophenyl.

In certain embodiments of formula VIII and VIIIa, A$^4$ is chlorophenyl, such as 3-chlorophenyl, 4-chlorophenyl. In certain embodiments, A$^4$ is trifluoromethylphenyl, such as 3-trifluoromethylphenyl. In certain embodiments, A$^4$ is 3-chloro-4-(trifluoromethyl)phenyl. In certain embodiments, A$^4$ is heteroaryl, such as thiophenyl. In certain embodiments, A$^3$ is phenyl and A$^4$ is chlorophenyl.

In certain embodiments of formula VIII or VIIIa, A$^3$ and A$^4$ are trans- to one another. In certain preferred embodiments, A$^3$ and A$^4$ are cis- to one another.

In certain embodiments of formula VIII or VIIIa, R$^{12}$ lacks an amino group.

In certain embodiments of formula VII and VIIa, the compound is represented by formula VIIb:

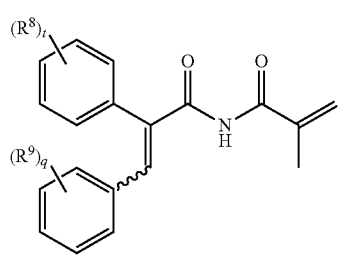

(VIIb)

wherein:
each R$^8$ is independently selected from halo, alkyl, or alkyloxy;
each R$^9$ is independently selected from halo, alkyl, or alkyloxy;
t is 0, 1, 2, 3, 4, or 5; and
q is 0, 1, 2, 3, 4, or 5.

In certain preferred embodiments of formula VIIb, R$^8$ is halo, preferably fluoro or chloro.

In certain preferred embodiments of formula VIIb, R$^9$ is halo, preferably fluoro or chloro. In other preferred embodiments, R$^9$ is alkyl.

In certain preferred embodiments of formula VIIb, t is 1, 2 or 3.

In certain preferred embodiments of formula VIIb, q is 1, 2 or 3.

In certain embodiments of formula VII and VIIa, the compound is represented by formula VIIc:

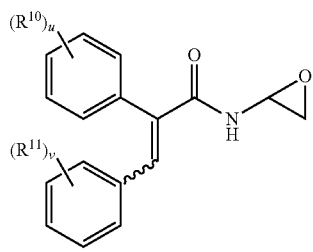

(VIIc)

wherein:
each $R^{10}$ is independently selected from halo, alkyl, or alkyloxy;
each $R^{11}$ is independently selected from halo, alkyl, or alkyloxy;
u is 0, 1, 2, 3, 4, or 5; and
v is 0, 1, 2, 3, 4, or 5.

In certain preferred embodiments of formula VIIc, $R^{10}$ is halo, preferably fluoro.

In certain preferred embodiments of formula VIIc, $R^{11}$ is halo, preferably chloro.

In certain preferred embodiments of formula VIIc, u is 1.
In certain preferred embodiments of formula VIIc, v is 1.

The compounds described herein are useful, for example, as cancer therapeutics, in particular as AR inhibitors and degraders. In certain aspects, the present disclosure provides methods of treating proliferative diseases, such as prostate cancer, methods of inhibiting AR, and methods of enhancing AR degradation rates using the compounds described herein.

In certain aspects, the compounds of the present disclosure are for use in inhibiting an androgen receptor.

In certain aspects, the compounds of the present disclosure are for use in inducing degradation of an androgen receptor in a cell expressing an androgen receptor.

In certain aspects, the compounds of the present disclosure are for use in treating a mammal suffering from cancer. In certain embodiments, the cancer is prostate cancer. In certain embodiments, the cancer is castration-resistant prostate cancer. In certain embodiments, the cancer is metastatic. In certain embodiments, the cancer is non-metastatic.

In certain embodiments of the above aspects, the cancer is resistant to antiandrogen therapy. In certain embodiments, the cancer is resistant to treatment with enzalutamide, bicalutamide, abiraterone, flutamide, or nilutamide. In certain embodiments, the cancer is resistant to treatment with abiraterone acetate. In certain embodiments, the cancer is resistant to conjoint treatment with abiraterone acetate and prednisone.

In certain aspects, the present disclosure provides methods of inhibiting an androgen receptor, comprising contacting the androgen receptor with a compound or composition of the disclosure.

In certain aspects, the present disclosure provides methods of inducing the degradation of an androgen receptor, comprising contacting the androgen receptor with a compound or composition of the disclosure.

In certain aspects, the present disclosure provides methods of treating a mammal suffering from cancer, comprising administering a compound or composition of the disclosure. In certain embodiments, the cancer is prostate cancer. In certain embodiments, the cancer is castration-resistant prostate cancer. In certain embodiments, the cancer is metastatic. In certain embodiments, the cancer is non-metastatic.

In certain embodiments of the above aspects, the cancer is resistant to antiandrogen therapy. In certain embodiments, the cancer is resistant to treatment with enzalutamide, bicalutamide, abiraterone, flutamide, or nilutamide. In certain embodiments, the cancer is resistant to treatment with abiraterone acetate. In certain embodiments, the cancer is resistant to conjoint treatment with abiraterone acetate and prednisone.

In certain embodiments, compounds of the invention are prodrugs of the compounds described herein. For example, wherein a hydroxyl in the parent compound is presented as an ester or a carbonate, or a carboxylic acid present in the parent compound is presented as an ester. In certain such embodiments, the prodrug is metabolized to the active parent compound in vivo (e.g., the ester is hydrolyzed to the corresponding hydroxyl or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomers. For example, a compound of the invention may have greater than 30% de, 40% de, 50% de, 60% de, 70% de, 80% de, 90% de, or even 95% or greater de.

In certain embodiments, the present invention provides pharmaceutical compositions comprising a compound described herein, such as a compound of Formula I, II, III, IV, V, VI, VII or VIII. In certain embodiments, the pharmaceutical compositions further comprise a pharmaceutically acceptable excipient.

In certain embodiments, the pharmaceutical compositions may be for use in treating or preventing a condition or disease as described herein.

In certain embodiments, the present invention relates to methods of treatment with a compound described herein. In certain embodiments, the therapeutic preparation may be enriched to provide predominantly one enantiomer or isomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound. A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising any of the compounds shown above, and one or more pharmaceutically acceptable excipients.

Compounds of any of the above structures may be used in the manufacture of medicaments for the treatment of any diseases or conditions disclosed herein.

Discussion

The present disclosure describes compounds that inhibit the AR in novel ways. In mammalian cell systems, the compounds of Formulas I, II, III, IV, V, VI, VII or VIII inhibit ligand-induced and constitutive AR transcriptional activity, and enhance AR degradation. The activity of endogenously and ectopically expressed wild-type and splice variant ARs is inhibited by JN018 over a wide range of concentrations and in a dose-dependent fashion. Importantly, JN018 does not inhibit the transcriptional activity of the closely related glucocorticoid receptor (GR). Domain swapping experiments revealed that JN018 inhibits the transactivation domain (TAD) of the AR. JN018 reduces the expression of AR target genes, including TMPRSS and NDRG. JN018 inhibited the growth of AR expressing prostate cancer cells in a dose-dependent fashion, but had no effect on AR null models. Mechanistic studies establish that JN018 targets the AR and its splice variants for degradation.

The compounds disclosed herein target the AR N-terminal TAD. These compounds, such as JN018, can be used to treat diseases, the growth of which is driven by the AR or its splice variants. Prostate cancer is an example of one such disease. These compounds offer competitive advantages over existing, approved compounds that target the AR because existing compounds target the LBD of the AR, whereas JN018 and are active against full length and constitutively active AR variants that lack a functional LBD (see below, section 6 for more details). JN018 targets the AR N-terminus and inhibits the activity of constitutively active AR variants that lack a functional LBD (see below, section 6 for more details). These AR variants have been shown to confer resistance to currently approved AR targeting agents. In addition, JN018 induces degradation of the AR including AR splice variants, which is not a known mechanism of any AR targeting agent that has received regulatory approval. These AR variants have been shown to confer resistance to current AR targeting agents.

Compositions and Modes of Administration

The compounds of this invention may be used in treating the conditions described herein, in the form of the free base, salts (preferably pharmaceutically acceptable salts), solvates, hydrates, prodrugs, isomers, or mixtures thereof. All forms are within the scope of the disclosure. Acid addition salts may be formed and provide a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the subject organism in pharmaceutical doses of the salts, so that the beneficial properties inherent in the free base are not vitiated by side effects ascribable to the anions. Although pharmaceutically acceptable salts of the basic compounds are preferred, all acid addition salts are useful as sources of the free base form even if the particular salt per se is desired only as an intermediate product as, for example, when the salt is formed only for the purposes of purification and identification, or when it is used as an intermediate in preparing a pharmaceutically acceptable salt by ion exchange procedures.

Pharmaceutically acceptable salts within the scope of the disclosure include those derived from the following acids; mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The compounds of the present invention can be formulated as pharmaceutical compositions and administered to a subject in need of treatment, for example a mammal, such as a human patient, in a variety of forms adapted to the chosen route of administration, for example, orally, nasally, intraperitoneally, or parenterally (e.g., by intravenous, intraperitoneal, subcutaneous, intramuscular, transepithelial, nasal, intrapulmonary, intrathecal, rectal or topical routes). Parenteral administration may be by continuous infusion over a selected period of time.

In accordance with the methods of the disclosure, the described compounds may be administered to a patient in a variety of forms depending on the selected route of administration, as will be understood by those skilled in the art. The compositions containing the compounds of the disclosure can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

A composition comprising a compound of the present disclosure may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

Thus, compounds of the invention may be systemically administered, e.g., orally, in combination with a pharmaceutically acceptable vehicle such as an inert diluent or an assimilable edible carrier; or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with a fine inert powdered carrier and inhaled by the subject or insufflated. Such compositions and preparations should contain at least 0.1% of compounds of formulas I, II, III, IV, V, VI, VII or VIII. The percentage of the compositions and preparations may, of course, be varied and may conveniently be between about 2% to about 60% of the weight of a given unit dosage form. The amount of the compounds in such therapeutically useful compositions is such that an effective dosage level will be obtained.

In certain embodiments of the disclosure, compositions comprising a compound of the present disclosure for oral administration include capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the compound of the present disclosure as an active ingredient.

In solid dosage forms for oral administration (capsules, tablets, troches, pills, dragees, powders, granules, and the like), one or more compositions comprising the compound of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, gum tragacanth, corn starch, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the compounds may be incorporated into sustained-release preparations and devices. For example, the compounds may be incorporated into time release capsules, time release tablets, and time release pills.

Liquid dosage forms for oral administration include pharmaceutically acceptable emulsions, microemulsions, solutions, suspensions, syrups, and elixirs. In addition to the compound of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compounds, salts and/or prodrugs thereof, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In certain embodiments, pharmaceutical compositions suitable for parenteral administration may comprise the compound of the present disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compounds may be administered intravenously or intraperitoneally by infusion or injection. Solutions of the compounds or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formulas I, II, III, IV, V, VI, VII or VIII can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds of formulas I, II, III, IV, V, VI, VII or VIII are conveniently administered in unit dosage form; for example, containing 0.05 to 10000 mg, 0.5 to 10000 mg, 5 to 1000 mg, or about 100 mg of active ingredient per unit dosage form.

The compounds can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. For example, plasma levels may be from about 1 to 100 micromolar or from about 10 to about 25 micromolar. This may be achieved, for example, by the intravenous injection of a 0.05 to 5% solution of the compounds, optionally in saline, or orally administered as a bolus containing about 1-100 mg of the compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the compounds per kg of body weight.

The compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

The dosage of the compounds and/or compositions of the disclosure can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. The compounds of the disclosure may be administered initially in a suitable dosage that may be adjusted as required, depending on the clinical response. To calculate the human equivalent dose (HED) from a dosage used in the treatment of age-dependent cognitive impairment in rats, the formula HED (mg/kg)=rat dose (mg/kg)×0.16 may be employed (see Estimating the Safe Starting Dose in Clinical Trials for Therapeutics in Adult Healthy Volunteers, December 2002, Center for Biologics Evaluation and Research). For example, using that formula, a dosage of 10 mg/kg in rats is equivalent to 1.6 mg/kg in humans. This conversion is based on a more general formula HED=animal dose in mg/kg×(animal weight in kg/human weight in kg) 0.33. Similarly, to calculate the HED from a dosage used in the treatment in mouse, the formula HED (mg/kg)=mouse dose (mg/kg)×0.08 may be employed (see Estimating the Safe Starting Dose in Clinical Trials for Therapeutics in Adult Healthy Volunteers, December 2002, Center for Biologics Evaluation and Research).

The compounds and/or compositions of the disclosure can be used alone or conjointly with other therapeutic agents, or in combination with other types of treatment for treating cell proliferative disorders such as prostate cancer. For example, in some embodiments, the compounds and compositions of the disclosure can be used for treating CRPC or for treating cancers that are resistant to antiandrogen therapies such as enzalutamide, bicalutamide, abiraterone, flutamide, or nilutamide. For example, these other therapeutically useful agents may be administered in a single formulation, simultaneously or sequentially with the compound of the present disclosure according to the methods of the disclosure.

A number of the above-identified compounds exhibit little or no agonistic activities with respect to hormone refractory prostate cancer cells. Because these compounds are strong AR inhibitors, they can be used not only in treating prostate cancer, but also in treating other AR related diseases or conditions such as benign prostate hyperplasia, hair loss, and acne.

Because AR belongs to the family of nuclear receptors, these compounds may serve as scaffolds for drug synthesis targeting other nuclear receptors, such as estrogen receptor and peroxisome proliferator-activated receptor. Therefore, they may be further developed for other diseases such as breast cancer, ovarian cancer, diabetes, cardiac diseases, and metabolism related diseases, in which nuclear receptors play a role.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g. solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x toy carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

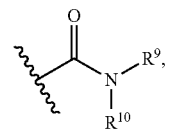

wherein R$^9$ and R$^{10}$ each independently represent a hydrogen or hydrocarbyl group, or R$^9$ and R$^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

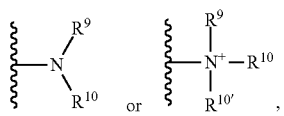

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

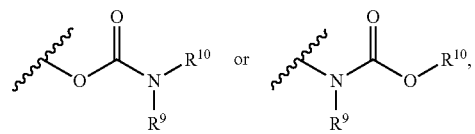

wherein $R^9$ and $R^{10}$ independently represent hydrogen or a hydrocarbyl group.

The term "carbocyclylalkyl", as used herein, refers to an alkyl group substituted with a carbocycle group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —C(O)$OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings".

Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

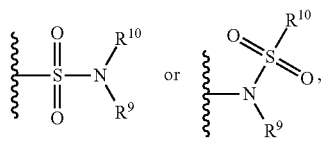

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

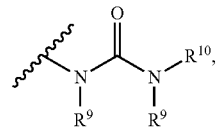

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by formulas I, II, III, IV, V, VI, VII or VIII. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of formulas I, II, III, IV, V, VI, VII or VIII are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of formulas I, II, III, IV, V, VI, VII or VIII for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by formulas I, II, III, IV, V, VI, VII or VIII or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formulas I, II, III, IV, V, VI, VII or VIII). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of formulas I, II, III, IV, V, VI, VII or VIII. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

Discussion

Adenocarcinoma of the prostate (PCa) is the most common non-cutaneous solid tumor diagnosed in men in the U.S. and represents the second leading cause of cancer-related mortality in men, second only to lung cancer. PCa is initially androgen dependent (AD), and androgen deprivation therapy (ADT), which is delivered by surgical or chemical castration in the form of luteinizing hormone releasing hormone (LHRH) analogues (FIG. 5A), results in apoptosis and growth arrest of AD PCa cells and induces a clinical response in virtually all patients. Unfortunately, castration resistant prostate cancer (CRPC) inevitably develops and not only represents the terminal phase of the disease with a median survival of approximately 12-15 months, but also is associated with profound morbidity. Until recently, the chemotherapeutic agent, docetaxel, was the only systemic therapy for CRPC that prolonged median overall survival, albeit by a modest two to three months. In 2010, another cytotoxic chemotherapeutic, cabazitaxel, was also granted regulatory approval for docetaxel-resistant patients based on a three month improvement in survival, as was the cellular vaccine, Provenge, which extended survival by four months in a highly select sub-group of patients with excellent performance status. Thus, despite these modest, incremental advances, novel treatment approaches based on an understanding of the biology behind castration resistance are required to more substantially improve the outcomes of CRPC patients.

A large body of experimental and clinical evidence has established that restoration of AR activity underlies therapeutic resistance in the vast majority of CRPC patients. Although the AR has non-genotropic effects, reactivation of AR transcriptional activity represents the principal biochemical driving force that is necessary and sufficient for castration resistance. Cellular adaptations, including 1) AR gene amplification, 2) intratumoral steroidogenesis, 3) gain-of-function AR gene mutations that allow for ligand promiscuity, 4) somatic mosaicism of the AR, 5) heightened expression of AR transcriptional coactivators, 6) as well as truly ligand-independent AR activation mediated by growth factors, cytokines, and AR phosphorylation, are mutually non-exclusive mechanisms that drive AR transcriptional activity despite castrate serum levels of androgens. Activating mutations of the AR signaling axis has been identified in nearly all cases of CRPC in a recent integrative genomic analysis of over 200 CRPC patients.

Figure 5:
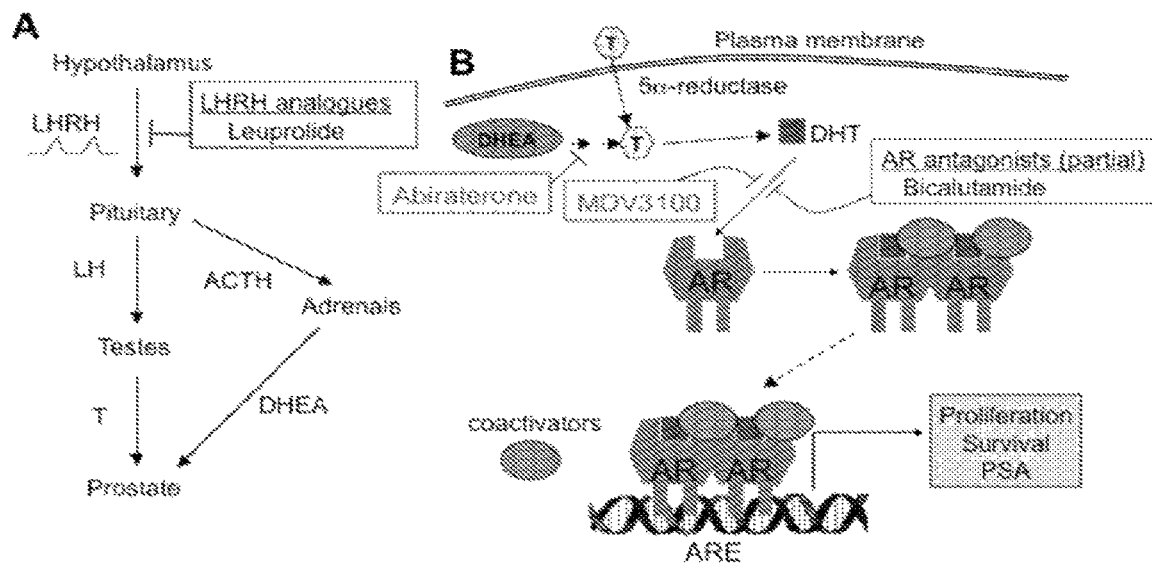
FIG. 5. is a schematic depiction of cellular processes related to AR signaling and therapeutic targeting. A) Physiologic regulation of androgen synthesis. Pulsatile secretion of LHRH induces luteinizing hormone (LH) secretion by the anterior pituitary, which in turn drives testosterone (T) synthesis and secretion by the testes, from which 90-95% of androgens are derived. LHRH analogues, by providing continuous, unremitting engagement of the LHRH receptors on the anterior pituitary, suppress LH secretion. The adrenal glands are a minor source of androgens; adrenal androgens (e.g. DHEA) are converted into T or dihydrotestosterone (DHT) in peripheral tissues. B) AR working mechanism. Upon ligand binding, AR dimerizes, translocates to the nucleus, and induces gene transcription. Novel AR targeting agents (in red), inhibit intratumoral steroidogenesis (e.g., abiraterone, a 17α-hydroxylase inhibitor) or function as pure AR antagonists (e.g., MDV3100). C) Schematic of full-length AR ($AR^{FL}$), the constitutively active ARΔLBD, and a Y1H system that can serve as the basis for a high-throughput screening assay. The ligand-independent ARΔLBD, when expressed in our genetically modified, drug permeable yeast strain, binds to tandem copies of the ARE, which induces the expression of a reporter gene. ⊥ inhibition; → activation; NLS: nuclear localization signal.
Figure 6:
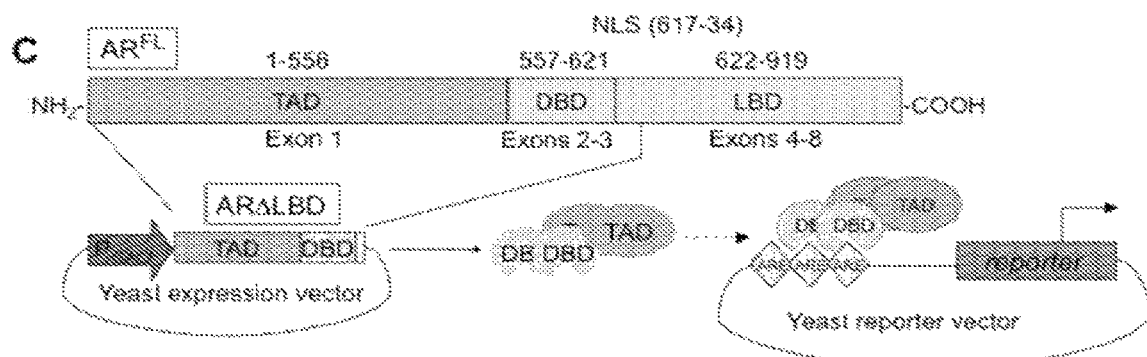
FIG. 6. Schematic of primary amino acid structure of full-length AR and a constitutively active AR splice variant that lacks a functional LBD.
Figure 6:
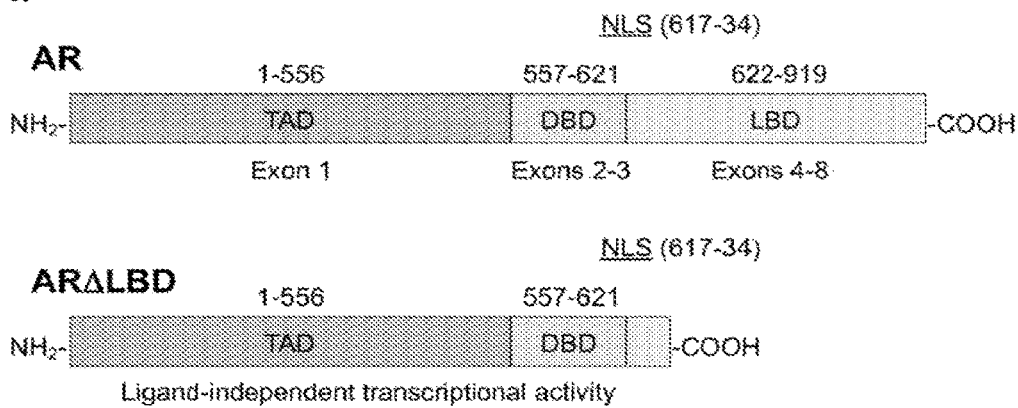

Based on these observations, drugs that target the AR signaling axis through novel approaches, including pure AR antagonists (e.g. enzalutamide) and CYP17 inhibitors aimed at inhibiting intratumoral steroidogenesis (e.g. abiraterone acetate) have made their way through the clinic (FIG. 5B). Abiraterone acetate and enzalutamide have both been approved for the treatment of metastatic CRPC (mCRPC). However, primary resistance to these agents occurs in roughly one third of patients, while the remaining patients develop secondary resistance manifested by progression of disease after an initial period of response of variable duration.

The phase 3 studies that demonstrated the clinical success of abiraterone acetate and enzalutamide in chemotherapy naïve and post-chemotherapy patients confirmed the pathophysiologic relevance of the AR as a driver of castration resistance. Cross-resistance between abiraterone and enzalutamide is the norm as evidenced by the low response rate when one of these agents is used subsequent to progression on the other. Since the clinical implementation of these second-generation endocrine therapies, pre-clinical models as well as sequencing studies of cohorts of mCRPC patients have demonstrated ongoing AR expression and signaling in post-abiraterone/post-enzalutamide mCRPC. In fact, the AR is the most frequently mutated gene, and an AR-dependent transcriptional program is reactivated in this context. Thus, the AR represents a key driver of castration resistant growth in both newly developed CRPC and post-abiraterone/post-enzalutamide CRPC.

Constitutively active variants of the AR that lack a functional LBD have recently been shown to be expressed in prostate cancer specimens with increasing frequency in mCRPC specimens. These constitutively active variants confer resistance to abiraterone acetate and enzalutamide; in fact, these variants would not be expected to respond to any existing drug that directly or indirectly targets the LBD. Given the inevitable development of primary or secondary resistance to abiraterone and enzalutamide and the pathophysiologic relevance of the AR throughout the natural and treated history of the castration resistant state, there is an unmet need to develop novel AR targeting agents to improve the clinical outcomes of patients with metastatic CRPC.

All existing endocrine therapies in clinical use for the treatment of PCa, including but not limited to abiraterone and enzalutamide, directly or indirectly target the C-terminal ligand binding domain (LBD) of the AR. The C-terminal LBD of the AR represents the direct or indirect molecular target of new AR targeting agents in development as well as those that have long been employed, including luteinizing hormone releasing hormone (LHRH) analogues (e.g. leuprolide, a "chemical castration") and partial AR antagonists (e.g. bicalutamide) (FIG. 5C). The other major domains of the AR, including the centrally located DNA binding domain (DBD) and N-terminal transactivation domain (TAD), have yet to be directly targeted and exploited for therapeutic benefit. These domains are required for AR transcriptional activity, yet no drug that targets either of these domains has been successfully brought to the point of regulatory approval to date. The centrally located DBD shares significant homology with other members of the nuclear steroid receptor family (e.g. glucocorticoid receptor [GR], progesterone receptor [PR]), whereas the N-terminally located AR TAD shares the least homology with that of other members of this family and accordingly could be selectively targeted.

The AR TAD is an intrinsically disordered protein that has not been amenable to crystallization. Hence, its structure has not been resolved, and, by extension, the AR TAD does not lend itself to structure based drug design. Proof-of-principle support for the notion of targeting the TAD has come from studies in which TAD decoy molecules inhibited AR-dependent growth.

Proof-of-principle support for the notion of targeting the TAD has come from recent studies by a group that identified TAD decoy molecules as well as a marine sponge extract that selectively targets the AR TAD. Importantly, this marine sponge extract, known as EPI-001, inhibited CRPC growth through interaction with the AF1 region of the TAD. EPI-001 was not identified through a high throughput screen, and is likely to have been absorbed by marine sponges in vivo as an industrial compound. Other compounds have been shown to have an inhibitory effect on constitutively active AR splice variants. Galeterone binds to the AR LBD but was reported to induce degradation of AR splice variants. Galeterone entered into clinical trials, but a phase 3 studied was recently discontinued at an interim analysis due to futility. Niclosamide, an anti-fungal agent, also inhibits AR splice variants and has entered into early phase clinical trials.

It has been discovered that compound JN018 exhibits potent, specific AR inhibitory effects:

In particular, JN018 has the following properties: (1) AR TAD is its molecular target. (2) JN018 exhibits direct, selective, high affinity covalent binding to the AR. (3) JN018 induces rapid degradation of the full-length AR (ARFL) and constitutively active AR splice variants (ARSV) that lack a functional LBD. (4) JN018 exhibits selective cytoreductive effects on AR-expressing prostate cancer cell lines, including ARSV expressing cell lines. (5) JN018 causes growth inhibition of castration resistant prostate cancer xenografts. (6) JN018 inhibits AR-driven gene expression.

For example, JN018 inhibits reporter activity driven by the ARE and MMTV promoters, but does not affect GR, AP1, or CREB mediated reporter activity. Importantly, JN018 inhibits the reporter activity of the endogenously and ectopically expressed full-length AR and AR-V7 (constitutively active AR splice variant) in the following cell systems: 1) LNCaP, which endogenously expresses full length AR, 2) LNCaP-AR, which is engineered to overexpress full length AR to recapitulate castration resistance, 3) 22Rv1, which expresses both full-length AR and the constitutively active ARV7, and 4) PC3 cells, which are AR null but were transfected with constitutively active ARA567.

In addition to JN018, a number of additional compounds have been prepared and tested, as listed in Table 1:

TABLE 1

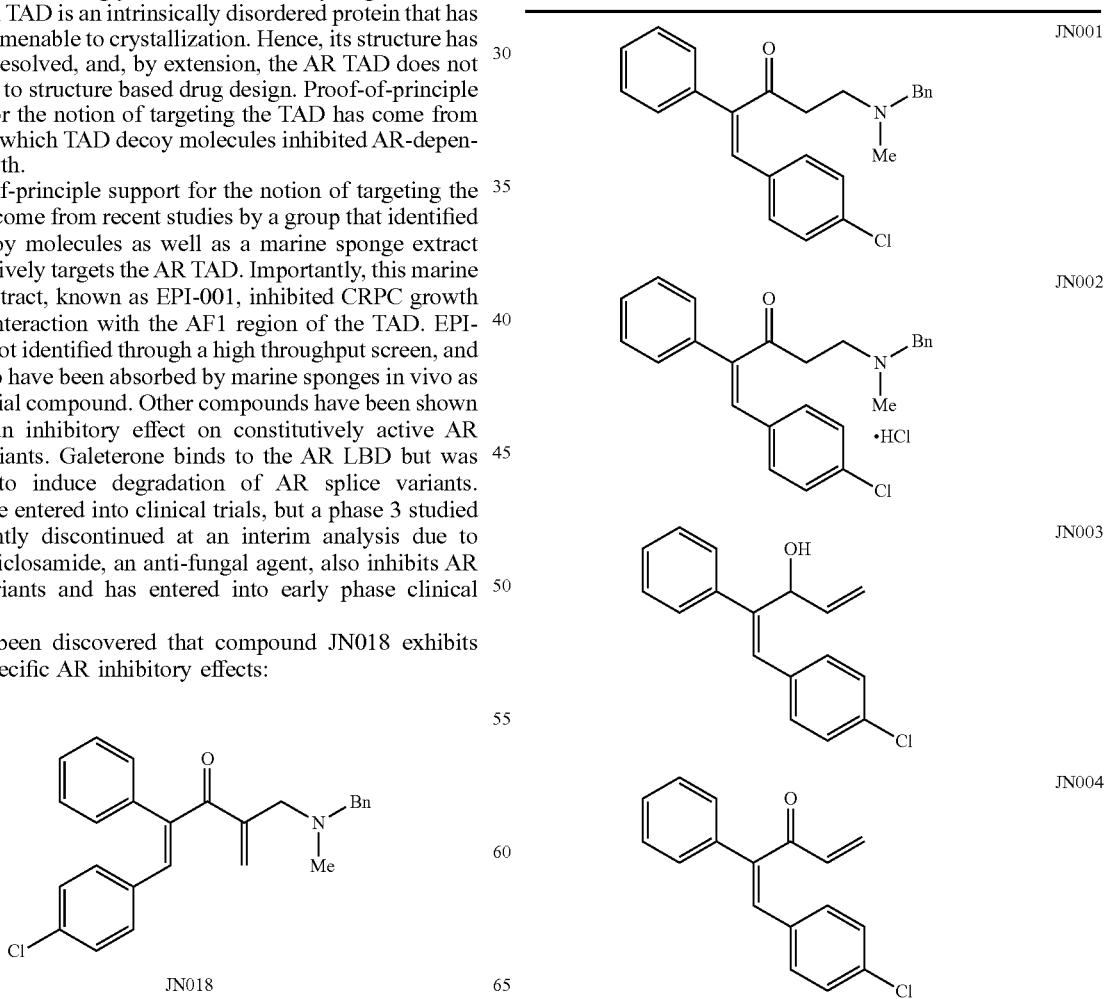

TABLE 1-continued

| Structure | ID |
|---|---|
| 1-(4-chlorophenyl)-2-phenyl-pent-1-en-3-ol | JN005 |
| 1-(4-chlorophenyl)-2-phenyl-5-(pyrrolidin-1-yl)pent-1-en-3-one·HCl | JN006 |
| 1-(4-chlorophenyl)-5-(dimethylamino)-2-phenylpent-1-en-3-one·HCl | JN007 |
| 1-(4-chlorophenyl)-5-(di-n-hexylamino)-2-phenylpent-1-en-3-one·HCl | JN008 |
| 1-(4-chlorophenyl)-5-(4-methylpiperazin-1-yl)-2-phenylpent-1-en-3-one·HCl | JN009 |
| 1-(4-bromophenyl)-2-phenyl-pent-1-en-3-ol | JN010 |
| 1-(4-fluorophenyl)-2-phenyl-pent-1-en-3-ol | JN011 |
| 1-(4-methylphenyl)-2-phenyl-pent-1-en-3-ol | JN012 |
| 1-(4-methylphenyl)-2-phenyl-pent-1-en-3-ol | JN013 |
| 1-(4-methoxyphenyl)-2-phenyl-pent-1-en-3-ol | JN014 |
| 1-(4-bromophenyl)-5-(dimethylamino)-2-phenylpent-1-en-3-one·HCl | JN015 |
| 5-(dimethylamino)-1-(4-methoxyphenyl)-2-phenylpent-1-en-3-one·HCl | JN016 |

TABLE 1-continued

| Structure | ID |
|---|---|
| (4-Cl-C6H4)CH=C(C(O)Ph)(CH2N(Me)Bn) | JN017 |
| (4-Cl-C6H4)CH=C(CH2N(Bn)Me)C(O)Ph · HCl | JN019 |
| (3-Br-C6H4)CH=C(CH2N(Bn)Me)C(O)Ph · HCl | JN020 |
| (4-Br-C6H4)CH=C(CH2N(Bn)Me)C(O)Ph · HCl | JN021 |
| (4-Br-C6H4)CH=C(C(O)Ph)(CH2N(Me)Bn) | JN022 |
| (4-Cl-C6H4)CH=C(CH2NMe2)C(O)Ph · HCl | JN023 |
| (4-Cl-C6H4)CH=C(C(O)Ph)(CH2NMe2) | JN024 |
| (4-Cl-C6H4)CH=C(C(O)C(=CH2)Me)Ph | JN025 |
| (4-Cl-C6H4)CH=C(Me)C(O)Ph | JN026 |
| (4-Cl-C6H4)CH=C(C(O)Ph)(CH2N(nHx)2) | JN027 |
| (4-Cl-C6H4)CH=C(C(O)Ph)(CH2-pyrrolidinyl) | JN028 |
| (4-Cl-C6H4)CH=C(C(O)Ph)(CH2-morpholinyl) | JN029 |
| (4-F-C6H4)CH=C(C(O)Ph)(CH2N(Bn)Me) | JN030 |

TABLE 1-continued
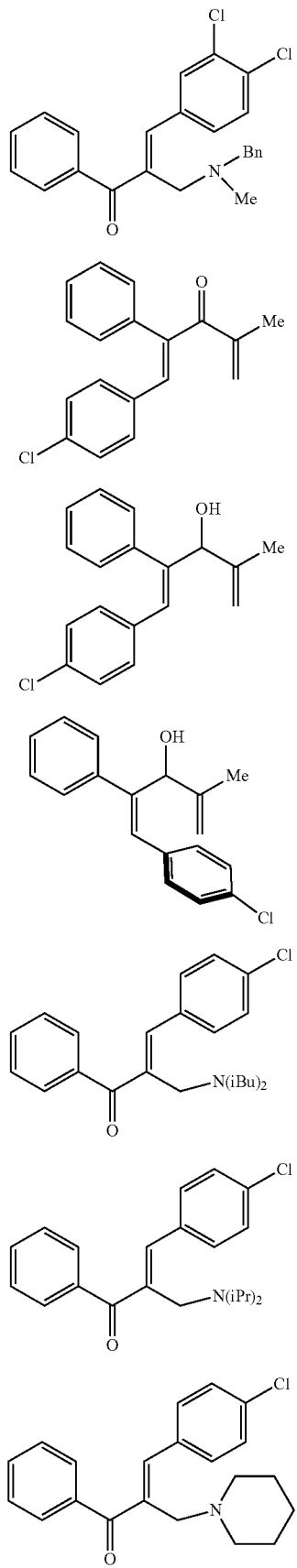
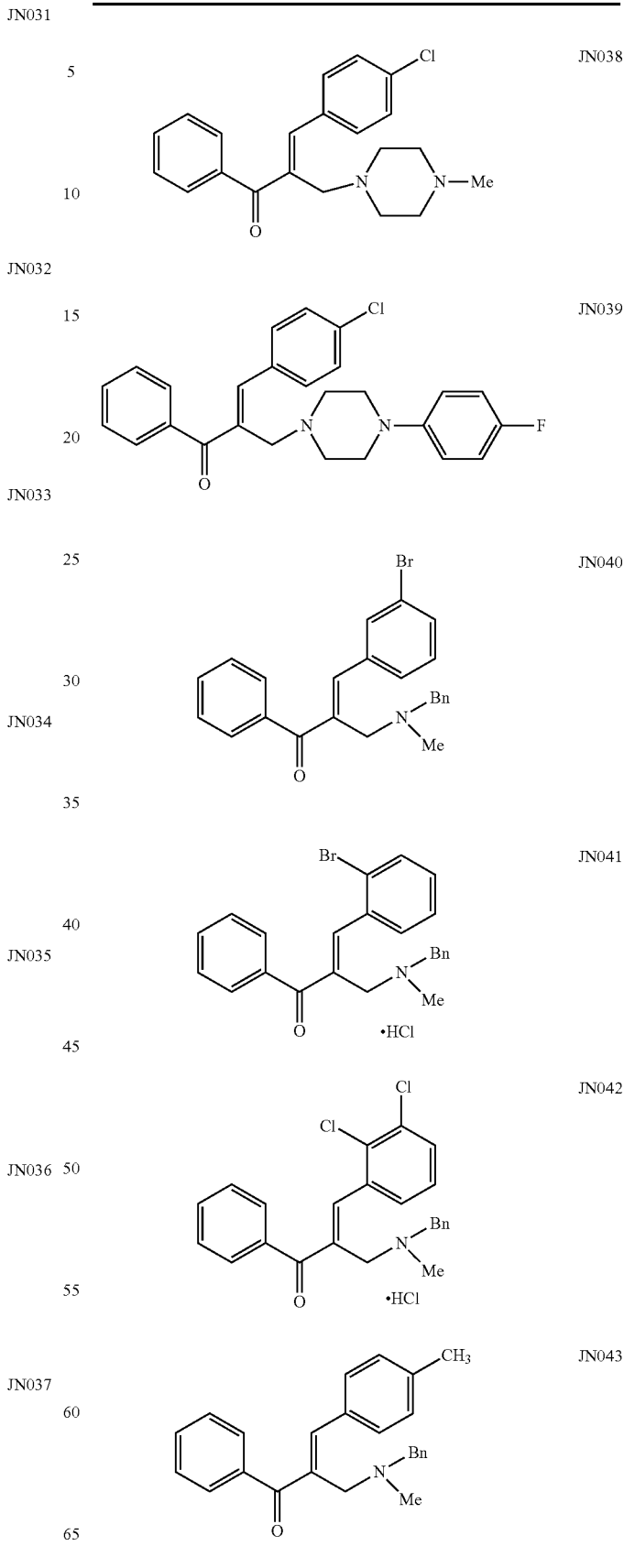

TABLE 1-continued
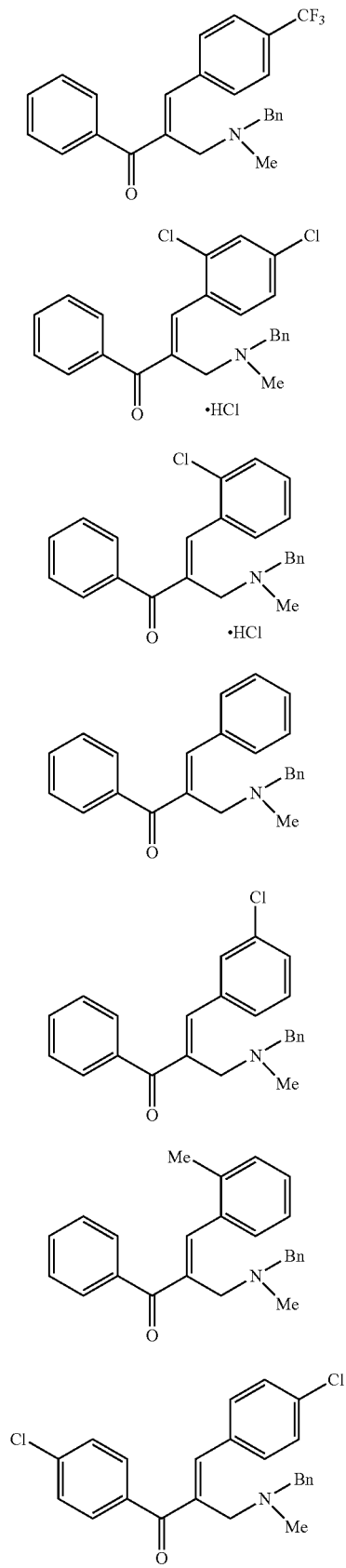
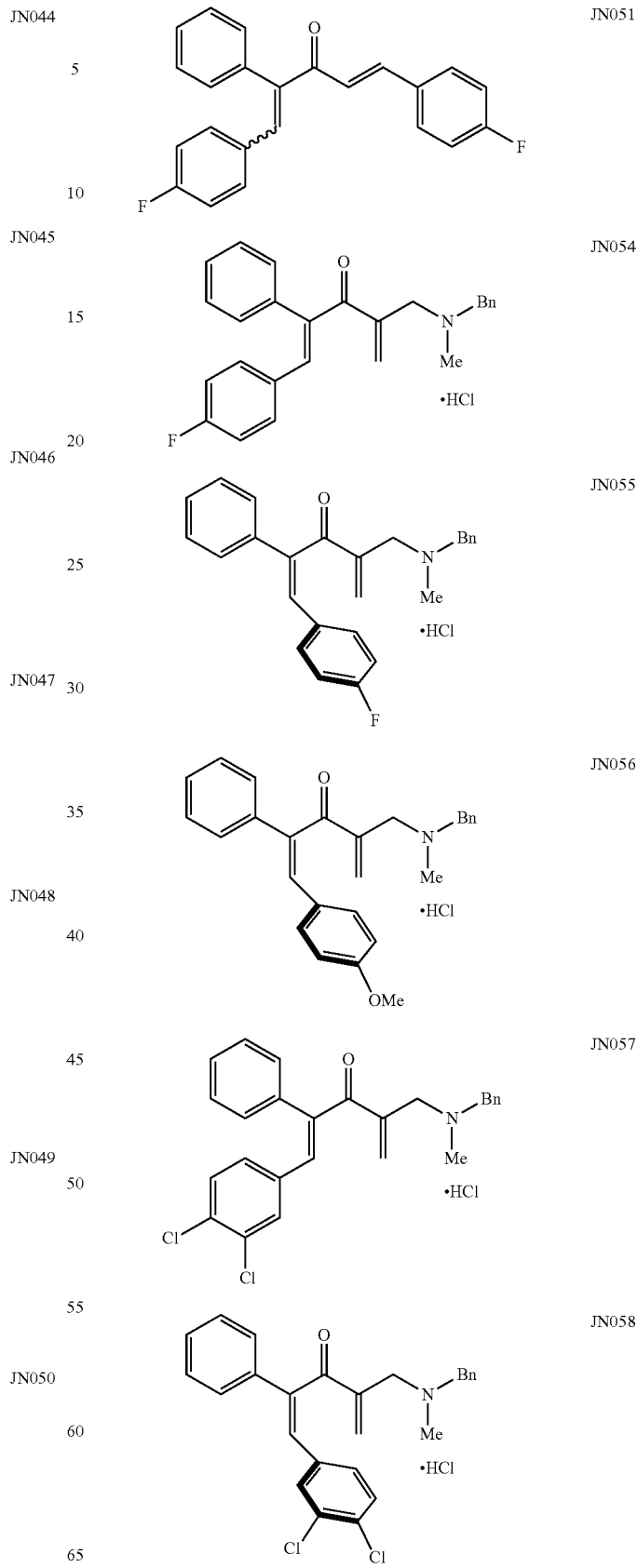

TABLE 1-continued

| Structure | ID |
|---|---|
| (2-Cl-phenyl CH=C(Ph)-C(O)-C(=CH2)-CH2-N(Me)Bn) · HCl | JN059 |
| (3-Cl-phenyl CH=C(Ph)-C(O)-C(=CH2)-CH2-N(Me)Bn) · HCl | JN060 |
| (2-furyl CH=C(Ph)-C(O)-C(=CH2)-CH2-N(Me)Bn) · HCl | JN061 |
| (Ph CH=C(Ph)-C(O)-C(=CH2)-CH2-N(Me)Bn) · HCl | JN062 |
| (Ph CH=C(Ph)-C(O)-C(=CH2)-CH2-N(Me)Bn) · HCl | JN063 |
| (4-CF3-phenyl CH=C(Ph)-C(O)-C(=CH2)-CH2-N(Me)Bn) · HCl | JN064 |
| (3-CF3-phenyl CH=C(Ph)-C(O)-C(=CH2)-CH2-N(Me)Bn) · HCl | JN065 |
| (4-Me-phenyl CH=C(Ph)-C(O)-C(=CH2)-CH2-N(Me)Bn) · HCl | JN066 |
| (3-Me-phenyl CH=C(Ph)-C(O)-C(=CH2)-CH2-N(Me)Bn) · HCl | JN067 |
| (3,5-diCl-phenyl CH=C(Ph)-C(O)-C(=CH2)-CH2-N(Me)Bn) · HCl | JN068 |
| (3-F-phenyl CH=C(Ph)-C(O)-C(=CH2)-CH2-N(Me)Bn) · HCl | JN069 |
| (3-Br-phenyl CH=C(Ph)-C(O)-C(=CH2)-CH2-N(Me)Bn) · HCl | JN070 |

TABLE 1-continued
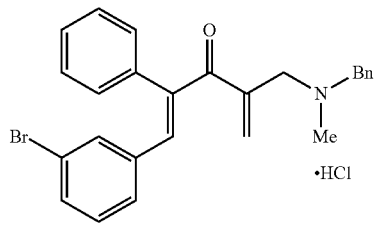 [SMILES: C=C(CN(C)Cc1ccccc1)C(=O)/C(=C/c1cccc(Br)c1)c1ccccc1 ; Cl] JN071
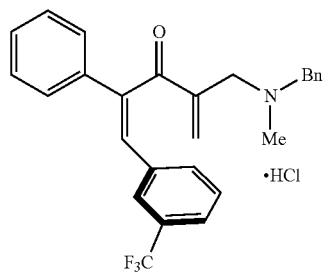 JN072
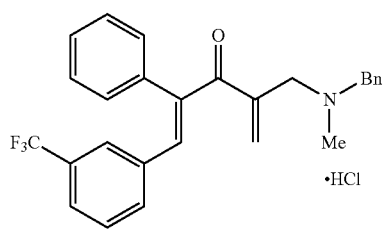 [SMILES: C=C(CN(C)Cc1ccccc1)C(=O)/C(=C/c1cccc(C(F)(F)F)c1)c1ccccc1 ; Cl] JN073
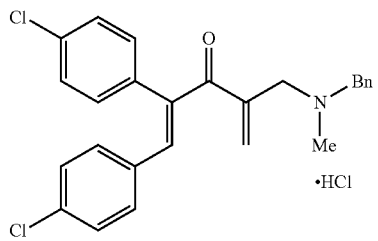 [SMILES: C=C(CN(C)Cc1ccccc1)C(=O)/C(=C/c1ccc(Cl)cc1)c1ccc(Cl)cc1 ; Cl] JN074
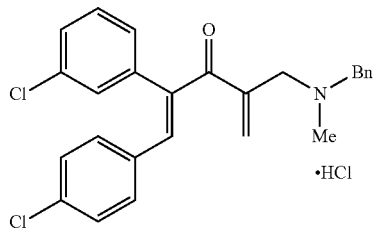 [SMILES: C=C(CN(C)Cc1ccccc1)C(=O)/C(=C/c1ccc(Cl)cc1)c1cccc(Cl)c1 ; Cl] JN075
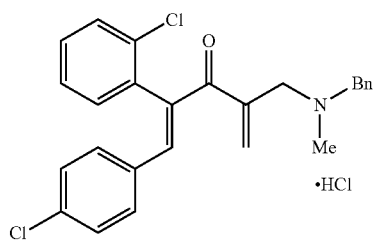 [SMILES: C=C(CN(C)Cc1ccccc1)C(=O)/C(=C/c1ccc(Cl)cc1)c1ccccc1Cl ; Cl] JN076
TABLE 1-continued
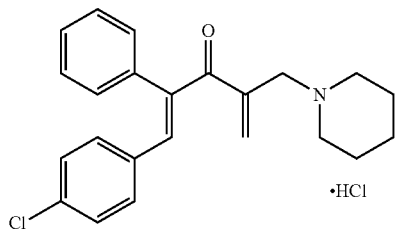 [SMILES: C=C(CN1CCCCC1)C(=O)/C(=C/c1ccc(Cl)cc1)c1ccccc1 ; Cl] JN077
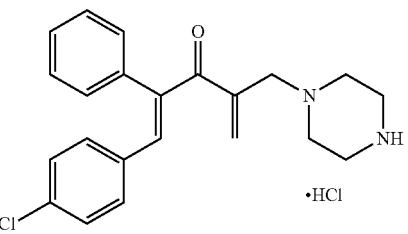 [SMILES: C=C(CN1CCNCC1)C(=O)/C(=C/c1ccc(Cl)cc1)c1ccccc1 ; Cl] JN078
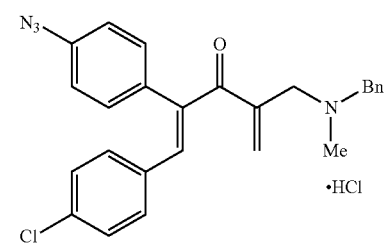 [SMILES: C=C(CN(C)Cc1ccccc1)C(=O)/C(=C/c1ccc(Cl)cc1)c1ccc(N=[N+]=[N-])cc1 ; Cl] JN079
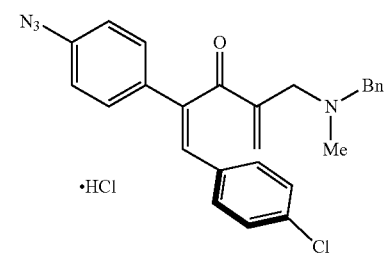 JN080
 JN081
JN082

TABLE 1-continued
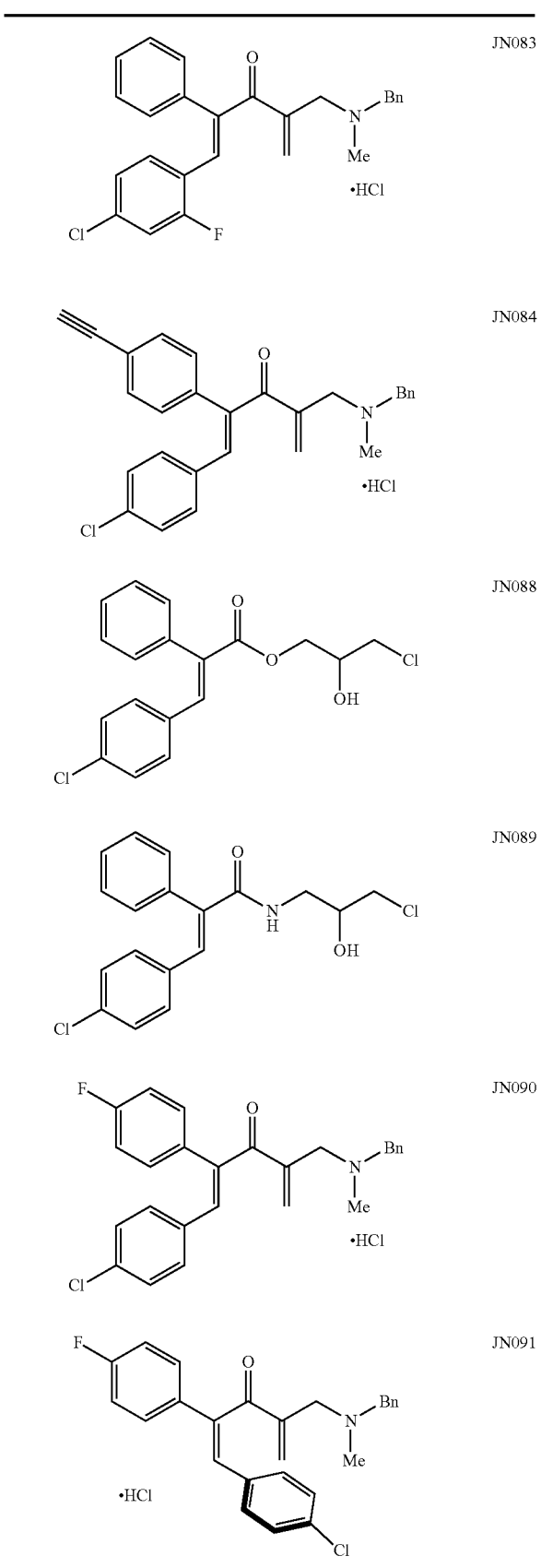
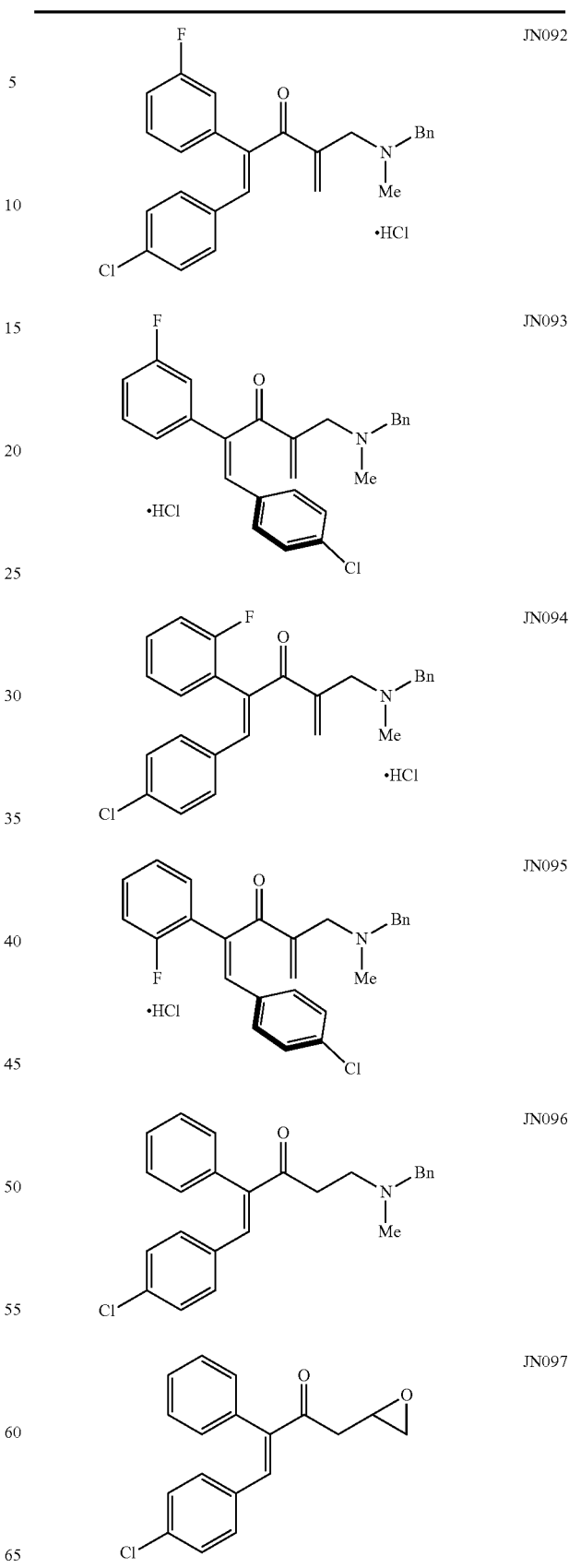

TABLE 1-continued
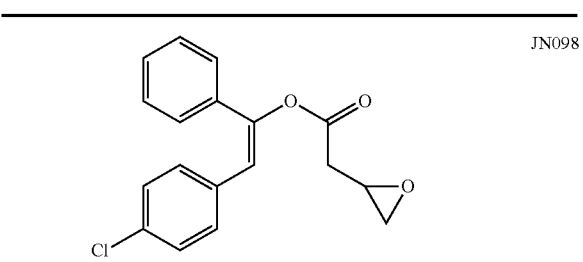 JN098
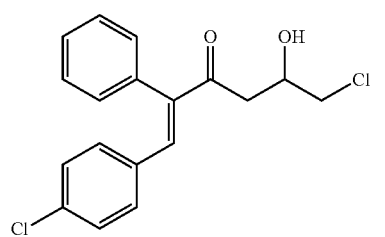 [SMILES: O=C(CC(O)CCl)/C(=C/c1ccc(Cl)cc1)c1ccccc1] JN099
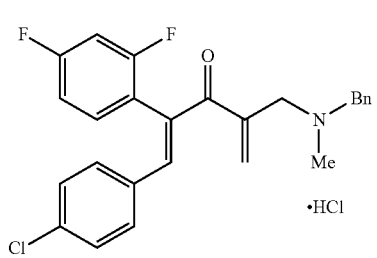 [SMILES: C=C(CN(C)Cc1ccccc1)C(=O)/C(=C/c1ccc(Cl)cc1)c1ccc(F)cc1F ; Cl] JN100
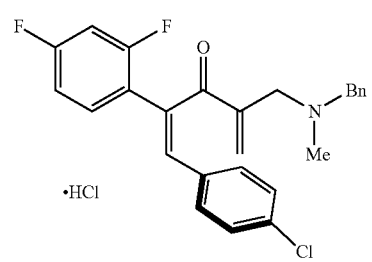 JN101
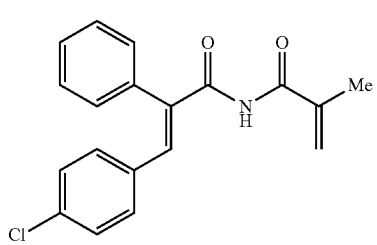 [SMILES: C=C(C)C(=O)NC(=O)/C(=C/c1ccc(Cl)cc1)c1ccccc1] JN102
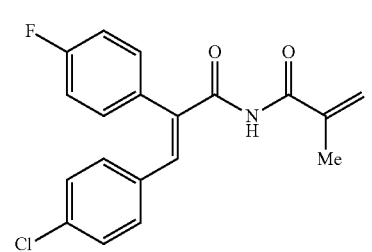 [SMILES: C=C(C)C(=O)NC(=O)/C(=C/c1ccc(Cl)cc1)c1ccc(F)cc1] JN103
TABLE 1-continued
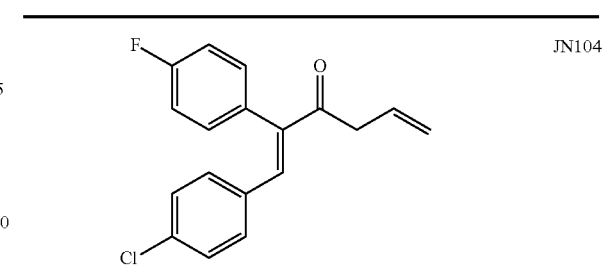 JN104
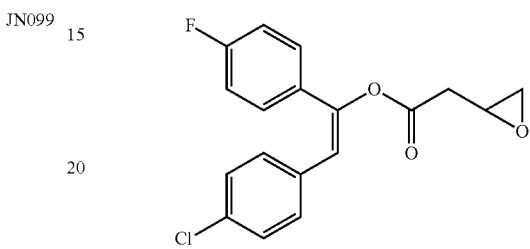 JN105
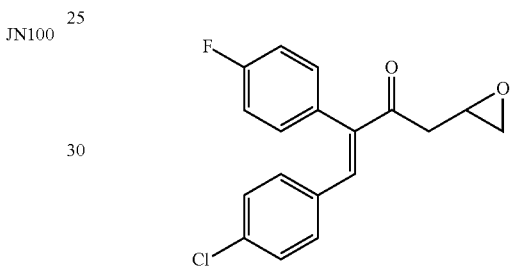 JN106
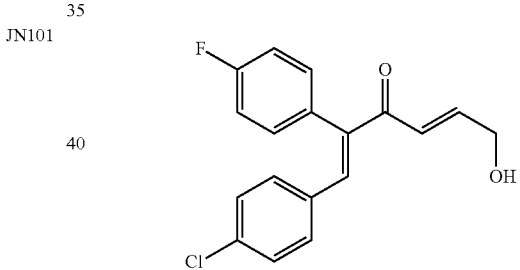 JN107
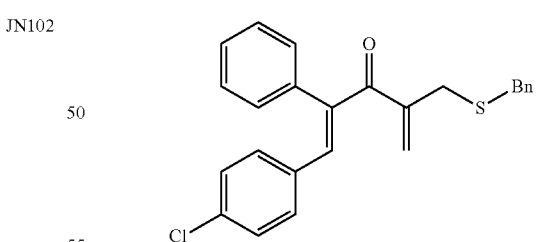 JN108
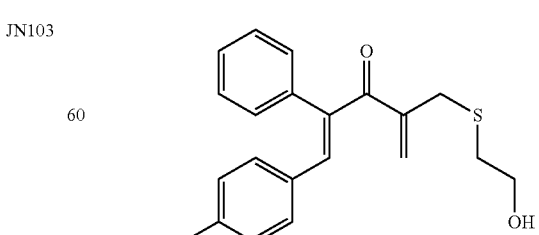 JN109

TABLE 1-continued
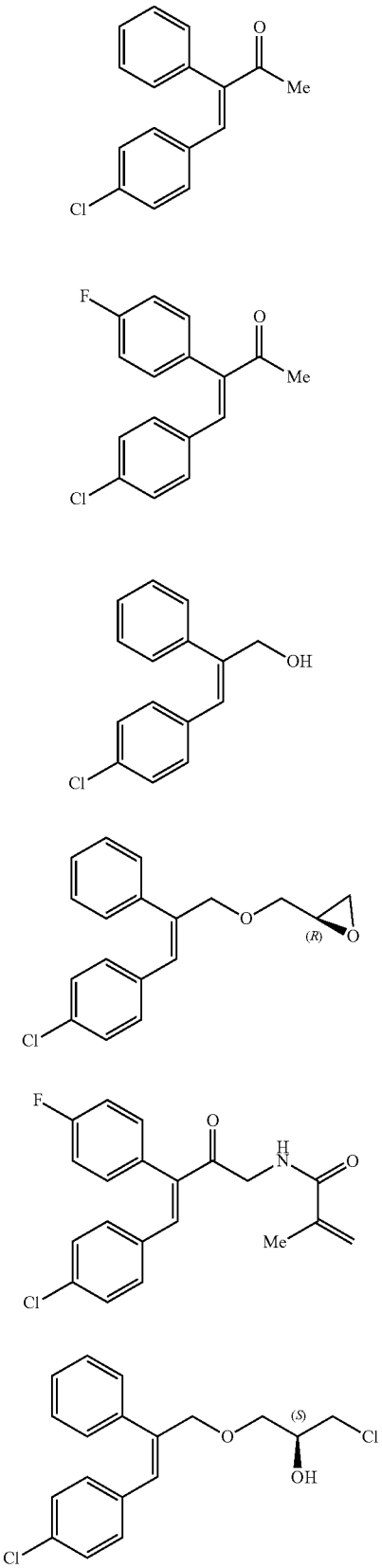
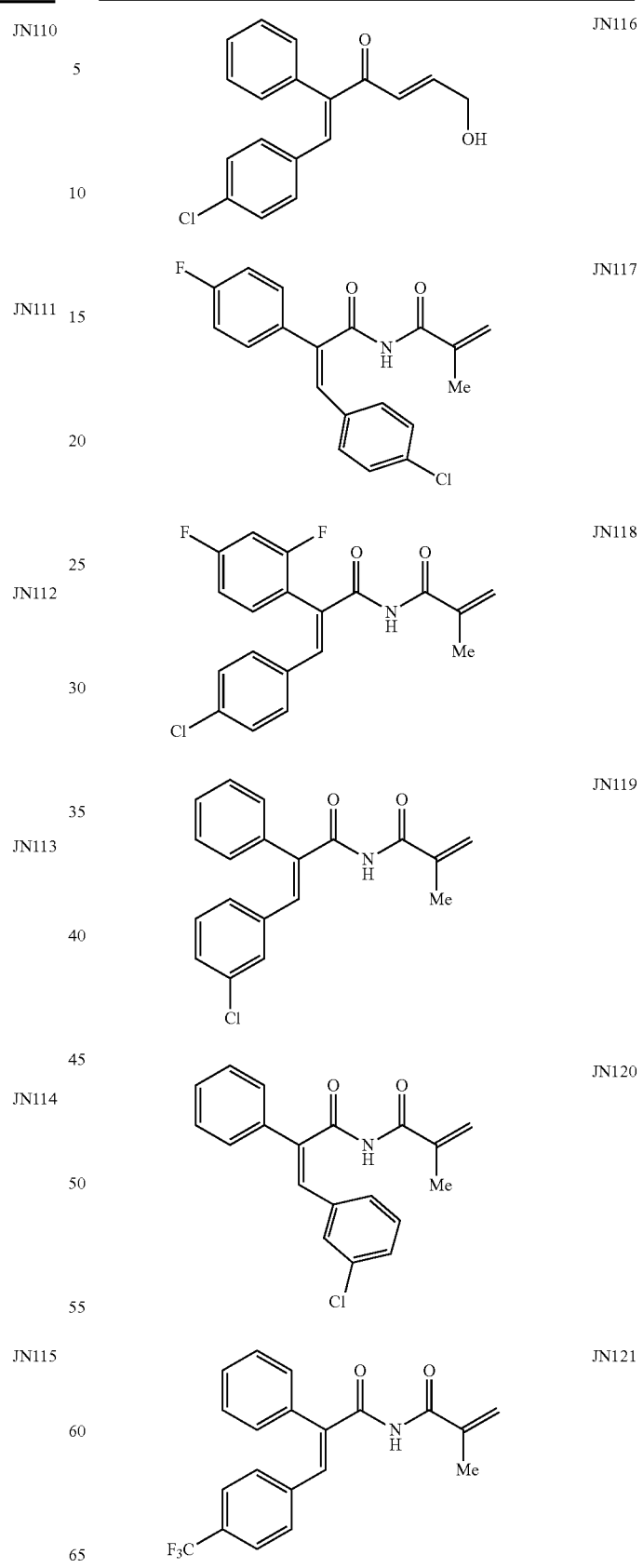

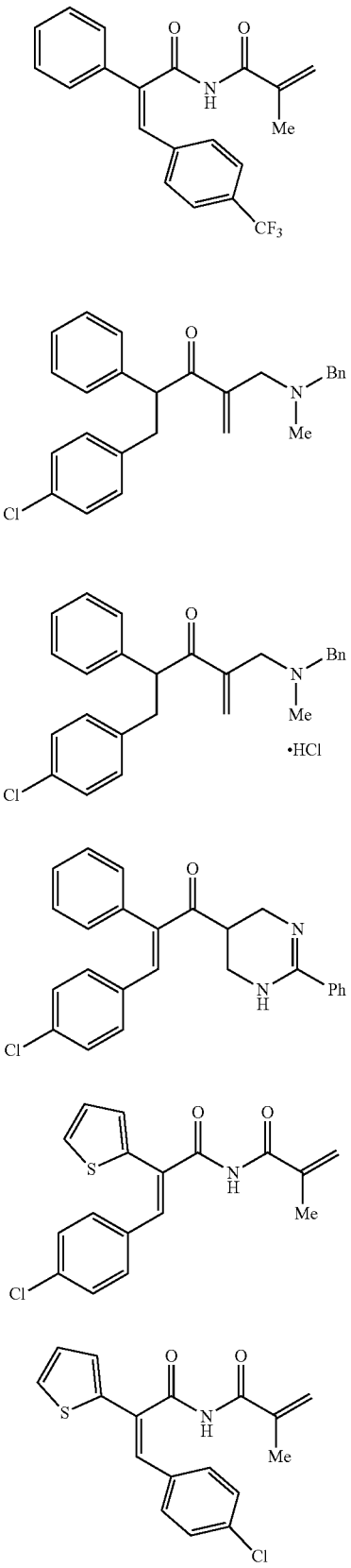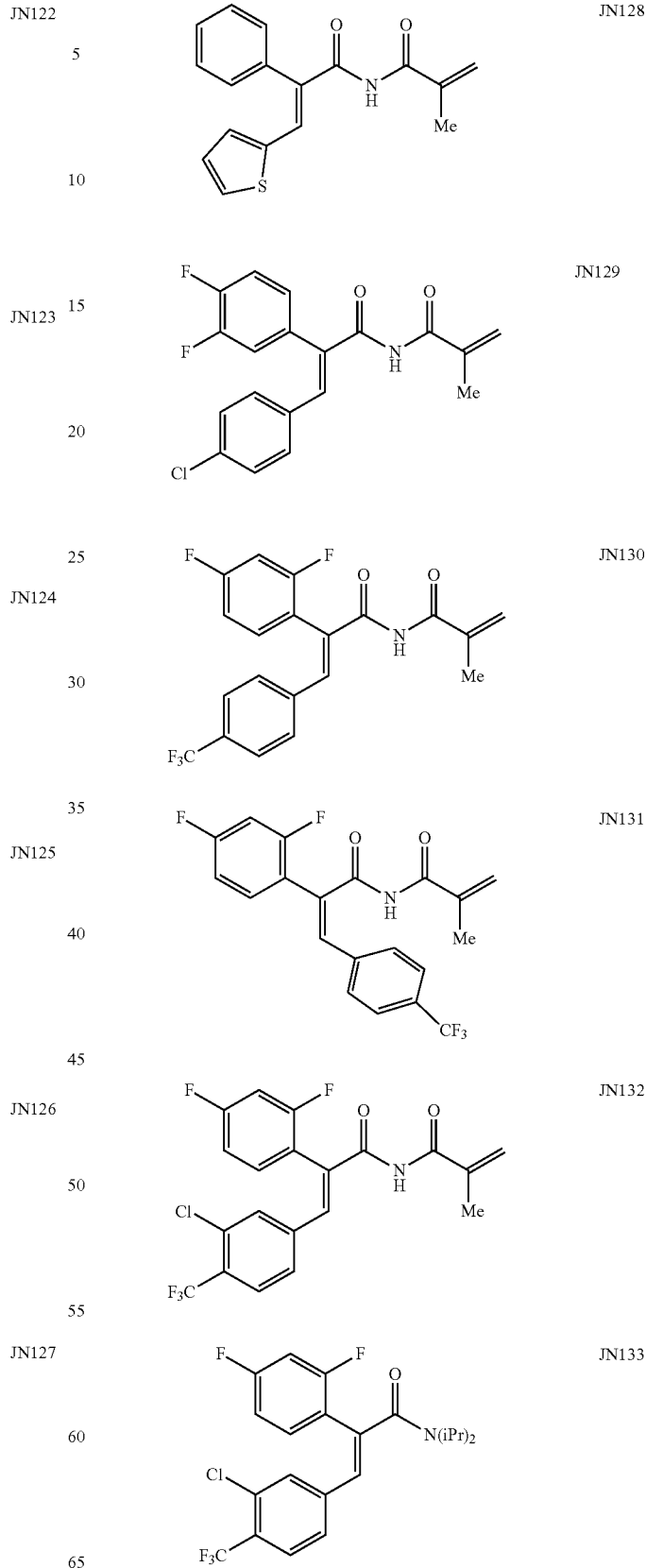

TABLE 1-continued

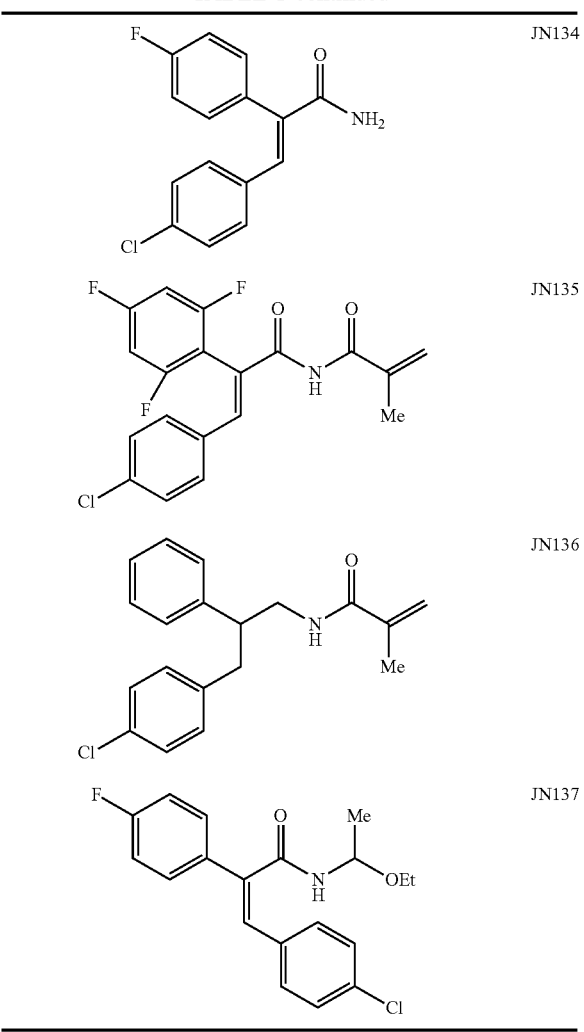

The compounds disclosed herein are believed to the first AR degraders that directly target the TAD. By eliminating the AR and its splice variants, these compounds offer the promise of overcoming AR-dependent castration resistance irrespective of the underlying molecular mechanism(s), including but not limited to the expression of constitutively active ARSVs that lack a functional C-terminal LBD.

In certain aspects, the present disclosure comprises a compound of the disclosure and a pharmaceutically acceptable excipient.

EXAMPLES

The invention now being generally described, it will be more readily understood by reference to the following examples, which are included merely for purposes of illustration of certain aspects and embodiments of the present invention, and are not intended to limit the invention.

Example 1: Exemplary Synthesis of Compounds of the Disclosure

General Materials and Methods

All solvents and reagents were purchased from commercial sources and used without further purification unless otherwise noted. Acetonitrile (MeCN), toluene (calcium hydride), dichloromethane (DCM), diethyl ether (EtO$_2$), and tetrahydrofuran (THF) used for the reactions were dried by distillation over calcium hydride (MeCN, toluene, DCM) or sodium (EtO$_2$, THF). All reactions were performed under an inert atmosphere of dry argon and monitored by thin layer chromatography (TLC) on pre-coated EMD silica gel 60 F$_{254}$ TLC aluminum sheets and visualized with a UV lamp. Flash column chromatography was performed on SiliaFlash P60 (SiliCycle Inc.) silica gel (40-63 m, 60 Å pore size). NMR spectra were obtained on Bruker AV400 and AV500 instruments at the UCLA MIC Magnetic Resonance Laboratory. NMR data were analyzed using the MestReNova NMR software (Mestrelab Research S. L., version 11.0.2). Chemical shifts (δ) are expressed in ppm and are internally referenced for $^1$H NMR (CHCl$_3$ 7.26 ppm, DMSO-d$_6$ 2.50 ppm) and $^{13}$C NMR (CDCl$_3$ 77.16 ppm, DMSO-d$_6$ 39.52 ppm). DART-MS spectra were collected on a Thermo Exactive Plus MSD (Thermo Scientific) equipped with an ID-CUBE ion source and a VAPUR Interface (IonSense). Both the source and MSD were controlled by Excalibur, version 3.0. The analyte was spotted onto OpenSpot sampling cards (IonSense) using DCM or chloroform as the solvent. Ionization was accomplished using He plasma with no additional ionization agents. Melting points were recorded on a Büchi® B-545 melting point apparatus. Analytical HPLC was performed on a 2.0×50 mm Waters Corp. 1.5 m C18 analytical HPLC column. A linear gradient of mobile phase was used over 5 min from 5-95% MeCN/water containing 0.2% HCOOH. The flow rate was 0.4 mL/min and the peaks were detected by a LCT-Premier ESI-TOF mass spectrometer in the positive ion mode.

Synthesis

Scheme 1: Synthesis of ketone 3.

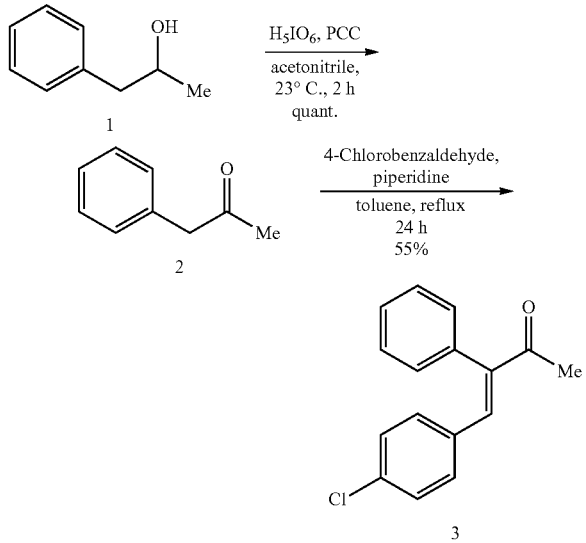

Phenylacetone (2)

Periodic acid (21.50 g, 92.4 mmol, 1.1 eq) was added to MeCN (250 mL) while stirring at 23° C., and the suspension stirred vigorously for 15 min. Then the flask was placed in an ice-bath and 1, 1-phenyl-2-propanol, (12.0 mL, 84.0 mmol, 1.0 eq) was added. To this cooled solution was added pyridinium chlorochromate (370.1 mg, 1.7 mmol, 0.02 eq) in MeCN (60 mL), dropwise over 5 min. The resultant creamy yellow suspension was stirred at 0° C. for 1 h and at 23° C. for 1 h. Then the reaction mixture was diluted with ethyl acetate (EtOAc) (300 mL) and washed with a mixture of brine/water (1:1, 200 mL). The organic layer was then washed with a saturated solution of $Na_2SO_3$ (200 mL×2) and brine (200 mL), dried over anhydrous $MgSO_4$, filtered, and the solvent removed in vacuo to obtain 2, 1-phenylacetone, (11.2 g, 83.5 mmol, quantitative) as a yellow oil. $R_f$ 0.24 (10% EtOAc/hexanes); $^1$H NMR (400 MHz, $CDCl_3$) δ 7.36-7.31 (m, 2H), 7.30-7.24 (m, 1H), 7.23-7.18 (m, 2H), 3.69 (s, 2H), 2.14 (s, 3H); $^{13}$C NMR (101 MHz, $CDCl_3$) δ 206.35, 134.32, 129.44, 128.79, 127.09, 51.04, 29.29.

(E)-4-(4-Chlorophenyl)-3-phenylbut-3-en-2-one (3)

To a solution of phenylacetone 2 (5.0 g, 37.3 mmol, 1.0 eq) and 4-chlorobenzaldehyde (5.32 g, 37.3 mmol, 1.0 eq) in toluene (120 mL) was added piperidine (0.15 mL, 1.5 mmol, 0.04 eq), and the resultant mixture heated at reflux for 24 h. Then the solvent was removed in vacuo and the residue purified by column chromatography using a mobile phase gradient of 0 to 10% EtOAc/hexanes to yield the diarylenone 3 (5.3 g, 20.6 mmol, 55%) as an off-white solid. Rf 0.18 (10% EtOAc/hexanes); 1H NMR (500 MHz, CDCl3) δ 7.58 (s, 1H), 7.45-7.35 (m, 3H), 7.16 (dd, J=7.8, 1.7 Hz, 2H), 7.13 (d, J=8.6 Hz, 2H), 6.95 (d, J=8.5 Hz, 2H), 2.29 (s, 3H); 13C NMR (126 MHz, CDCl3) δ 199.25, 141.40, 137.37, 136.74, 135.26, 133.22, 132.11, 129.52, 129.33, 128.68, 128.27, 28.15.

Scheme 2: Sythesis of the diaryldienone 4.

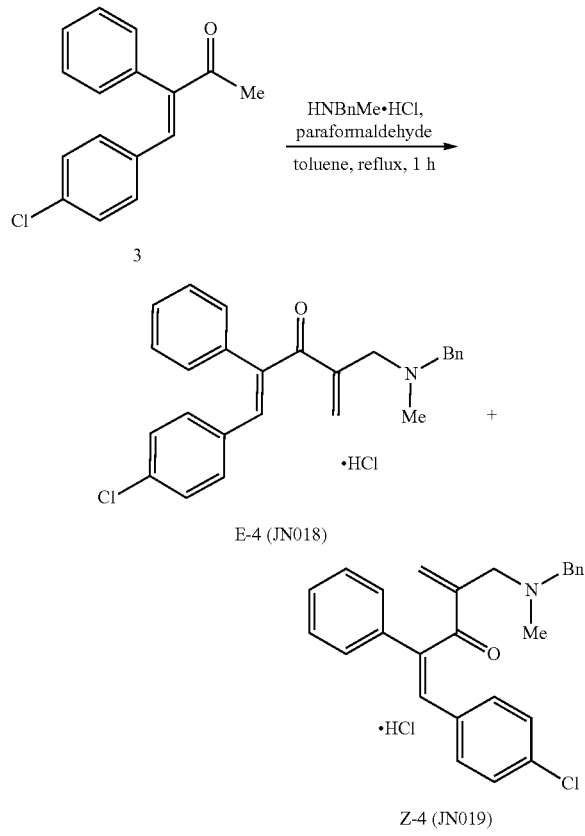

(E)-4-((Benzyl(methyl)amino)methyl)-1-(4-chlorophenyl)-2-phenylpenta-1,4-dien-3-one hydrochloride (E-4, JN018)

The enone 3 (300.0 mg, 1.2 mmol, 1.0 eq), paraformaldehyde (222.9 mg, 7.2 mmol, 6.0 eq), and N-benzylmethylamine hydrochloride (405.3 mg, 2.6 mmol, 2.2 eq) were dissolved in toluene (3 mL) and heated at reflux for 1 h. Then the reaction was quenched with the addition of 1 mL of 10% $Na_2CO_3$ (aq) while stirring. The solution was then partitioned between $EtO_2$ (5 mL) and 10% $Na_2CO_3$ (aq, 6 mL). The layers were separated and the aqueous layer was extracted with further $EtO_2$ (4 mL×2). The combined organic layers were washed with brine (5 mL), dried over anhydrous $MgSO_4$, filtered, and concentrated in vacuo. The residue was purified by column chromatography on silica gel buffered with 1% triethylamine in hexanes, using a mobile phase gradient of 3:100 to 15:100 mL of $EtO_2$/hexanes to yield the free base of E-4 as a yellow colored oil (330.9 mg, 0.82 mmol). $R_f$ 0.18 (20% $EtO_2$/hexanes on silica buffered with 1% triethylamine in hexanes); $^1$H NMR (400 MHz, $CDCl_3$) δ 7.35-7.31 (m, 3H), 7.29 (m, 4H), 7.23 (m, 2H), 7.21-7.16 (m, 2H), 7.13 (d, J=8.6 Hz, 2H), 6.96 (d, J=8.4 Hz, 2H), 5.86 (q, J=1.3 Hz, 1H), 5.84 (q, J=1.2 Hz, 1H), 3.54 (s, 2H), 3.31 (t, J=1.2 Hz, 2H), 2.19 (s, 3H); $^{13}$C NMR (101 MHz, $CDCl_3$) δ 198.62, 146.81, 141.50, 139.18, 137.53, 136.13, 134.80, 133.48, 131.65, 129.69, 128.93 (2C), 128.61, 128.34, 128.19, 127.09, 124.96, 62.07, 59.30, 42.46.

A small amount of the Z-isomer of the free base 4 (Z-4) was also obtained in this reaction as described below.

The free base of E-4 above was dissolved in DCM (7 mL) and shaken vigorously with 1 N HCl (aq, 5 mL) to form the hydrochloride salt. The aqueous layer was extracted with further DCM (5 mL×2). The combined organic layers were dried over anhydrous $MgSO_4$, filtered, and concentrated in vacuo to yield the diaryldienone hydrochloride E-4 (327.0 mg, 0.75 mmol, 62% from 3) as a white solid.

Melting point 165.8-166.0° C.; $^1$H NMR (400 MHz, $CDCl_3$) δ 12.78 (m, 1H), 7.66 (m, 2H), 7.49-7.43 (m, 3H), 7.40 (s, 1H), 7.37 (m, 3H), 7.19-7.14 (m, 4H), 7.12 (s, 1H), 7.04 (d, J=8.6 Hz, 2H), 6.60 (s, 1H), 4.28 (dd, J=13.1, 4.8 Hz, 1H), 4.18 (dd, J=13.1, 5.4 Hz, 1H), 4.00 (dd, J=13.1, 4.4 Hz, 1H), 3.93 (dd, J=13.1, 6.8 Hz, 1H), 2.65 (d, J=4.8 Hz, 3H); $^{13}$C NMR (101 MHz, $CDCl_3$) δ 196.80, 139.80, 139.51, 138.43, 136.63, 135.65, 135.56, 132.63, 131.99, 131.52, 130.44, 129.62, 129.37, 129.30, 128.83, 128.73, 128.48, 60.37, 53.94, 39.65; HRMS m/z calcd. for $C_{26}H_{25}ClNO$ [M+H]$^+$ 402.16192, found 402.16098; Analytical HPLC $t_R$=3.45 min.

(Z)-4-((Benzyl(methyl)amino)methyl)-1-(4-chlorophenyl)-2-phenylpenta-1,4-dien-3-one hydrochloride (Z-4, JN019)

The free base of Z-4 was isolated from the same reaction that generated the free base of E-4 above, as an orange colored oil (108.8 mg, 0.27 mmol). $R_f$ 0.32 (20% $EtO_2$/hexanes on silica buffered with 1% triethyamine in hexanes); $^1$H NMR (400 MHz, $CDCl_3$) δ 7.43-7.38 (m, 2H), 7.38-7.34 (m, 3H), 7.34-7.25 (m, 5H), 7.20 (s, 4H), 7.02 (s, 1H), 6.19 (d, J=1.2 Hz, 1H), 6.11 (d, J=1.4 Hz, 1H), 3.49 (s, 2H), 3.29 (t, J=1.3 Hz, 2H), 2.06 (s, 3H); $^{13}$C NMR (126 MHz, $CDCl_3$) δ 200.85, 145.50, 141.91, 139.31, 138.17, 134.48, 133.97, 130.95, 130.11, 128.95, 128.85, 128.80, 128.56, 128.47, 128.35, 127.10, 126.42, 62.51, 56.29, 42.31.

The free base above was converted to the hydrochloride using the procedure outlined for E-4, to obtain the diaryldienone hydrochloride Z-4 (96.4 mg, 0.0.22 mmol, 18% from 3) as a white solid. $^1$H NMR (500 MHz, CDCl$_3$) δ 12.62 (m, 1H), 7.59 (m, 2H), 7.48-7.41 (m, 3H), 7.40-7.29 (m, 6H), 7.22 (d, J=8.2 Hz, 2H), 7.13 (m, 3H), 6.71 (s, 1H), 4.16 (dd, J=13.5, 3.9 Hz, 1H), 4.01 (dd, J=13.0, 5.1 Hz, 1H), 3.90 (d, J=6.0 Hz, 2H), 2.47 (d, J=3.6 Hz, 3H); $^{13}$C NMR (126 MHz, CDCl$_3$) δ 199.43, 141.78, 140.66, 137.01, 136.97, 134.66, 134.16, 131.43, 130.39, 130.11, 129.86, 129.58, 129.32, 129.10 (2C), 128.34, 126.22, 60.10, 51.44, 39.08; HRMS m/z calcd. for C$_{26}$H$_{25}$ClNO [M+H]$^+$ 402.16192, found 402.16128.

Scheme 3: Synthesis of the Z-diarylenones JN001 and JN002.

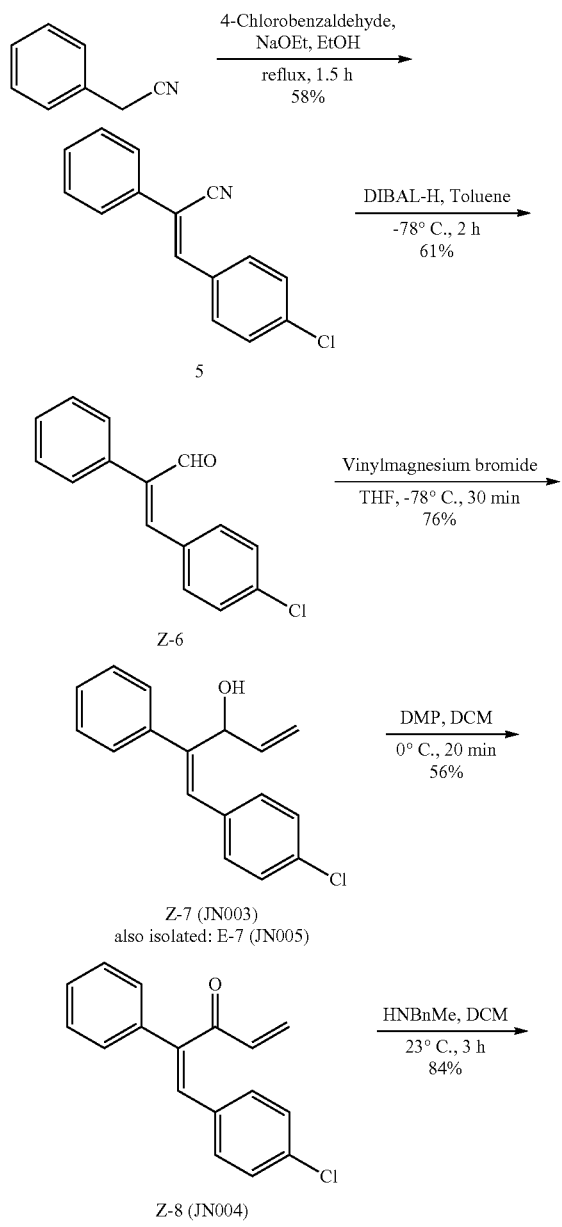

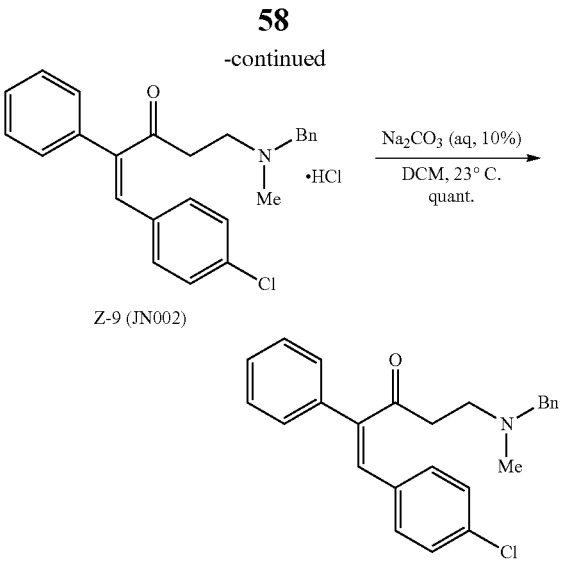

(Z)-3-(4-Chlorophenyl)-2-phenylacrylonitrile (5)

To a mixture of benzyl cyanide (10.0 mL, 84.9 mmol, 1.0 eq) and 4-chlorobenzaldehyde (12.1 g, 84.9 mmol, 1.0 eq) in absolute ethanol at 23° C. was added a freshly prepared solution of sodium ethoxide in ethanol (100 mL of a 1.27 M solution, 127.0 mmol, 1.5 eq). The resultant mixture was heated at reflux for 1.5 h, and then gradually cooled to 0° C. The resultant precipitate was filtered, washed with ice-cold absolute ethanol, and dried in vacuo to yield the acrylonitrile 5 (11.9 g, 49.6 mmol, 58%) as a white solid. $^1$H NMR (400 MHz, CDCl$_3$) δ 7.83 (d, J=8.5 Hz, 2H), 7.70-7.65 (m, 2H), 7.50-7.40 (m, 6H); $^{13}$C NMR (101 MHz, CDCl$_3$) δ 140.76, 136.57, 134.28, 132.29, 130.60, 129.56, 129.38, 129.26, 126.13, 117.87, 112.43.

(Z)-3-(4-Chlorophenyl)-2-phenylacrylaldehyde (Z-6)

To a cooled (−78° C.) solution of the acrylonitrile 5 (10.0 g, 41.7 mmol, 1.0 eq) in toluene was added a 1.0 M solution of DIBAL-H (43.8 mL, 43.8 mmol, 1.05 eq). The resultant suspension was stirred for 2 h at −78° C. The reaction was quenched by the addition of 5 mL of 5% H$_2$SO$_4$ (aq) at −78° C., and the reaction allowed to warm to 0° C. while stirring. To this was added a further 5% H$_2$SO$_4$ (aq, 145 mL) and Et$_2$O (100 mL), and the mixture stirred vigorously for 30 min at 0° C. After separating the layers, the aqueous layer was extracted with Et$_2$O (150 mL×2). The combined organic layers were washed with brine (300 mL), dried over anhydrous MgSO$_4$, filtered, and concentrated in vacuo. The crude material was purified by column chromatography on silica gel, using a mobile phase gradient of 0 to 5% of EtOAc/hexanes to yield the enal Z-6 (6.2 g, 25.6 mmol, 61%) as a pale yellow solid. R$_f$ 0.52 (10% EtOAc/hexanes); $^1$H NMR (400 MHz, CDCl$_3$) δ 10.09 (s, 1H), 7.78 (s, 1H), 7.45-7.37 (m, 7H), 7.37-7.34 (m, 2H); $^{13}$C NMR (101 MHz, CDCl$_3$)

δ 191.80, 145.52, 141.73, 136.08, 135.97, 132.57, 131.64, 128.99, 128.86, 128.71, 128.56.

(Z)-1-(4-Chlorophenyl)-2-phenylpenta-1,4-dien-3-ol (Z-7, JN003)

A solution of the enal Z-6 (5.78 g, 23.9 mmol, 1.0 eq) in THF (75 mL) was cooled to −78° C. To this was added a solution of vinylmagnesium bromide (32.9 mL of a 0.80 M solution in THF, 26.3 mmol, 1.1 eq) and the reaction left to stir for 30 min at −78° C. To this mixture was added saturated $NH_4Cl$ (aq, 2 mL) and the mixture allowed to warm to 0° C. The contents were then partitioned between saturated $NH_4Cl$ (aq, 145 mL), water (50 mL), and DCM (200 mL). The aqueous layer was further extracted with DCM (150 mL×2). The combined organic layers were washed with brine (200 mL), dried over anhydrous $MgSO_4$, filtered, and concentrated in vacuo. The crude material was purified by column chromatography on silica gel, using a mobile phase gradient of 0 to 10% of EtOAc/hexanes to yield the alcohol Z-7 (4.93 g, 18.2 mmol, 76%) as a pale yellow oil. $R_f$ 0.31 (10% EtOAc/hexanes); $^1$H NMR (400 MHz, $CDCl_3$) δ 7.61-7.56 (m, 2H), 7.42-7.30 (m, 7H), 6.76 (s, 1H), 6.07 (ddd, J=17.2, 10.5, 4.8 Hz, 1H), 5.42 (br tt, J=4.8, 1.8 Hz, 1H), 5.33 (dt, J=17.3, 1.6 Hz, 1H), 5.22 (dt, J=10.5, 1.6 Hz, 1H), 2.28 (d, J=4.9 Hz, 1H); $^{13}$C NMR (101 MHz, $CDCl_3$) δ 143.09, 139.74, 139.26, 135.07, 133.16, 130.38, 130.29, 128.53, 128.47, 128.14, 127.60, 116.06, 70.99; HRMS m/z calcd. for $C_{17}H_{14}ClO$ $[M-H]^-$ 269.07277, found 269.07275.

(E)-1-(4-Chlorophenyl)-2-phenylpenta-1,4-dien-3-ol (E-7, JN005)

A small amount of the E isomer, E-7, was also isolated from the above synthesis of Z-7. $R_f$ 0.17 (10% EtOAc/hexanes); $^1$H NMR (400 MHz, $CDCl_3$) δ 7.38-7.29 (m, 3H), 7.20-7.15 (m, 2H), 7.06 (d, J=8.6 Hz, 2H), 6.86 (d, J=8.6 Hz, 2H), 6.68 (s, 1H), 5.92 (ddd, J=17.1, 10.4, 5.9 Hz, 1H), 5.26 (dt, J=17.2, 1.4 Hz, 1H), 5.17 (dt, J=10.4, 1.3 Hz, 1H), 4.98-4.93 (br m, 1H), 1.92 (d, J=4.2 Hz, 1H); $^{13}$C NMR (101 MHz, $CDCl_3$) δ 144.05, 138.58, 137.93, 135.05, 132.67, 130.61, 129.41, 128.88, 128.24, 127.82, 126.11, 116.18, 77.98; HRMS m/z calcd. for $C_{17}H_{14}Cl$ $[M-OH]^+$ 253.07785, found 253.07655.

(Z)-1-(4-Chlorophenyl)-2-phenylpenta-1,4-dien-3-one (Z-8, JN004)

A solution of the alcohol Z-7 (1.0 g, 3.7 mmol, 1.0 eq) in DCM (30 mL) was cooled in an ice-water bath. To this was added Dess-Martin periodinane (1.7 g, 4.1 mmol, 1.1 eq) and the reaction left to stir for 20 min at 0° C. To this mixture was added a saturated $NaHCO_3$ (aq, 25 mL) and the mixture stirred for 10 min. The contents were then partitioned between DCM (70 mL) and saturated $NaHCO_3$ (aq, 75 mL), and the layers were separated. The organic layer was washed with saturated $NaHCO_3$ (aq, 50 mL×2), dried over anhydrous $MgSO_4$, filtered, and concentrated in vacuo. The crude material was purified by column chromatography on silica gel, using a mobile phase gradient of 0 to 3% of EtOAc/hexanes to yield the dienone Z-8 (560.0 mg, 2.1 mmol, 56%) as a yellow oil. Rr 0.38 (10% EtOAc/hexanes); $^1$H NMR (400 MHz, $CDCl_3$) δ 7.43-7.30 (m, 5H), 7.30-7.22 (m, 4H), 7.07 (s, 1H), 6.41 (dd, J=17.6, 10.3 Hz, 1H), 6.23 (dd, J=17.6, 1.1 Hz, 1H), 5.90 (dd, J=10.3, 1.1 Hz, 1H); $^{13}$C NMR (101 MHz, $CDCl_3$) δ 199.78, 141.57, 137.66, 137.08, 134.25, 134.19, 132.37, 130.21, 129.28, 128.97, 128.87, 128.57, 126.60; HRMS m/z calcd. for $C_{17}H_{14}ClO$ $[M+H]^+$ 269.07277, found 269.07066.

(Z)-5-(Benzyl(methyl)amino)-1-(4-chlorophenyl)-2-phenylpent-1-en-3-one hydrochloride (Z-9, JN002)

To the dienone Z-8 (109.8 mg, 0.41 mmol, 1.05 eq) in DCM (1.5 mL) was added a solution of N-benzylmethylamine (0.78 mL of a 0.50 M solution in DCM, 0.39 mmol, 1.0 eq), and the resultant solution stirred at 23° C. for 3 h. Then the reaction mixture was diluted with 10 mL dichloromethane and shaken with a 1 N solution of HCl (aq, 10 mL). The layers were immediately separated and the aqueous layer extracted with DCM (5 mL×2). The combined organic layers were dried over anhydrous $MgSO_4$, filtered, and volatiles removed in vacuo. The residue was triturated with $Et_2O$ (3×3 mL) and dried in vacuo to yield the β-amino diarylenone hydrochloride salt Z-9 (147.0 mg, 0.34 mmol, 84%) as a white solid. $^1$H NMR (400 MHz, $CDCl_3$) δ 12.74 (m, 1H), 7.51-7.40 (m, 5H), 7.40-7.34 (m, 5H), 7.32 (d, J=8.5 Hz, 2H), 7.22 (d, J=8.4 Hz, 2H), 6.97 (s, 1H), 4.11 (d, J=13.4 Hz, 1H), 3.94 (d, J=12.2 Hz, 1H), 3.41-3.05 (m, 4H), 2.46 (s, 3H); $^{13}$C NMR (101 MHz, $CDCl_3$) δ 204.26, 143.64, 135.92, 134.77, 134.06, 131.24, 130.39, 129.96, 129.56, 129.21, 129.18, 129.08, 128.98, 128.01, 126.70, 60.18, 50.04, 39.57, 38.51; HRMS m/z calcd. for $C_{25}H_{25}ClNO$ $[M+H]^+$ 390.16192, found 390.15992.

(Z)-5-(Benzyl(methyl)amino)-1-(4-chlorophenyl)-2-phenylpent-1-en-3-one (Z-10, JN001)

The hydrochloride Z-9 (147.0 mg, 0.34 mmol) from above was dissolved in 5 mL of DCM and stirred for 10 min at 23° C. with a solution of 10% $Na_2CO_3$ (aq, 5 mL). The layers were separated and the aqueous layer extracted with further DCM (5 mL×2). The combined organic layers were washed with brine (5 mL), dried over anhydrous $MgSO_4$, filtered, and the volatiles were removed in vacuo to yield the β-amino diarylenone hydrochloride Z-10 (133.0 mg, 0.34 mmol, quantitative) as a yellow waxy oil. $^1$H NMR (400 MHz, $CDCl_3$) δ 7.42-7.38 (m, 2H), 7.38-7.30 (m, 4H), 7.29-7.22 (m, 6H), 7.17 (dd, J=7.8, 1.8 Hz, 2H), 6.87 (s, 1H), 3.39 (s, 2H), 2.76-2.60 (m, 4H), 2.03 (s, 3H); $^{13}$C NMR (101 MHz, $CDCl_3$) δ 208.14, 144.32, 138.69, 137.10, 134.31, 134.22, 130.09, 129.10, 128.95, 128.92, 128.55, 128.33, 128.30, 127.13, 126.80, 62.37, 52.02, 41.95, 41.92; HRMS m/z calcd. for $C_{25}H_{25}ClNO$ $[M+H]^+$ 390.16192, found 390.15926.

Scheme 4: Synthesis of the diarylenone JN017.

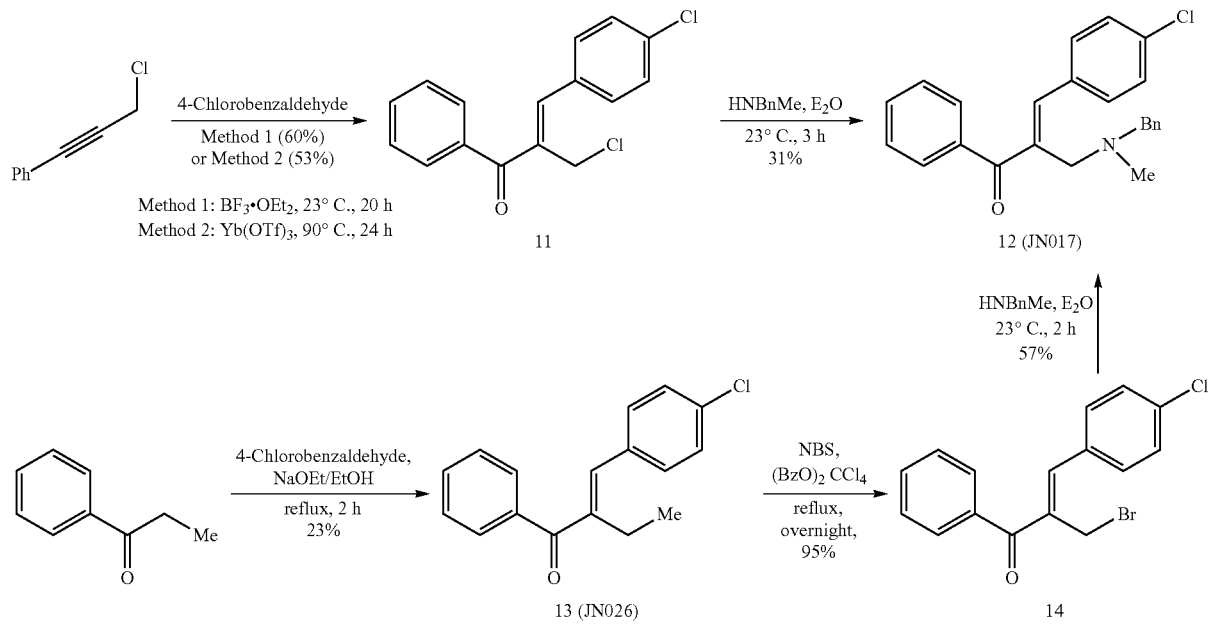

(Z)-2-(Chloromethyl)-3-(4-chlorophenyl)-1-phenyl-prop-2-en-1-one (11)

Method 1: To a flask containing 3-phenylpropargyl chloride (141.6 mg, 0.94 mmol, 1.2 eq) and 4-chlorobenzaldehyde (112.7 mg, 0.79 mmol, 1.0 eq) was added $BF_3·OEt_2$ (0.49 mL, 3.9 mmol, 5.0 eq). The resultant solution was stirred at 23° C. for 20 h. The contents were then partitioned between saturated $NaHCO_3$ (15 mL) and DCM (15 mL). The organic layer was washed with saturated $NaHCO_3$ (5 mL), water (5 mL), and brine (5 mL), dried over anhydrous $MgSO_4$, filtered, and concentrated in vacuo. The crude material was purified by column chromatography on silica gel, using a mobile phase gradient of 0 to 10% of EtOAc/hexanes to yield the chloroenone 11 (137.3 mg, 0.47 mmol, 60%) as a clear oil.

Method 2: Ytterbium(III) triflate (164.7 mg, 0.27 mmol, 0.4 eq) was added to a vial containing 4-chlorobenzaldehyde (92.8 mg, 0.66 mmol, 1.0 eq), and 3-phenylpropargyl chloride (200.0 mg, 1.3 mmol, 2.0 eq). The vial was then capped and the mixture heated at 90° C. for 24 h while stirring. Then the reaction mixture was cooled to 23° C., suspended in 3 mL of DCM, and filtered. After concentration in vacuo, the crude residue was purified by column chromatography on silica gel, using a mobile phase gradient of 0 to 10% of EtOAc/hexanes to yield the chloroenone 11 (103.1 mg, 0.35 mmol, 53%) as a clear oil.

$^1$H NMR (400 MHz, $CDCl_3$) δ 7.83-7.79 (m, 2H), 7.63-7.57 (m, 1H), 7.52-7.42 (m, 6H), 7.21 (s, 1H), 4.63 (s, 2H); $^{13}$C NMR (101 MHz, $CDCl_3$) δ 196.36, 142.96, 137.79, 137.09, 136.02, 132.68, 132.64, 130.90, 129.80, 129.39, 128.61, 38.91.

(E)-2-((Benzyl(methyl)amino)methyl)-3-(4-chlorophenyl)-1-phenylprop-2-en-1-one (12, JN017)

From 11: To a solution of the chloroenone 11 (13.3 mg, 45.6 μmol, 1.0 eq) in $Et_2O$ (1 mL) was added a 0.10 M solution of N-benzylmethylamine in $Et_2O$ (0.43 mL, 43.0 μmol, 0.95 eq). The solution was stirred for 3 h at 23° C., and then the resultant precipitate was filtered off. The filtrate was partitioned between $Et_2O$ and 10% $Na_2CO_3$ aq. (5 mL each). The aqueous layer was extracted with $Et_2O$ (5 mL×2). The combined organic layers were washed with brine (5 mL), dried over anhydrous $MgSO_4$, filtered, and the volatiles were removed in vacuo. The crude material was purified by column chromatography on silica gel, using a mobile phase gradient of 0 to 10% of EtOAc/hexanes to yield the aminoenone 12 (5.3 mg, 14.0 μmol, 31%) as a clear oil.

From 14: The bromoenone 14 (80.0 mg, 0.24 mmol, 1.0 eq) was dissolved in 2 mL of $Et_2O$ and N-benzylmethylamine (0.09 mL, 0.72 mmol, 3.0 eq) was added. The resultant solution was stirred for 2 h at 23° C., and then filtered. The filtrate was partitioned between $Et_2O$ and 10% $Na_2CO_3$ (5 mL each). The aqueous layer was extracted with $Et_2O$ (5 mL×2). The combined organic layers were washed with brine (5 mL), dried over anhydrous $MgSO_4$, filtered, and the volatiles were removed in vacuo. The crude material was purified by column chromatography on silica gel, using a mobile phase gradient of 0 to 10% of EtOAc/hexanes to yield the aminoenone 12 (51.3 mg, 0.14 mmol, 57%) as a yellow oil.

$R_f$ 0.35 (10% EtOAc/hexanes); $^1$H NMR (500 MHz, $CDCl_3$) δ 7.81 (d, J=7.5 Hz, 2H), 7.62-7.53 (m, 3H), 7.45 (t, J=7.7 Hz, 2H), 7.34 (d, J=8.6 Hz, 2H), 7.30-7.27 (m, 2H), 7.25-7.21 (m, 3H), 7.19 (s, 1H), 3.60 (s, 2H), 3.52 (s, 2H), 2.17 (s, 3H); $^{13}$C NMR (126 MHz, $CDCl_3$) δ 198.54, 142.35, 139.67, 139.00, 138.01, 135.15, 133.86, 132.36, 131.77, 129.77, 129.19, 128.81, 128.51, 128.38, 127.19, 62.38, 54.00, 42.26; HRMS m/z calcd. for $C_{24}H_{23}ClNO$ $[M+H]^+$ 376.14627, found 376.14430.

(E)-3-(4-Chlorophenyl)-2-methyl-1-phenylprop-2-en-1-one (13, JN026)

To a mixture of propiophenone (3.0 mL, 22.3 mmol, 1.0 eq) and 4-chlorobenzaldehyde (3.18 g, 22.3 mmol, 1.0 eq) in absolute EtOH (50 mL) was added NaOEt (2.4 g, 33.4 mmol, 1.5 eq). The solution was heated at reflux for 2 h, and then cooled to 23° C. After evaporation of EtOH in vacuo, the material was partitioned between EtOAc and water (100 mL each). The aqueous layer was extracted with further EtOAc (50 mL×3). The combined organic layers were washed with brine (100 mL), dried over anhydrous MgSO$_4$, filtered, and the volatiles were removed in vacuo. The crude material was purified by column chromatography on silica gel, using a mobile phase gradient of 0 to 5% of EtOAc/hexanes to yield the methyl enone 13 (1.31 g, 5.1 mmol, 23%) as a yellow oil. $^1$H NMR (400 MHz, CDCl$_3$) δ 7.77-7.71 (m, 2H), 7.58-7.52 (m, 1H), 7.49-7.43 (m, 2H), 7.41-7.32 (m, 4H), 7.11 (q, J=1.5 Hz, 1H), 2.25 (d, J=1.5 Hz, 3H); $^{13}$C NMR (101 MHz, CDCl$_3$) δ 199.27, 140.64, 138.40, 137.54, 134.62, 134.34, 131.93, 131.04, 129.60, 128.86, 128.39, 14.62; HRMS m/z calcd. for C$_{16}$H$_{14}$ClO [M+H]$^+$ 257.07277, found 257.07081.

(Z)-2-(Bromomethyl)-3-(4-chlorophenyl)-1-phenyl-prop-2-en-1-one (14)

To a solution of the methyl enone 13 (0.93 g, 3.6 mmol, 1.0 eq) in CCl$_4$ (75 mL) was added N-bromosuccinimide (0.85 g, 4.7 mmol, 1.3 eq), and benzoyl peroxide (0.45 g, 1.4 mmol, 0.4 eq). The resultant mixture was heated at reflux overnight. Then the volatiles were removed in vacuo and the residue dissolved in DCM (100 mL). The DCM solution was washed with water (100 mL×3), brine (100 mL), dried over anhydrous MgSO$_4$, filtered, and concentrated in vacuo to yield the bromoenone 14 (1.15 g, 3.4 mmol, 95% crude yield) as a yellow oil, which was used for subsequent reactions without further purification. $^1$H NMR (400 MHz, CDCl$_3$) δ 8.15-8.10 (m, 2H), aromatic region overlapped with impurities, 7.12 (s, 1H), 4.54 (s, 2H); $^{13}$C NMR (101 MHz, CDCl$_3$) δ 196.33, aromatic region overlapped with impurities, 41.60.

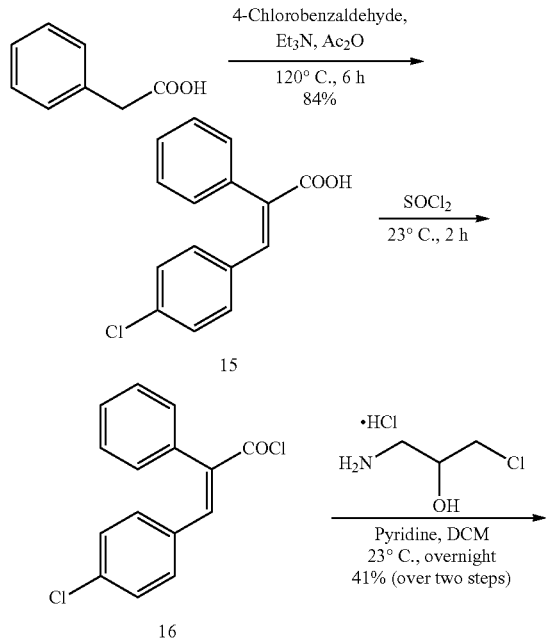

Scheme 5: Synthesis of the acrylamide JN089.

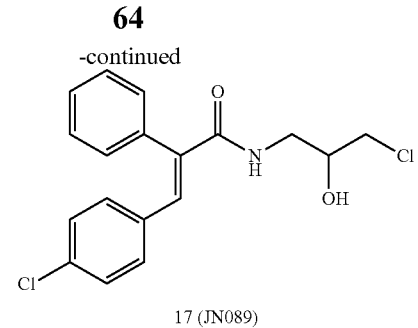

17 (JN089)

(E)-3-(4-Chlorophenyl)-2-phenylacrylic acid (15)

Method 1: To a stirred flask containing 15 mL of acetic anhydride was added phenylacetic acid (3.0 g, 21.8 mmol, 1.0 eq), 4-chlorobenzaldehyde (3.1 g, 21.8 mmol, 1.0 eq), and triethylamine (3.0 mL, 21.8 mmol, 1.0 eq). The resultant mixture was stirred at 90° C. for 6 h. Then it was cooled to 23° C. and partitioned between Et$_2$O and water (30 mL each). The organic layer was extracted with 10% sodium hydroxide (aq, 10 mL×3). The combined aqueous extracts were acidified (pH<2) with concentrated hydrochloric acid, to give a white precipitate. The organic layer also yielded a white precipitate upon standing at 4° C. overnight. All precipitates formed were filtered and washed thoroughly with cold Et$_2$O to yield the acrylic acid 15 as an off-white solid (2.92 g, 11.3 mmol, 52%).

Method 2: To phenylacetic acid (8.0 g, 58.2 mmol, 1.0 eq) and 4-chlorobenzaldehyde (8.3 g, 58.2 mmol, 1.0 eq) in a flask was added a mixture of acetic anhydride and triethylamine (v/v 1:1, 15 mL each). The resultant suspension was stirred at 120° C. for 6 h. Then it was cooled to 23° C. and 15 mL of conc. HCl and 45 mL of water were added whilst stirring. The flask was then left in a fridge overnight, and the resultant precipitate filtered and washed with water. The crude product was recrystallized from ethanol/water to yield acrylic acid 15 as an off-white solid (12.6 g, 48.7 mmol, 84%).

$^1$H NMR (500 MHz, DMSO-d$_6$) δ 7.34 (s, 1H), 7.27-7.23 (m, 2H), 7.22-7.17 (m, 1H), 7.15 (d, J=8.6 Hz, 2H), 7.10-7.06 (m, 2H), 6.92 (d, J=8.6 Hz, 2H); $^{13}$C NMR (126 MHz, DMSO-d$_6$) δ 170.25, 144.27, 140.30, 136.10, 131.06, 130.79, 129.51, 129.26, 127.89, 127.62, 125.93.

(E)-3-(4-Chlorophenyl)-2-phenylacryloyl chloride (16)

Acrylic acid 15 (300.0 mg, 1.2 mmol) was added to 3 mL of SOCl$_2$, and the suspension stirred at 23° C. for 2 h. The volatiles were removed in vacuo to yield the crude acid chloride 15 as a white solid. This material was used for the next step without further purification. $^1$H NMR (500 MHz, DMSO-d$_6$) δ 7.73 (s, 1H), 7.40-7.34 (m, 3H), 7.28-7.23 (m, 2H), 7.17-7.14 (m, 2H), 7.06-7.03 (m, 2H); $^{13}$C NMR (126 MHz, DMSO-d$_6$) δ 168.13, 137.59, 135.92, 134.13, 133.56, 133.42, 131.77, 129.42, 128.61, 128.36, 127.79.

(E)-N-(3-Chloro-2-hydroxypropyl)-3-(4-chlorophenyl)-2-phenylacrylamide (17, JN089)

To a suspension of 1-amino-3-chloropropan-2-ol hydrochloride (175.2 mg, 1.2 mmol, 1.0 eq) and pyridine (0.49 mL, 6.0 mmol, 5.0 eq) in DCM (3 mL) at 0° C. was added the crude acid chloride 16 from the above reaction. The reaction mixture was allowed to warm to 23° C. over 2 h, and then stirred overnight at rt. The resultant mixture was partitioned between DCM (3 mL) and water (5 mL). The organic layer was washed with saturated NaHCO₃ (aq, 5 mL) and brine (5 mL), dried over anhydrous MgSO₄, filtered, and concentrated in vacuo. The crude material was purified by column chromatography on silica gel, using a mobile phase gradient of 15 to 40% of EtOAc/hexanes to yield the acrylamide 17 (172.2 mg, 0.49 mmol, 41% from 15) as a white solid. $^1$H NMR (500 MHz, DMSO-d₆) δ 7.44-7.39 (m, 4H), 7.37 (t, J=5.6 Hz, 1H), 7.24 (d, J=8.6 Hz, 2H), 7.21-7.17 (m, 2H), 6.99 (d, J=8.7 Hz, 2H), 5.35 (d, J=5.3 Hz, 1H), 3.83-3.74 (m, 1H), 3.58 (dd, J=11.2, 4.4 Hz, 1H), 3.47 (dd, J=11.2, 6.0 Hz, 1H), 3.34-3.28 (m, 1H), 3.19 (ddd, J=13.4, 6.7, 5.6 Hz, 1H); $^{13}$C NMR (126 MHz, DMSO-d₆) δ 167.32, 137.21, 135.65, 133.96, 132.78, 132.71, 131.30, 129.40, 129.07, 128.27, 128.23, 69.06, 47.88, 43.19; HRMS m/z calcd. for $C_{18}H_{18}Cl_2NO_2$ [M+H]⁺ 350.07091, found 350.06477.

Scheme 6: Synthesis of the 5β-amino diarylenone E-10 (JN096).

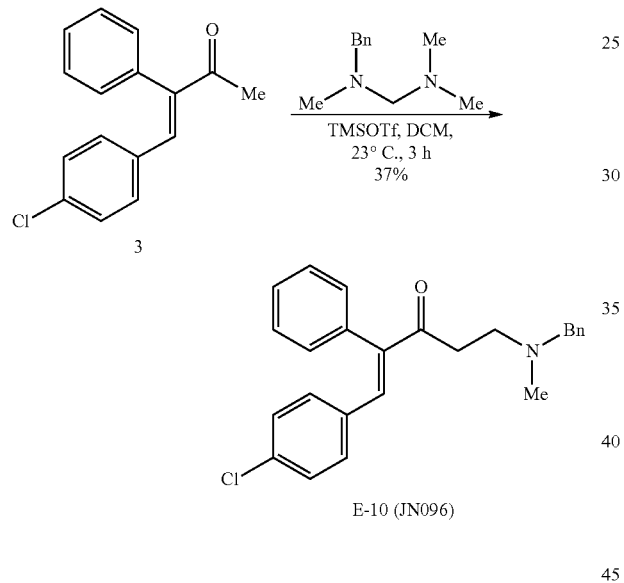

(E)-5-(Benzyl(methyl)amino)-1-(4-chlorophenyl)-2-phenylpent-1-en-3-one (E-10, JN096)

Ketone 3 (200.0 mg, 0.78 mmol, 1.0 eq) and N,N'-dibenzyl-N,N'-dimethylmethanediamine (0.25 mL, 0.93 mmol, 1.2 eq) were dissolved in DCM (5 mL) and cooled in an ice-water bath. To this was slowly added TMSOTf (0.17 mL, 0.93 mmol, 1.2 eq), and the resultant mixture allowed to warm to 23° C. and stir for 3 h. Then the reaction mixture was diluted with further DCM (10 mL), and washed with saturated NaHCO₃ (aq, 10 mL). The organic layer was dried over anhydrous MgSO₄, filtered, and concentrated in vacuo. The residue was purified by column chromatography on silica gel buffered with 1% triethylamine in hexanes, using a mobile phase gradient of 0-20% Et₂O/hexanes to yield the β-amino diarylenone E-10 (JN096, 114.0 mg, 0.29 mmol, 37%) as a white solid. $^1$H NMR (500 MHz, CDCl₃) δ 7.58 (s, 1H), 7.45-7.38 (m, 2H), 7.36-7.27 (m, 5H), 7.27-7.22 (m, 1H), 7.16 (d, J=7.3 Hz, 2H), 7.12 (d, J=8.2 Hz, 2H), 6.95 (d, J=8.2 Hz, 2H), 3.65 (s, 2H), 2.29 (s, 3H), 2.25 (s, 4H); $^{13}$C NMR (126 MHz, CDCl₃) δ 199.24, 141.40, 137.37 (2C), 136.74, 135.25, 133.22, 132.10, 129.52, 129.33, 129.05, 128.68, 128.31, 128.26, 126.94, 59.53, 40.56, 28.15; HRMS m/z calcd. for $C_{25}H_{25}ClNO$ [M+H]⁺ 390.16192, found 390.25269.

Scheme 7: Synthesis of the alkene intermediate 19.

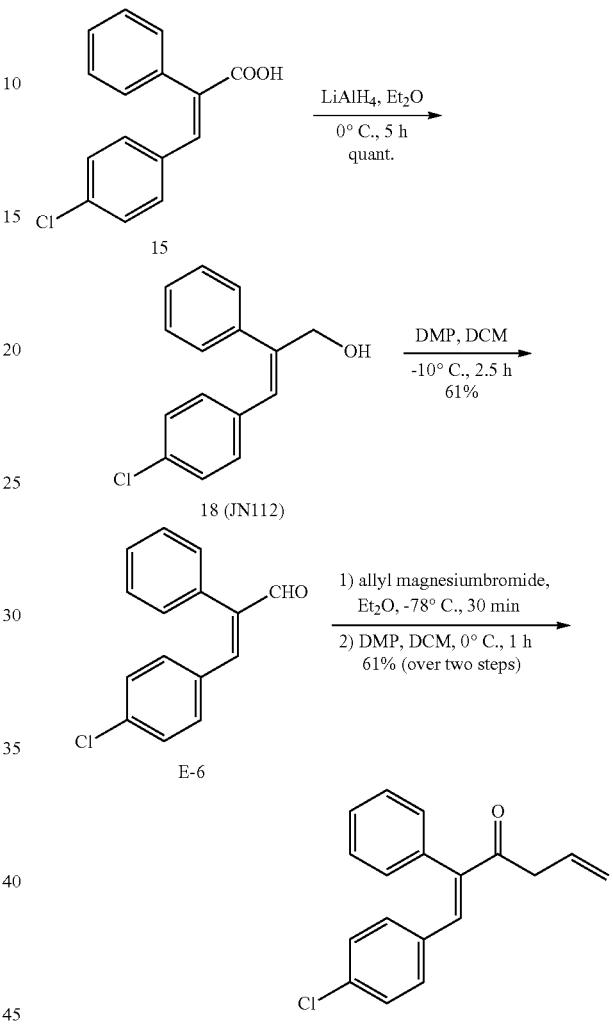

(E)-3-(4-Chlorophenyl)-2-phenylprop-2-en-1-ol (18, JN112)

To a solution of the acrylic acid 15 (5.1 g, 19.7 mmol, 1.0 eq) in Et₂O (60 mL) at 0° C., was added lithium aluminum hydride (1.58 g, 39.4 mmol, 2.0 eq) in small portions. The resultant solution was stirred at 23° C. for 1.5 h and then quenched by the slow addition of water (8 mL). To this flask was added EtO₂, 15% aq. NaOH solution and water (50 mL each), and the solution stirred for 15 min at 23° C. It was then filtered through a plug of celite, and the celite washed with further Et₂O. Layers were separated in the filtrate, and the aqueous layer extracted with further Et₂O (50 mL×2). The combined organic layers were washed with brine (150 mL), dried over anhydrous MgSO₄, filtered, and volatiles removed in vacuo to yield the α-hydroxy alkene 18 (JN112, 4.81 g, 19.7 mmol, quant.) as a yellow oil. $^1$H NMR (500 MHz, CDCl₃) δ 7.37-7.30 (m, 3H), 7.20 (dd, J=7.9, 1.7 Hz, 2H), 7.08 (d, J=8.5 Hz, 2H), 6.91 (d, J=8.6 Hz, 2H), 6.64 (d, J=1.5 Hz, 1H), 4.46 (d, J=1.5 Hz, 2H); $^{13}$C NMR (126 MHz, CDCl$_3$) δ 142.37, 138.24, 135.06, 132.59, 130.55, 129.08, 128.77, 128.29, 127.93, 125.21, 68.43.

(E)-3-(4-Chlorophenyl)-2-phenylacrylaldehyde (E-6)

To a cooled solution (ice-water bath) of the α-hydroxy alkene 18 (4.57 g, 18.7 mmol, 1.0 eq) dissolved in DCM (90 mL) was added Dess-Martin periodinane (8.80 g, 20.5 mmol, 1.1 eq) in three portions. The resultant mixture was stirred at 4° C. for 2.5 h. Then 20 mL of saturated aq. NaHCO$_3$ solution was added to the flask and stirred for 5 min. Flask contents were then partitioned between further DCM (60 mL) and saturated NaHCO$_3$ (aq, 80 mL). The organic layer was removed and washed with saturated NaHCO$_3$ (aq, 50 mL×3) and brine (50 mL). It was then dried over anhydrous MgSO$_4$, filtered, and concentrated in vacuo. The residue was purified by column chromatography on silica gel using a mobile phase gradient of 3-10% EtOAc/hexanes to give the enal E-6 (2.79 g, 11.5 mmol, 61%) as a yellowish solid. $^1$H NMR (500 MHz, CDCl$_3$) δ 9.77 (s, 1H), 7.44-7.38 (m, 3H), 7.34 (s, 1H), 7.20 (d, J=8.7 Hz, 2H), 7.19-7.16 (m, 2H), 7.13 (d, J=8.7 Hz, 2H); $^{13}$C NMR (126 MHz, CDCl$_3$) δ 193.77, 148.51, 142.27, 136.35, 133.08, 132.62, 131.99, 129.37, 129.14, 128.97, 128.68.

(E)-1-(4-Chlorophenyl)-2-phenylhexa-1,5-dien-3-one (19)

The enal E-6 (2.79 g, 11.5 mmol, 1.0 eq) was dissolved in 50 mL of Et$_2$O and then cooled to −78° C. To this was slowly added a 1.0 M solution of allyl magnesium bromide in Et$_2$O (14.9 mL, 14.9 mmol 1.3 eq), and the solution stirred for 30 min at −78° C. Then 2.5 mL of saturated aq. NH$_4$Cl solution was added and the solution allowed to warm to 23° C. whilst stirring. The reaction mixture was then diluted with saturated NH$_4$Cl (aq, 75 mL), water (30 mL), and DCM (100 mL). After layer separation, the aqueous layer was extracted with further DCM (30 mL×2). The combined organic layers were washed with brine (100 mL), dried over anhydrous MgSO$_4$, filtered, and the volatiles removed in vacuo to give the crude alcohol (2.77 g) as a yellowish solid.

The crude alcohol above (2.72 g, 9.6 mmol, 1.0 eq) was dissolved in 70 mL of DCM, and the resultant solution cooled in an ice-water bath. To that was added Dess-Martin periodinane (4.91 g, 11.5 mmol, 1.2 eq) in three portions, and the reaction mixture stirred at 0° C. for 1 h. Then 30 mL of saturated aq. NaHCO$_3$ solution was added to the flask and stirred for 5 min. Flask contents were then partitioned between further DCM (150 mL), saturated NaHCO$_3$ (aq, 150 mL), and water (20 mL). The organic layer was removed and washed with saturated NaHCO$_3$ (aq, 50 mL×2), dried over anhydrous MgSO$_4$, filtered, and concentrated in vacuo. The residue was purified by column chromatography on silica gel using a mobile phase gradient of 0-3% EtOAc/hexanes to give the alkene 19 (1.98 g, 7.0 mmol, 61%) as an off-white solid. $^1$H NMR (500 MHz, CDCl3) δ 7.59 (s, 1H), 7.48-7.37 (m, 3H), 7.17 (dd, J=7.6, 1.8 Hz, 2H), 7.12 (d, J=8.7 Hz, 2H), 6.94 (d, J=8.6 Hz, 2H), 5.96 (ddt, J=17.0, 10.3, 6.7 Hz, 1H), 5.15 (dq, J=10.2, 1.4 Hz, 1H), 5.05 (dq, J=17.1, 1.5 Hz, 1H), 3.31 (dt, J=6.8, 1.4 Hz, 2H); $^{13}$C NMR (126 MHz, CDCl$_3$) δ 199.17, 140.71, 137.19, 136.55, 135.29, 133.18, 132.17, 131.27, 129.66, 129.41, 128.68, 128.38, 118.58, 44.96.

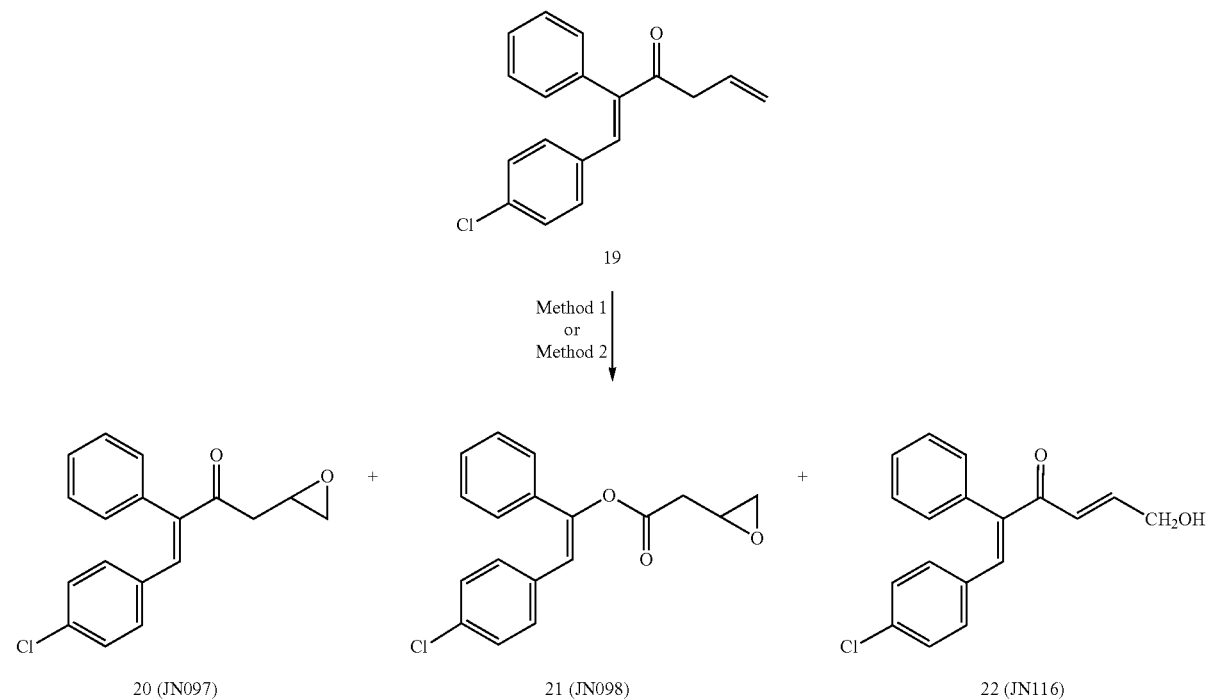

Scheme 8: Synthesis of the oxiranes JN097 and JN098, and the α-hydroxyenone JN116.

Method 1: m-CPBA, DCM, 23° C., overnight
Method 2: Oxone, NaHCO$_3$, H$_2$O/Acetone/EtOAC, 23° C., 3 h

(E)-4-(4-Chlorophenyl)-1-(oxiran-2-yl)-3-phenylbut-3-en-2-one (20, JN097)

Method 1: To a solution of the alkene 19 (506.1 mg, 1.79 mmol, 1.0 eq) in DCM (5 mL) at 0° C. was added m-CPBA (ca. 77%, 521.5 mg, 2.3 mmol, 1.3 eq), and the resultant suspension stirred at 23° C. overnight. To the solution was then added saturated sodium thiosulfate (aq, 10 mL) and the product extracted with EtOAc (10 mL×1, 5 mL×2). The combined organic layers were washed with saturated aq. NaHCO$_3$ (5 mL×3), dried over anhydrous MgSO$_4$, filtered, and concentrated in vacuo. The residue was purified by column chromatography on silica gel using a mobile phase gradient of 0-20% EtOAc/hexanes. Product containing fractions (which are a mixture of 22 and 23) were combined, concentrated in vacuo, and further purified by column chromatography on silica gel using a mobile phase of DCM to give the oxirane 20 (JN097, 55.3 mg, 0.19 mmol, 10%) as a white solid.

Method 2: To a solution of the alkene 19 in acetone/EtOAc/water (10:10:5 mL) cooled in an ice-water bath, was added NaHCO$_3$ (5.21 g, 62.0 mmol, 25 eq) whilst stirring. To this suspension was added oxone (6.0 g, 9.8 mmol, 3.93 eq) in three portions (2.0 g each, at 1 h intervals). After stirring the solution at 0° C. for 3 hours, the reaction mixture was partitioned between EtOAc (80 mL) and saturated sodium thiosulfate (aq, 100 mL). The aqueous layer was extracted with further EtOAc (20 mL×2). The combined organic layers were washed with saturated NaHCO$_3$ (aq, 100 mL×2), dried over anhydrous MgSO$_4$, filtered, and concentrated in vacuo. The crude material was purified by column chromatography on silica gel using a mobile phase gradient of 10-20% EtOAc/hexanes. The product containing fractions were combined and volatiles removed in vacuo. Residue was dissolved in to chloroform and concentrated in vacuo to near dryness. Resultant concentrated solution was diluted with hexanes, and the flask left in a refrigerator, where the product crystallizes out. Filtration of the solution and washing the product with hexanes gives the oxirane 20 (JN097, 203.3 mg, 0.68 mmol, 27%) as white needle-like crystals. $^1$H NMR (500 MHz, CDCl$_3$) δ 7.61 (s, 1H), 7.46-7.38 (m, 3H), 7.19-7.15 (m, 2H), 7.13 (d, J=8.6 Hz, 2H), 6.95 (d, J=8.5 Hz, 2H), 3.34 (tdd, J=5.6, 4.0, 2.7 Hz, 1H), 2.90-2.82 (m, 2H), 2.68 (dd, J=17.5, 5.3 Hz, 1H), 2.45 (dd, J=4.8, 2.7 Hz, 1H); $^{13}$C NMR (126 MHz, CDCl$_3$) δ 198.46, 140.56, 137.64, 136.21, 135.53, 132.98, 132.25, 129.58, 129.53, 128.74, 128.51, 48.45, 47.02, 43.63; HRMS m/z calcd. for C$_{18}$H$_{16}$ClO$_2$ [M+H]$^+$ 299.08333, found 299.08304. Analytical HPLC t$_R$=4.37 min.

(E)-2-(4-Chlorophenyl)-1-phenylvinyl 2-(oxiran-2-yl)acetate (21, JN098)

From the same reaction to generate 20 (JN097, method 1) above, the ester 21 (JN098) was also isolated (10.8 mmol, 34.3 µM, 2%) as a white solid. $^1$H NMR (400 MHz, CDCl$_3$) δ 7.38-7.29 (m, 5H), 7.15 (d, J=8.6 Hz, 2H), 7.02 (d, J=8.8 Hz, 2H), 6.43 (s, 1H), 3.33 (tdd, J=5.7, 3.9, 2.6 Hz, 1H), 2.87 (dd, J=4.9, 3.9 Hz, 1H), 2.72 (d, J=5.7 Hz, 2H), 2.60 (dd, J=4.9, 2.6 Hz, 1H); $^{13}$C NMR (126 MHz, CDCl$_3$) δ 168.91, 148.01, 134.14, 133.23, 132.70, 130.35, 129.41, 128.92, 128.76, 128.63, 119.29, 47.93, 46.81, 38.23; HRMS m/z calcd. for C$_{18}$H$_{16}$ClO$_3$ [M+H]$^+$ 315.07825, found 315.07759.

(1E,4E)-1-(4-Chlorophenyl)-6-hydroxy-2-phenylhexa-1,4-dien-3-one (22, JN116)

Purification of 20 (JN097) on silica gel, results in some epoxide ring opening to give the α-hydroxy enone 22 (JN116) as a light yellow colored solid. Yields can vary based on the reaction scale and the time spent on the column. $^1$H NMR (500 MHz, DMSO-d$_6$) δ 7.64 (s, 1H), 7.47-7.38 (m, 3H), 7.28 (d, J=8.6 Hz, 2H), 7.14 (dd, J=7.8, 1.7 Hz, 2H), 7.09 (d, J=8.7 Hz, 2H), 6.97 (dt, J=15.3, 3.7 Hz, 1H), 6.75 (dt, J=15.3, 2.1 Hz, 1H), 5.07 (t, J=5.2 Hz, 1H), 4.17 (ddd, J=5.6, 3.7, 2.1 Hz, 2H). $^{13}$C NMR (126 MHz, DMSO-d$_6$) δ 190.00, 149.01, 141.70, 136.76, 136.16, 133.71, 133.57, 131.97, 129.33, 129.03, 128.38, 128.07, 123.43, 60.59; HRMS m/z calcd. for C$_{18}$H$_{16}$ClO$_2$ [M+H]$^+$ 299.08333, found 299.08181.

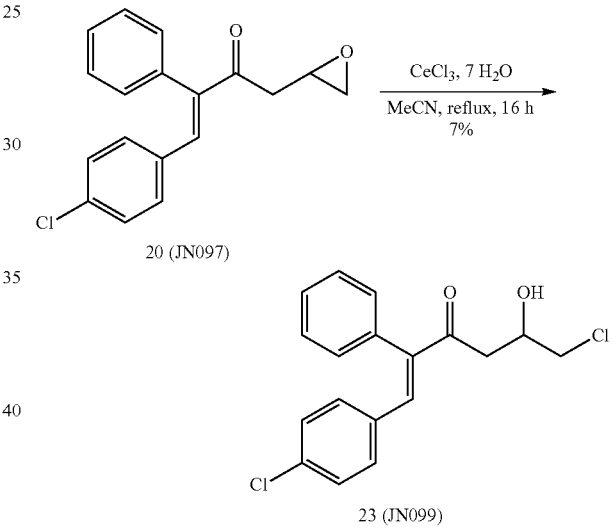

Scheme 9: Synthesis of JN099.

20 (JN097)

23 (JN099)

(E)-6-Chloro-1-(4-chlorophenyl)-5-hydroxy-2-phenylhex-1-en-3-one (23, JN099)

To a stirred solution of the oxirane 20 (43.3 mg, 0.14 mmol, 1.0 eq) in MeCN (3 mL) was added cerium(III) chloride heptahydrate (136.4 mg, 0.36 mmol, 2.5 eq), and the resultant suspension heated at reflux for 16 h. The resultant solution was filtered through a cotton plug (washed with EtOAc), and the filtrate concentrated in vacuo. The residue was purified by column chromatography on silica gel using a mobile phase gradient of 0-20% EtOAc/hexanes to give compound 23 (JN099, 3.4 mg, 10.1 µmol, 7%) as a white solid. $^1$H NMR (500 MHz, CDCl$_3$) δ 7.63 (s, 1H), 7.48-7.39 (m, 3H), 7.20-7.12 (m, 4H), 6.96 (d, J=8.2 Hz, 2H), 4.38-4.29 (m, 1H), 3.59 (dd, J=11.0, 5.3 Hz, 2H), 3.30 (d, J=4.4 Hz, 1H), 2.93-2.80 (m, 1H); $^{13}$C NMR (126 MHz, CDCl$_3$) δ 200.55, 140.62, 138.25, 135.91, 135.77, 132.80, 132.33, 129.57 (2C), 128.80, 128.62, 68.17, 48.30, 43.45; HRMS m/z calcd. for C$_{18}$H$_{17}$Cl$_2$O$_2$ [M+H]$^+$ 335.06001, found 335.0613.1.

Scheme 10: Synthesis of the N-methacryloyl acrylamide JN102.

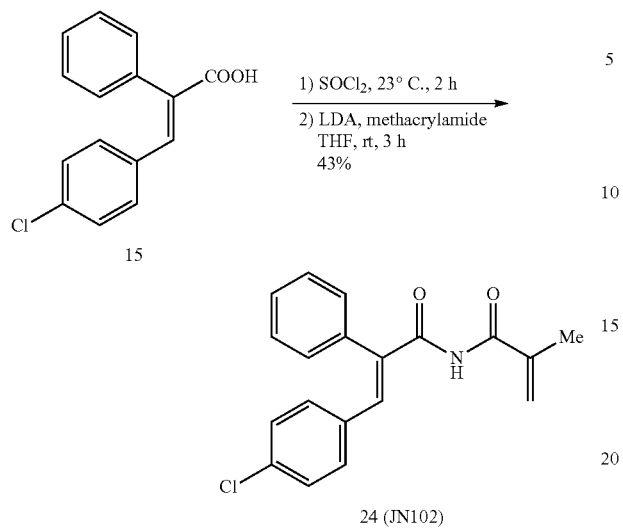

24 (JN102)

Scheme 11: Synthesis of benzylthio derivative JN108.

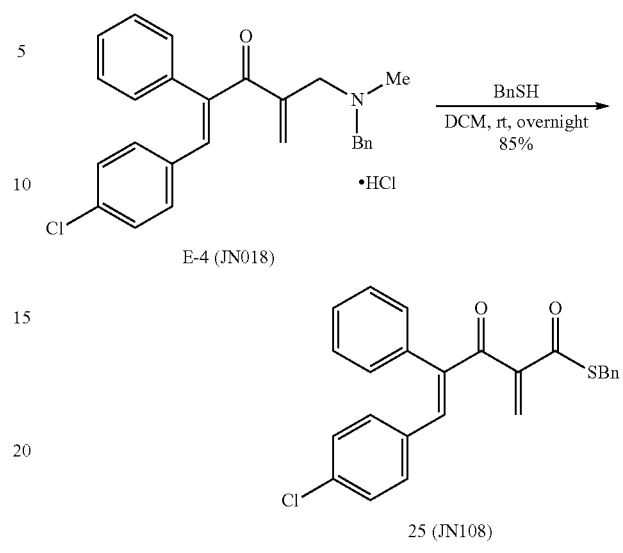

25 (JN108)

(E)-3-(4-Chlorophenyl)-N-methacryloyl-2-phenylacrylamide (24, JN102)

The acrylic acid 15 (529.0 mg, 2.04 mmol, 1.1 eq) was suspended in thionyl chloride (5 mL), and stirred at 23° C. for 2 h. Then the volatiles were removed in vacuo to yield the crude acid chloride as a solid.

In a separate flask cooled in an ice-water bath, n-BuLi (0.84 mL of a 2.19 M solution, 1.85 mmol, 1.0 eq) was added to a solution of diisopropylamine (0.26 mL, 1.85 mmol, 1.0 eq) in THF (3 mL), and the solution stirred for 30 min. To this was then added a solution of methacrylamide (161.0 mg, 1.85 mmol, 1.0 eq) in THF (2 mL). After stirring for further 1 h at 0° C., the acid chloride synthesized above was slowly added to the flask as a suspension in THF (3 mL). The resultant mixture was stirred overnight at 23° C. for 3 h, and then partitioned between EtOAc (50 mL) and saturated $NH_4Cl$/water (40:10 mL). The organic layer was separated and washed sequentially with water (20 mL) and saturated $NaHCO_3$ (aq, 20 mL). Then it was dried over anhydrous $MgSO_4$, filtered, and concentrated in vacuo. The crude residue was purified by column chromatography on silica gel buffered with 2% triethylamine in hexanes, using a mobile phase gradient of 10-20% EtOAc/hexanes. The product containing fractions were combined and the volatiles removed in vacuo to give the N-methacryloyl acrylamide 24 (JN102) as a white solid (285.4 mg, 0.88 mmol, 43%). $^1$H NMR (500 MHz, $CDCl_3$) δ 8.22 (br s, 1H), 7.91 (s, 1H), 7.58-7.48 (m, 3H), 7.34-7.29 (m, 2H), 7.14 (d, J=8.7 Hz, 2H), 6.96 (d, J=8.7 Hz, 2H), 5.34 (q, J=1.6 Hz, 1H), 5.26 (s, 1H), 1.79 (s, 3H); $^{13}$C NMR (126 MHz, $CDCl_3$) δ 165.51, 163.94, 140.09, 139.45, 135.63, 134.97, 134.10, 132.74, 132.02, 130.47, 129.73, 129.65, 128.79, 121.80, 18.13; HRMS m/z calcd. for $C_{19}H_{17}ClNO_2$ [M+H]$^+$ 326.09423, found 326.09264; Analytical HPLC $t_R$=4.28 min.

(E)-4-((Benzylthio)methyl)-1-(4-chlorophenyl)-2-phenylpenta-1,4-dien-3-one (25, JN108)

To a solution of the hydrochloride E-4 (JN018, 60.0 mg, 0.14 mmol, 1.0 eq) in DCM (1.5 mL) was added a 1.0 M solution of benzyl mercaptan in DCM (0.08 mL, 82.0 μmol, 0.6 eq), and the solution stirred at 23° C. for 3 h. Then the volatiles were removed in vacuo, and the residue passed through silica gel (0 to 8% EtOAc/hexanes). After concentrating the product containing fractions, it was purified by preparative scale TLC on silica gel using a mobile phase of 50% DCM/hexanes to give compound 25 (JN108, 28.2 mg, 69.6 μmol, 85%) as a white solid. $^1$H NMR (500 MHz, $CDCl_3$) δ 7.38-7.33 (m, 3H), 7.32-7.29 (m, 4H), 7.25-7.19 (m, 4H), 7.15 (d, J=8.6 Hz, 2H), 7.01 (d, J=8.6 Hz, 2H), 5.80 (d, J=0.7 Hz, 1H), 5.72 (q, J=1.0 Hz, 1H), 3.66 (s, 2H), 3.37 (d, J=1.0 Hz, 2H); $^{13}$C NMR (126 MHz, $CDCl_3$) δ 197.43, 144.46, 141.32, 138.04, 137.75, 136.06, 134.92, 133.36, 131.68, 129.57, 129.16, 129.06, 128.69, 128.67, 128.31, 127.25, 125.52, 36.29, 32.71; HRMS m/z calcd. for $C_{25}H_{22}ClOS$ [M+H]$^+$ 405.10744, found 405.10542.

Scheme 12: Synthesis JN113 and JN115.

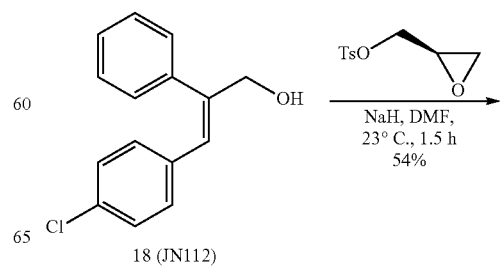

18 (JN112)

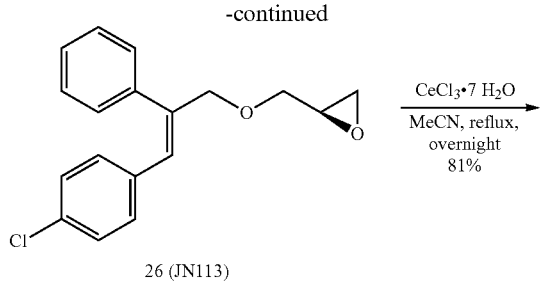

26 (JN113)

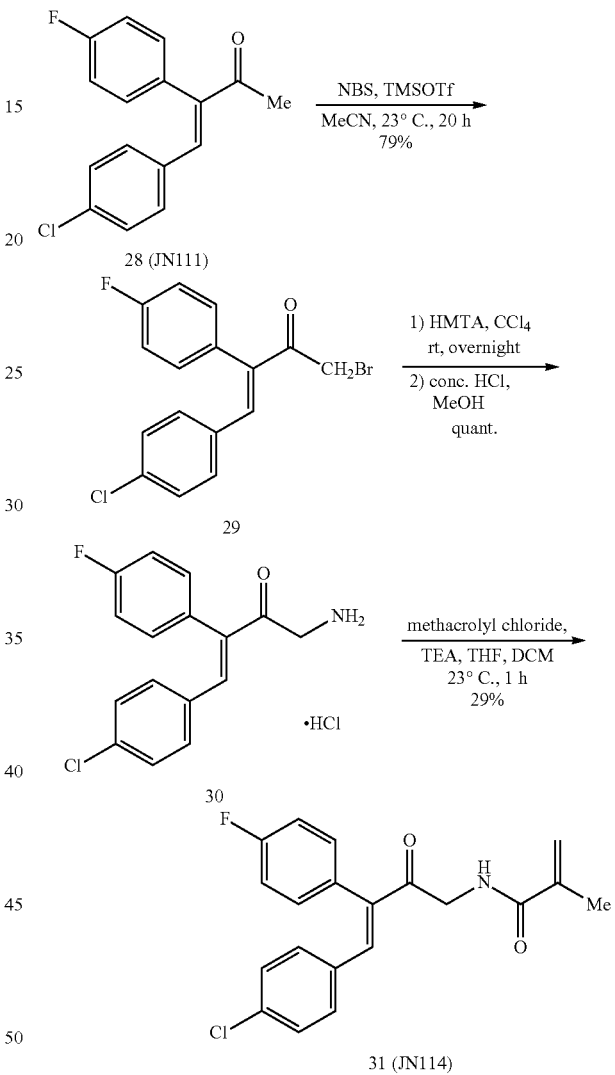

J=8.6 Hz, 2H), 6.61 (s, 1H), 4.41-4.29 (m, 2H), 3.96 (h, J=5.3 Hz, 1H), 3.67-3.60 (m, 2H), 3.57 (dd, J=11.1, 5.5 Hz, 1H), 3.53 (dd, J=11.1, 5.7 Hz, 1H), 2.39 (d, J=5.8 Hz, 1H); $^{13}$C NMR (126 MHz, CDCl$_3$) δ 139.24, 138.30, 134.84, 132.80, 130.64, 128.97, 128.69, 128.32, 127.89, 127.15, 76.74, 70.77, 70.37, 46.07; HRMS m/z calcd. for C$_{18}$H$_{17}$Cl$_2$O$_2$ [M−H]$^−$ 335.06111, found 335.04236.

Scheme 13: Synthesis of methacrylamide JN114.

(R,E)-2-(((3-(4-Chlorophenyl)-2-phenylallyl)oxy)methyl)oxirane (26, JN113)

To a suspension of NaH (60% in mineral oil, 36.8 mg, 0.92 mmol, 1.5 eq) in DMF (2 mL) at 23° C. was added a solution of the alcohol 18 (JN112, 150.0 mg, 0.61 mmol, 1.0 eq) in DMF (1 mL), and the solution stirred for 30 min at 23° C. Then the (R)-oxiran-2-ylmethyl tosylate (210.0 mg, 0.92 mmol, 1.5 eq) in DMF was added to this solution. After stirring at 23° C. for 2 h, the reaction was quenched by the addition of saturated NH$_4$Cl (aq, 3 mL) and water (1 mL). It was then extracted with EtOAc (3 mL×3). The combined organic layers were washed with water (3 mL×2) and brine (3 mL). The resultant solution was dried over anhydrous MgSO$_4$, filtered, and concentrated in vacuo. The residue was purified by column chromatography on silica gel using a mobile phase gradient of 0-20% EtOAc/hexanes to give oxirane 26 (JN113, 99.0 mg, 0.33 mmol, 54%) as an off white solid. $^1$H NMR (500 MHz, CDCl$_3$) δ 7.35-7.28 (m, 3H), 7.22-7.17 (m, 2H), 7.07 (d, J=8.6 Hz, 2H), 6.91 (d, J=8.5 Hz, 2H), 6.65 (d, J=1.3 Hz, 1H), 4.38 (dd, J=13.4, 1.5 Hz, 1H), 4.33 (dd, J=13.4, 1.5 Hz, 1H), 3.83 (dd, J=11.6, 3.0 Hz, 1H), 3.50 (dd, J=11.5, 5.8 Hz, 1H), 3.18 (ddt, J=5.7, 4.1, 2.8 Hz, 1H), 2.80 (dd, J=5.0, 4.1 Hz, 1H), 2.61 (dd, J=5.0, 2.7 Hz, 1H); $^{13}$C NMR (126 MHz, CDCl$_3$) δ 139.40, 138.54, 135.08, 132.60, 130.63, 128.90, 128.74, 128.25, 127.77, 126.65, 76.37, 71.06, 50.98, 44.42; HRMS m/z calcd. for C$_{18}$H$_{18}$ClO$_2$ [M+H]$^+$ 301.09898, found 301.07830.

(S,E)-1-Chloro-3-((3-(4-chlorophenyl)-2-phenylallyl)oxy)propan-2-ol (27, JN115)

To a stirred solution of the oxirane 26 (JN113, 27.8 mg, 0.92 μmol, 1.0 eq) in MeCN (1 mL) was added cerium(III) chloride heptahydrate (87.0 mg, 0.23 mmol, 2.5 eq), and the resultant suspension heated at reflux for 16 h. The resultant solution was filtered through a cotton plug (washed with EtOAc), and the filtrate concentrated in vacuo. The residue was purified by column chromatography on silica gel using a mobile phase gradient of 0-20% EtOAc/hexanes to give compound 27 (JN115, 25.1 mg, 74.4 μmol, 81%) as a white solid. $^1$H NMR (500 MHz, CDCl$_3$) δ 7.36-7.28 (m, 3H), 7.19 (dd, J=7.9, 1.7 Hz, 2H), 7.08 (d, J=8.6 Hz, 2H), 6.92 (d,

(E)-1-Bromo-4-(4-chlorophenyl)-3-(4-fluorophenyl)but-3-en-2-one (29)

To a solution of ketone 28 (JN111, 513.7 mg, 1.87 mmol, 1.0 eq) and N-bromosuccinimide (369.8 mg, 2.06 mmol, 1.1 eq) in MeCN (10 mL) was added TMSOTf (0.03 mL. 0.187 mmol, 0.1 eq), and the resultant solution stirred at 23° C. for 20 h. Then the reaction mixture was diluted with Et$_2$O (30 mL), and washed with water (10 mL×3) and brine (10 mL). It was then dried over anhydrous MgSO$_4$, filtered, and concentrated in vacuo. The residue was purified by column chromatography on silica gel, using a mobile phase gradient of 0.2% EtOAc/hexanes to give the ca-bromo ketone 29

(523.6 mg, 1.5 mmol, 79%) as an off-white solid. $^{1}$H NMR (500 MHz, CDCl$_3$) δ 7.67 (s, 1H), 7.23-7.11 (m, 6H), 6.97 (d, J=8.5 Hz, 2H), 4.08 (s, 2H); $^{13}$C NMR (126 MHz, CDCl$_3$) δ 192.35, 162.97 (d, J=249.1 Hz), 140.07, 137.27, 136.11, 132.52, 132.26, 131.63 (d, J=8.1 Hz), 131.35 (d, J=3.5 Hz), 128.94, 116.75 (d, J=21.6 Hz), 32.30.

(E)-1-Amino-4-(4-chlorophenyl)-3-(4-fluorophenyl)but-3-en-2-one hydrochloride (30)

To the α-bromo ketone 29 (502.3 mg, 1.42 mmol, 1.0 eq) in CCl$_4$ (5 mL) at 23° C. was added hexamethylenetetramine (214.0 mg, 1.51 mmol, 1.0 eq) and the solution stirred for 20 h. The resultant white colored precipitate was filtered and washed with CCl$_4$ (1 mL×3). This solid was dried in vacuo, and dissolved in MeOH (10 mL) to yield a pale yellow homogeneous solution. To this was added conc. HCl (1.0 mL), and the resultant mixture stirred overnight at 23° C. Then the volatiles were removed in vacuo, and the solid further dried in a vacuum desiccator to give the amine hydrochloride 30 (457.4 mg, 1.48 mmol crude, quant.) as a yellowish solid. It was used for the next reaction step without further purification. $^{1}$H NMR (500 MHz, DMSO-d$_6$) δ 8.32 (t, J=5.6 Hz, 3H), 7.90 (s, 1H), 7.36 (d, J=8.6 Hz, 2H), impurity peak overlap in aromatic region, 7.13 (d, J=8.7 Hz, 2H), 4.33 (q, J=5.5 Hz, 2H); $^{13}$C NMR (126 MHz, DMSO-d$_6$) δ 193.32, 161.98 (d, J=245.2 Hz), 140.42, 137.13, 134.57, 132.84, 132.29, 131.78 (d, J=8.2 Hz), 130.91 (d, J=3.2 Hz), 128.65, 116.07 (d, J=21.5 Hz), 70.91, 44.94.

(E)-N-(4-(4-Chlorophenyl)-3-(4-fluorophenyl)-2-oxobut-3-en-1-yl)methacrylamide (31, JN114)

To a suspension of the amine hydrochloride 30 (98.0 mg, 0.30 mmol, 1.0 eq) in THF/DCM (1:1, 8 mL) at 0° C. was added triethylamine (in 1 mL DCM, 0.13 mL, 0.90 mmol, 3.0 eq) and methacryloyl chloride (0.03 mL, 0.30 mmol, 1.0 eq). After stirring the solution at rt for 1 h, the reaction mixture was diluted with DCM (10 mL) and washed with 0.2 N HCl (5 mL), water (5 mL), and brine (5 mL). The organic layer was then dried over anhydrous MgSO$_4$, filtered, and concentrated in vacuo. The residue was purified by column chromatography on silica gel buffered with 1% triethylamine in hexanes, using a mobile phase gradient of 0-20% EtOAc/hexanes to give the methacrylamide 31 (JN114, 29.8 mg, 87.7 μmol, 29%) as an off-white solid. $^{1}$H NMR (500 MHz, CDCl$_3$) δ 7.70 (s, 1H), 7.21-7.12 (m, 6H), 6.98 (d, J=8.5 Hz, 2H), 6.81 (t, J=4.5 Hz, 1H), 5.80 (t, J=1.0 Hz, 1H), 5.40-5.37 (m, 1H), 4.39 (d, J=4.3 Hz, 2H), 1.99 (dd, J=1.6, 1.0 Hz, 3H); $^{13}$C NMR (126 MHz, CDCl$_3$) δ 195.32, 168.23, 163.01 (d, J=248.9 Hz), 139.42, 137.46, 136.24, 134.92, 132.36, 132.34, 131.50 (d, J=8.1 Hz), 130.77 (d, J=3.8 Hz), 128.98, 120.61, 116.84 (d, J=21.5 Hz), 47.73, 18.65; HRMS m/z calcd. for C$_{20}$H$_{18}$ClFNO$_2$ [M+H]$^+$ 358.10046, found 358.09728.

Scheme 14: Synthesis of β-aminoenono JN124.

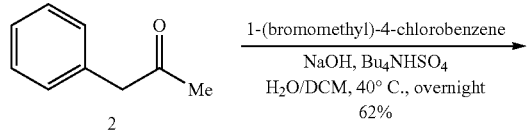

1-(bromomethyl)-4-chlorobenzene
NaOH, Bu$_4$NHSO$_4$
H$_2$O/DCM, 40° C., overnight
62%

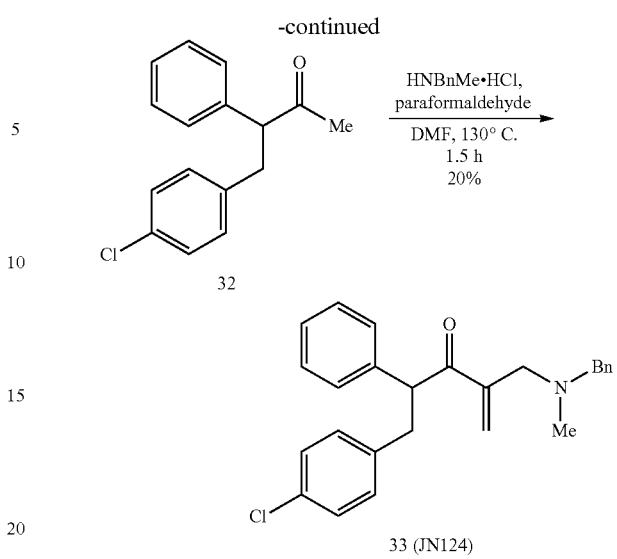

HNBnMe•HCl,
paraformaldehyde
DMF, 130° C.
1.5 h
20%

4-(4-Chlorophenyl)-3-phenylbutan-2-one (32)

To a flask containing phenylacetone 2 (0.52 mL, 3.9 mmol, 1.0 eq) and sodium hydroxide (0.17 g, 4.3 mmol, 1.1 eq) was added 1-(bromomethyl)-4-chlorobenzene (964.0 mg, 4.7 mmol, 1.2 eq). To this was added 2 mL each of water and DCM. After commencing stirring, tetrabutylammonium bisulfate (1.32 mg, 3.9 mmol, 1.0 eq) was added and the resultant solution stirred overnight at 40° C. The reaction mixture was then diluted with water (5 mL) and extracted with Et$_2$O (3 mL×3). The combined organic layers were washed with brine (3 mL), dried over anhydrous MgSO$_4$, filtered, and concentrated in vacuo. The residue was purified by column chromatography on silica gel using a mobile phase gradient of 0-4% EtOAc/hexanes to give ketone 32 (630.0 mg, 2.4 mmol, 62%) as a white solid. $^{1}$H NMR (500 MHz, CDCl$_3$) δ 7.34-7.27 (m, 3H), 7.18-7.12 (m, 4H), 6.95 (d, J=8.4 Hz, 2H), 3.85 (t, J=7.4 Hz, 1H), 3.37 (dd, J=13.9, 7.3 Hz, 1H), 2.86 (dd, J=13.9, 7.5 Hz, 1H), 2.02 (s, 3H); $^{13}$C NMR (126 MHz, CDCl$_3$) δ 207.48, 138.28, 138.19, 132.04, 130.51, 129.14, 128.47 (2C), 127.67, 61.60, 37.79, 29.63.

2-((Benzyl(methyl)amino)methyl)-5-(4-chlorophenyl)-4-phenylpent-1-en-3-one (33, JN123)

The ketone 32 (50.0 mg, 0.19 mmol, 1.0 eq), paraformaldehyde (19.9 mg, 0.64 mmol, 3.3 eq), and N-benzylmethylamine hydrochloride (67.8 mg, 0.43 mmol, 2.2 eq) were dissolved in anhydrous DMF (3 mL) and heated at 130° C. for 1.5 h. Then volatiles were removed in vacuo and the residue partitioned between Et$_2$O (5 mL) and 10% Na$_2$CO$_3$ (aq, 6 mL). The layers were separated, and the aqueous layer was extracted with further Et$_2$O (3 mL×2). The combined organic layers were washed with brine (5 mL), dried over anhydrous MgSO$_4$, filtered, and concentrated in vacuo. The residue was purified by preparative scale TLC using a mobile phase of Et$_2$O:hexanes:triethyamine (25:75:2) to yield the β-aminoenone 33 (JN123, 15.1 mg, 37.4 μmol, 20%) as a pale-yellow oil. $^{1}$H NMR (500 MHz, CDCl$_3$) δ 12.54-12.45 (m, 1H), 12.45-12.37 (m, 1H), 7.56-7.47 (m, 4H), 7.45-7.38 (m, 6H), 7.32-7.27 (m, 3H), 7.25-7.20 (m, 3H), 7.19-7.09 (m, 9H), 7.04 (s, 1H), 7.02-6.96 (m, 4H), 6.69 (s, 2H), 4.62 (dd, J=8.4, 6.6 Hz, 2H), 4.00 (ddd, J=13.6, 9.6, 4.3 Hz, 2H), 3.92-3.71 (m, 6H), 3.38 (dt, J=13.7, 8.4 Hz, 2H), 2.98 (dd, J=13.7, 6.5 Hz, 2H), 2.30 (d, J=4.7 Hz, 3H), 2.25 (d, J=4.6 Hz, 3H); $^{13}$C NMR (126 MHz, CDCl$_3$) δ 199.32, 199.25, 138.35, 137.94, 137.91, 137.56, 137.52, 136.73, 136.51, 132.53, 132.50, 131.35, 130.57, 130.52, 130.32, 130.29, 129.51, 129.48, 128.65, 128.43, 128.37, 128.08, 128.02, 127.94, 59.87, 59.74, 54.77, 54.69, 52.43, 52.25, 39.27, 39.21, 38.88, 38.36; HRMS m/z calcd. for C$_{26}$H$_{27}$ClNO [M+H]$^+$ 404.17757, found 404.17670.

Scheme 15: Synthesis of tetrahydropyrimidinyl derivative JN125.

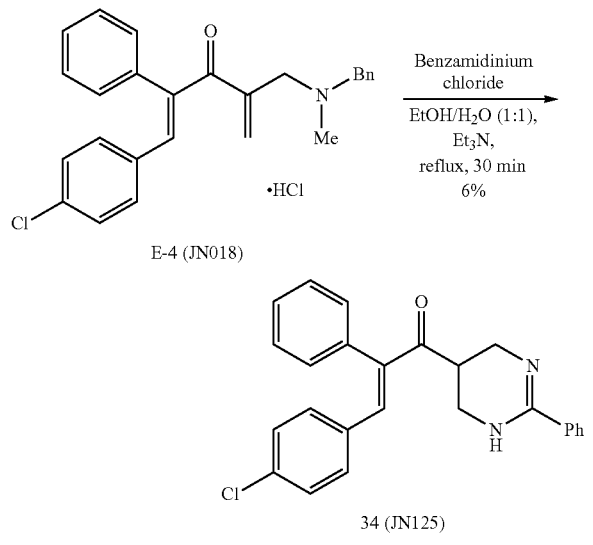

34 (JN125)

(E)-3-(4-Chlorophenyl)-2-phenyl-1-(2-phenyl-1,4,5,6-tetrahydropyrimidin-5-yl)prop-2-en-1-one (34, JN125)

Benzamidinium chloride (hydrate, 35.4 mg, 0.22 mmol, 1.0 eq) and the diaryldienone hydrochloride E-4 (96.2 mg, 0.22 mmol, 1.0 eq) were dissolved in to a 1:1 mixture of EtOH/H$_2$O (3 mL). To this was added triethylamine (0.13 mL, 0.93 mmol, 4.2 eq) and the mixture heated at reflux for 30 min. After cooling the reaction mixture back to 23° C. volatiles were removed in vacuo and the residue partitioned between DCM and 10% aq. Na$_2$CO$_3$ (4 mL each). The aqueous layer was extracted with further DCM (2 mL×2). The combined organic layers were washed with brine (5 mL), dried over anhydrous MgSO$_4$, filtered, and concentrated in vacuo. The residue was purified by preparative scale TLC using a mobile phase of MeOH: DCM:triethyamine (5:95:2). Thus obtained white solid was suspended in chloroform (1 mL), filtered, and volatiles removed in vacuo to yield the tetrahydropyrimidinyl derivative 34 (JN125, 5.7 mg, 14.2 µmol, 6%) as a white solid. $^1$H NMR (500 MHz, CDCl$_3$) δ 7.62 (dd, J=8.3, 1.4 Hz, 2H), 7.59 (s, 1H), 7.45-7.31 (m, 6H), 7.19 (dd, J=7.9, 1.7 Hz, 2H), 7.13 (d, J=8.6 Hz, 2H), 6.95 (d, J=8.6 Hz, 2H), 3.64 (dd, J=13.0, 4.6 Hz, 2H), 3.57 (dd, J=13.4, 9.6 Hz, 2H), 3.26 (tt, J=9.5, 4.8 Hz, 1H); $^{13}$C NMR (126 MHz, CDCl$_3$) δ 201.65, 154.51, 140.81, 137.90, 136.13, 136.09, 135.50, 133.07, 132.23, 130.28, 129.58, 129.54, 128.73, 128.60, 128.58, 126.31, 45.02, 39.19; HRMS m/z calcd. for C$_{25}$H$_{22}$ClN$_2$O [M+H]$^+$ 401.14152, found 401.13986.

Scheme 16: Synthesis of diarylenamides JN134 and JN137.

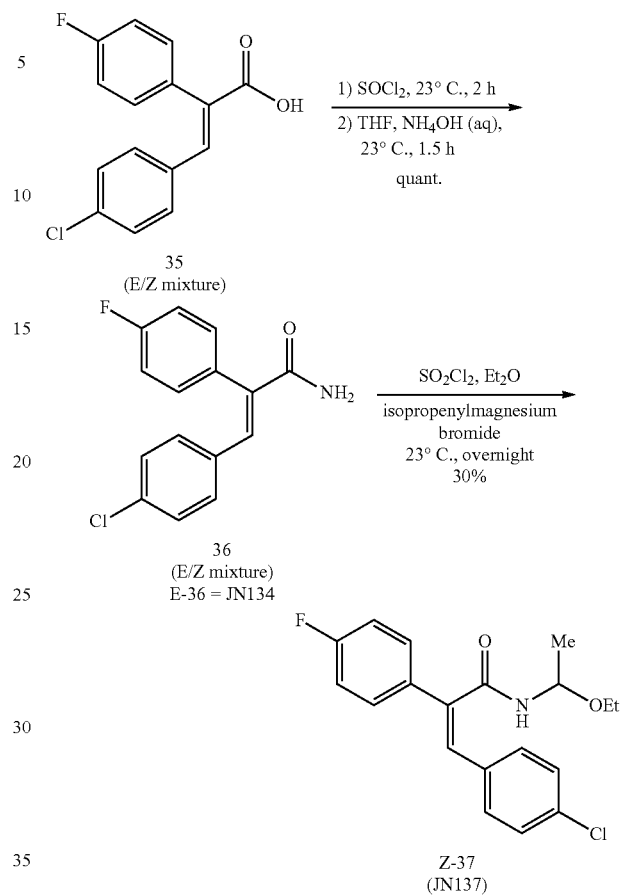

(E)-3-(4-Chlorophenyl)-2-(4-fluorophenyl)acrylamide (α-36, JN134)

The acid 35 (1.36 g, 4.9 mmol, 1.0 eq) was dissolved in to 14 mL of thionyl chloride and resultant solution stirred at 23° C. for 2 h. Then volatiles were removed in vacuo and the resultant acid chloride (in 12 mL THF) was added to a cold (ice-water bath) solution of NH$_4$OH (aq, 20 mL). Resultant biphasic mixture was stirred vigorously at 23° C. for 2 h and then partitioned between water (10 mL) and EtOAc (20 mL). The aqueous layer was extracted with further EtOAc (10 mL×2). Combined organic layers were washed with brine (20 mL), dried over anhydrous MgSO$_4$, filtered, and concentrated in vacuo. This yielded a pale brown solid (1.35 g, 4.9 mmol, quant.) containing the E and the Z isomers of the acrylamide 36, that could be used for subsequent reactions without further purification. A small amount of this mixture was purified by column chromatography using a mobile phase gradient of 10-50% EtOAc/hexanes on silica gel buffered with 2% triethylamine/hexanes to yield E-36 (JN134) as a white solid. $^1$H NMR (DMSO-d$_6$) δ 7.42 (s, 1H), 7.33 (br s, 1H), 7.28 (d, J=8.6 Hz, 2H), 7.25-7.15 (m, 4H), 7.06 (br s, 1H), 7.00 (d, J=8.6 Hz, 2H). $^{13}$C NMR (DMSO-d$_6$) δ 168.75, 161.78 (d, J=244.4 Hz), 136.52, 133.92, 133.00, 132.80, 132.38 (d, J=3.2 Hz), 131.54 (d, J=8.3 Hz), 131.29, 128.35, 115.86 (d, J=21.2 Hz); HRMS m/z calcd. for C$_{15}$H$_{12}$ClFNO [M+H]$^+$ 276.05860, found 276.05836.

(Z)-3-(4-Chlorophenyl)-N-(1-ethoxyethyl)-2-(4-fluorophenyl)acrylamide (Z-37, JN137)

To a cooled (ice-water bath) solution of sulfuryl chloride (0.06 mL, 0.76 mmol, 2.0 eq) in Et$_2$O (3.0 mL) was added a solution of isopropenyl magnesiumbromide (0.5 M in THF, 0.76 mL, 0.38 mmol, 1.0 eq) and the resultant solution stirred for 1 h at 23° C. This solution was then added to a solution of the crude acrylamide 36 (316.1 mg, 1.15 mmol, 3.0 eq) in Et$_2$O (6.0 mL), and the reaction left to stir overnight at 23° C. Then the reaction mixture was partitioned between EtOAc and aq. NaHCO$_3$ (5 mL each). The organic layer was washed with water/brine (1:1, 5 mL), dried over anhydrous MgSO$_4$, filtered, and concentrated in vacuo. The residue was purified by preparative scale TLC using a mobile phase of EtOAc:hexanes:triethyamine (25:75:2) to yield the acrylamide Z-37 (JN137, 40.1 mg, 0.12 mmol, 30%) as a white solid. $^1$H NMR (500 MHz, CDCl$_3$) δ 7.49 (dd, J=8.9, 5.2 Hz, 2H), 7.43-7.38 (m, 2H), 7.32 (d, J=8.5 Hz, 2H), 7.08 (dd, J=8.9, 8.4 Hz, 2H), 6.89 (s, 1H), 5.79 (d, J=9.4 Hz, 1H), 5.41 (dq, J=9.3, 5.9 Hz, 1H), 3.57-3.51 (m, 1H), 3.51-3.46 (m, 1H), 1.19 (d, J=5.9 Hz, 3H), 1.14 (t, J=7.0 Hz, 3H); $^{13}$C NMR (126 MHz, CDCl$_3$) δ 168.93, 163.06 (d, J=248.9 Hz), 138.36, 134.44, 133.97, 132.98 (d, J=3.3 Hz), 129.97, 128.92, 128.22 (d, J=8.2 Hz), 127.66 (d, J=1.7 Hz), 115.99 (d, J=21.8 Hz), 76.98, 64.06, 21.60, 15.29; HRMS m/z calcd. for C$_{17}$H$_{14}$ClFNO [M-OEt]$^+$ 302.07425, found 302.07457.

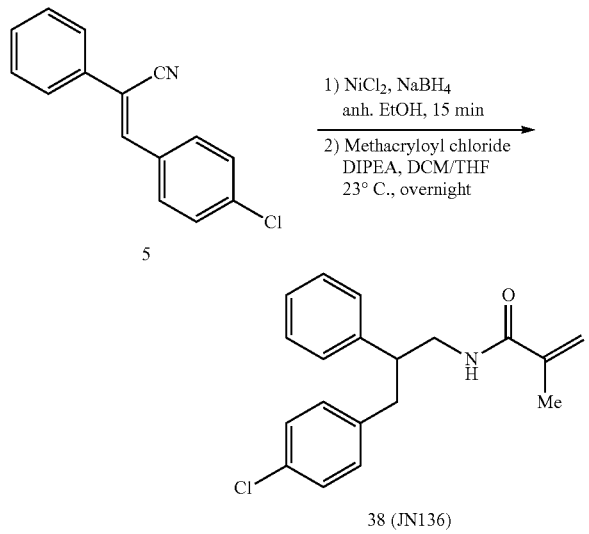

Scheme 17: Synthesis of the methacrylamide JN136.

N-(3-(4-Chlorophenyl)-2-phenylpropyl)methacrylamide (38, JN136)

In a round-bottomed flask affixed with a reflux condenser was placed the nitrile 5 (2.0 g, 8.34 mmol, 1.0 eq) and anhydrous nickel(II) chloride (1.08 g, 8.34 mmol, 1.0 eq). To this was added dry ethanol (20 mL) and the suspension cooled in an ice-water bath. Then sodium borohydride (955.3 mg, 25.0 mmol, 3.0 eq) was added in three portions after which the ice bath was removed, and the solution allowed to warm to 23° C. where an exothermic reaction initiates. After 15 min, the black colored suspension was filtered through a pad of celite. The filtrate was diluted with water (200 mL) and extracted with EtOAc (50 mL×3). Combined organic layers were dried over anhydrous MgSO$_4$, filtered, and concentrated in vacuo. The resultant pale green waxy residue (1.6 g, 6.5 mmol, 78%) was used for the next reaction step without further purification.

The crude amine obtained above (602.3 mg, 2.45 mmol, 1.0 eq) was dissolved in DCM/THF (9:6 mL) and the solution cooled to 0° C. To this was added diisopropylethyl amine (1.28 mL, 7.4 mmol, 3.0 eq), followed by acryloyl chloride (0.24 mL, 2.45 mmol, 1.0 eq). The resultant solution was allowed to warm to 23° C. and stir overnight. Then it was diluted with EtOAc (50 mL) and washed with saturated NH$_4$Cl/water (40:10 mL), water (20 mL), and saturated NaHCO$_3$ (aq, 20 mL). Resultant organic layer was dried over anhydrous MgSO$_4$, filtered, and concentrated in vacuo. The crude residue was purified by column chromatography on silica gel buffered with 2% triethylamine in hexanes, using a mobile phase gradient of 0-20% EtOAc/hexanes. The product containing fractions were combined and the volatiles removed in vacuo to give the methacrylamide 38 (JN136) as a pale-yellow liquid (359.0 mg, 1.14 mmol, 46%). $^1$H NMR (500 MHz, CDCl$_3$) δ 7.33-7.27 (m, 2H), 7.25-7.21 (m, 1H), 7.16 (d, J=8.4 Hz, 2H), 7.14-7.11 (m, 2H), 6.97 (d, J=8.4 Hz, 2H), 5.54 (br t, J=5.9 Hz, 1H), 5.43 (m, 1H), 5.20 (m, 1H), 3.81 (ddd, J=13.6, 7.0, 5.5 Hz, 1H), 3.34 (ddd, J=13.5, 9.3, 4.9 Hz, 1H), 3.16-3.05 (m, 1H), 2.96 (dd, J=13.8, 6.6 Hz, 1H), 2.89 (dd, J=13.8, 8.4 Hz, 1H), 1.81 (dd, J=1.6, 1.0 Hz, 3H); $^{13}$C NMR (126 MHz, CDCl$_3$) δ 168.41, 141.64, 140.09, 138.01, 132.04, 130.45, 128.92, 128.51, 127.93, 127.23, 119.43, 47.48, 44.54, 39.96, 18.62; HRMS m/z calcd. for C$_{19}$H$_{21}$ClNO [M+H]$^+$ 314.13062, found 314.12985.

Example 2: Compound Library

Using the general synthetic schemes and techniques described above, additional exemplary compounds were prepared, as listed in Table 2.

TABLE 2

Physical Properties of Synthesized Compounds

| Compound No. | NMR[1] | Formula[2] m/z (calc.) | m/z (meas.) |
|---|---|---|---|
| JN001 | $^1$H NMR (400 MHz) δ 7.42-7.38 (m, 2H), 7.38-7.30 (m, 4H), 7.29-7.22 (m, 6H), 7.17 (dd, J = 7.8, 1.8 Hz, 2H), 6.87 (s, 1H), 3.39 (s, 2H), 2.76-2.60 (m, 4H), 2.03 (s, 3H); $^{13}$C NMR (101 MHz) δ 208.14, 144.32, 138.69, 137.10, 134.31, 134.22, 130.09, 129.10, 128.95, 128.92, 128.55, 128.33, 128.30, 127.13, 126.80, 62.37, 52.02, 41.95, 41.92. | C$_{25}$H$_{25}$ClNO 390.16192 | 390.15926 |

TABLE 2-continued

Physical Properties of Synthesized Compounds

| Compound No. | NMR[1] | Formula[2] m/z (calc.) | m/z (meas.) |
|---|---|---|---|
| JN002 | $^1$H NMR (400 MHz) δ 12.74 (m, 1H), 7.51-7.40 (m, 5H), 7.40-7.34 (m, 5H), 7.32 (d, J = 8.5 Hz, 2H), 7.22 (d, J = 8.4 Hz, 2H), 6.97 (s, 1H), 4.11 (d, J = 13.4 Hz, 1H), 3.94 (d, J = 12.2 Hz, 1H), 3.41-3.05 (m, 4H), 2.46 (s, 3H); $^{13}$C NMR (101 MHz) δ 204.26, 143.64, 135.92, 134.77, 134.06, 131.24, 130.39, 129.96, 129.56, 129.21, 129.18, 129.08, 128.98, 128.01, 126.70, 60.18, 50.04, 39.57, 38.51. | $C_{25}H_{25}ClNO$ 390.16192 | 390.15992 |
| JN003 | $^1$H NMR (400 MHz) δ 7.61-7.56 (m, 2H), 7.42-7.30 (m, 7H), 6.76 (s, 1H), 6.07 (ddd, J = 17.2, 10.5, 4.8 Hz, 1H), 5.42 (br tt, J = 4.8, 1.8 Hz, 1H), 5.33 (dt, J = 17.3, 1.6 Hz, 1H), 5.22 (dt, J = 10.5, 1.6 Hz, 1H), 2.28 (d, J = 4.9 Hz, 1H); $^{13}$C NMR (101 MHz) δ 143.09, 139.74, 139.26, 135.07, 133.16, 130.38, 130.29, 128.53, 128.47, 128.14, 127.60, 116.06, 70.99. | [M − H]$^-$ $C_{17}H_{14}ClO$ 269.07277 | 269.07275 |
| JN004 | $^1$H NMR (400 MHz) δ 7.43-7.30 (m, 5H), 7.30-7.22 (m, 4H), 7.07 (s, 1H), 6.41 (dd, J = 17.6, 10.3 Hz, 1H), 6.23 (dd, J = 17.6, 1.1 Hz, 1H), 5.90 (dd, J = 10.3, 1.1 Hz, 1H); $^{13}$C NMR (101 MHz) δ 199.78, 141.57, 137.66, 137.08, 134.25, 134.19, 132.37, 130.21, 129.28, 128.97, 128.87, 128.57, 126.60. | $C_{17}H_{14}ClO$ 269.07277 | 269.07066 |
| JN005 | $^1$H NMR (400 MHz) δ 7.38-7.29 (m, 3H), 7.20-7.15 (m, 2H), 7.06 (d, J = 8.6 Hz, 2H), 6.86 (d, J = 8.6 Hz, 2H), 6.68 (s, 1H), 5.92 (ddd, J = 17.1, 10.4, 5.9 Hz, 1H), 5.26 (dt, J = 17.2, 1.4 Hz, 1H), 5.17 (dt, J = 10.4, 1.3 Hz, 1H), 4.98-4.93 (br m, 1H), 1.92 (d, J = 4.2 Hz, 1H); $^{13}$C NMR (101 MHz) δ 144.05, 138.58, 137.93, 135.05, 132.67, 130.61, 129.41, 128.88, 128.24, 127.82, 126.11, 116.18, 77.98. | [M − OH]$^+$ $C_{17}H_{14}Cl$ 253.07785 | 253.07655 |
| JN006 | $^1$H NMR (400 MHz) δ 12.55 (m, 1H), 7.47-7.30 (m, 7H), 7.24 (d, J = 8.2 Hz, 2H), 6.99 (s, 1H), 3.54 (dq, J = 11.4, 5.5 Hz, 2H), 3.26 (p, J = 6.8 Hz, 2H), 3.15 (t, J = 7.2 Hz, 2H), 2.57 (dq, J = 14.8, 7.5 Hz, 2H), 2.22-2.09 (m, 2H), 2.00 (m, 2H); $^{13}$C NMR (101 MHz) δ 204.44, 143.75, 135.96, 134.83, 134.23, 130.01, 129.70, 129.23, 129.18, 129.13, 126.75, 53.77, 49.82, 39.63, 23.46. | $C_{21}H_{23}ClNO$ 340.14627 | 340.14411 |
| JN007 | $^1$H NMR δ 12.70 (m, 1H), 7.45-7.32 (m, 7H), 7.24 (d, J = 8.3 Hz, 2H), 7.00 (s, 1H), 3.30-3.21 (m, 2H), 3.19-3.10 (m, 2H), 2.63 (s, 6H); $^{13}$C NMR δ 203.99, 143.55, 135.91, 134.92, 134.08, 130.00, 129.94, 129.28, 129.24, 129.18, 126.78, 52.59, 43.33, 38.61. | $C_{19}H_{21}ClNO$ 314.13062 | 314.12903 |
| JN008 | $^1$H NMR (400 MHz) δ 12.19 (m, 1H), 7.44-7.31 (m, 7H), 7.24 (d, J = 8.6 Hz, 2H), 7.01 (s, 1H), 3.29-3.11 (m, 4H), 2.84-2.70 (m, 4H), 1.72-1.55 (m, 4H), 1.37-1.16 (m, 12H), 0.88 (t, J = 6.7 Hz, 6H); $^{13}$C NMR (101 MHz) δ 204.64, one low-field carbon not distinguishable due to low sample concentration, 143.87, 135.94, 134.85, 134.31, 129.98, 129.44, 129.20, 129.13, 126.74, 52.81, 47.68, 38.47, 31.19, 26.51, 22.88, 22.55, 14.00. | $C_{29}H_{41}ClNO$ 454.28712 | 454.28469 |
| JN009 | $^1$H NMR δ 13.63 (m, 1H), 7.42-7.35 (m, 7H), 7.24 (d, J = 8.6 Hz, 2H), 7.00 (s, 1H), 3.98-3.83 (m, 4H), 3.51-3.44 (m, 2H), 3.39 (t, J = 6.8 Hz, 2H), 3.36-3.30 (m, 2H), 3.14 (t, J = 6.9 Hz, 2H), 2.85 (s, 3H); $^{13}$C NMR δ 203.00, 143.14, 135.94, 135.03, 133.85, 130.54, 130.13, 129.40, 129.35, 129.25, 126.85, 51.58, 49.87, 48.63, 43.09, 37.53. | $C_{22}H_{26}ClN_2O$ 369.17282 | 314.12903 |

TABLE 2-continued

Physical Properties of Synthesized Compounds

| Compound No. | NMR[1] | Formula[2] m/z (calc.) | m/z (meas.) |
|---|---|---|---|
| JN010 | $^1$H NMR (400 MHz) δ 7.56-7.53 (m, 2H), 7.51 (d, J = 8.4 Hz, 2H), 7.39-7.31 (m, 3H), 7.27 (d, J = 8.2 Hz, 2H), 6.73 (s, 1H), 6.05 (ddd, J = 17.3, 10.5, 4.8 Hz, 1H), 5.43-5.38 (br m, 1H), 5.31 (dt, J = 17.2, 1.5 Hz, 1H), 5.22 (dt, J = 10.5, 1.6 Hz, 1H), 1.83 (d, J = 5.2 Hz, 1H); $^{13}$C NMR (101 MHz) δ 143.26, 139.77, 139.35, 135.65, 131.64, 130.71, 130.62, 128.58, 128.31, 127.79, 121.52, 116.28, 71.23. | $C_{17}H_{16}BrO$ 315.03790 | Not Available |
| JN011 | $^1$H NMR (400 MHz) δ 7.58-7.52 (m, 2H), 7.42-7.28 (m, 5H), 7.08 (t, J = 8.7 Hz, 2H), 6.77 (s, 1H), 6.07 (ddd, J = 17.3, 10.5, 4.8 Hz, 1H), 5.45-5.39 (br m, 1H), 5.32 (dt, J = 17.3, 1.6 Hz, 1H), 5.22 (ddd, J = 10.5, 1.8, 1.3 Hz, 1H), 1.84 (d, J = 5.6 Hz, 1H); $^{13}$C NMR (101 MHz) δ 162.18 (d, J = 247.1 Hz), 142.61 (d, J = 1.0 Hz), 139.89, 139.47, 132.75 (d, J = 3.4 Hz), 130.78 (d, J = 2.0 Hz), 130.71, 128.62, 128.29, 127.70, 116.16, 115.45 (d, J = 21.4 Hz), 71.21. | $[M - OH]^+$ $C_{17}H_{14}F$ 237.10741 | 237.10633 |
| JN012 | $^1$H NMR (400 MHz) δ 7.60-7.54 (m, 2H), 7.39-7.27 (m, 5H), 7.21 (d, J = 7.7 Hz, 2H), 6.81 (s, 1H), 6.10 (ddd, J = 17.3, 10.5, 4.6 Hz, 1H), 5.55-5.49 (br m, 1H), 5.34 (dt, J = 17.3, 1.6 Hz, 1H), 5.22 (dt, J = 10.5, 1.7 Hz, 1H), 2.39 (s, 3H), 1.84 (d, J = 5.6 Hz, 1H); $^{13}$C NMR (101 MHz) δ 141.95, 140.18, 139.70, 137.26, 133.87, 131.83, 129.21, 128.99, 128.63, 128.23, 127.51, 115.87, 71.21, 21.35. | $[M - OH]^+$ $C_{18}H_{17}$ 233.13248 | 233.13125 |
| JN013 | $^1$H NMR (400 MHz) δ 7.37-7.29 (m, 3H), 7.24-7.18 (m, 2H), 6.91 (d, J = 8.0 Hz, 2H), 6.84 (d, J = 8.3 Hz, 2H), 6.69 (s, 1H), 5.95 (ddd, J = 17.2, 10.4, 5.8 Hz, 1H), 5.27 (dt, J = 17.2, 1.5 Hz, 1H), 5.17 (dt, J = 10.4, 1.4 Hz, 1H), 5.01-4.93 (br m, 1H), 2.24 (s, 3H), 1.85 (d, J = 4.6 Hz, 1H); $^{13}$C NMR (101 MHz) δ 142.37, 138.91, 138.46, 136.86, 133.60, 129.59, 129.33, 128.82, 128.76, 127.55, 127.51, 115.85, 78.26, 21.24. | $[M - OH]^+$ $C_{18}H_{17}$ 251.13248 | 233.13140 |
| JN014 | $^1$H NMR (400 MHz) δ 7.61-7.52 (m, 2H), 7.39-7.28 (m, 5H), 6.93 (d, J = 8.7 Hz, 2H), 6.78 (s, 1H), 6.10 (ddd, J = 17.3, 10.5, 4.6 Hz, 1H), 5.54-5.48 (br m, 1H), 5.34 (ddd, J = 17.3, 1.9, 1.4 Hz, 1H), 5.22 (ddd, J = 10.6, 1.9, 1.3 Hz, 1H), 3.84 (s, 3H), 1.84 (d, J = 5.6 Hz, 1H); $^{13}$C NMR (101 MHz) δ 159.04, 141.20, 140.28, 139.71, 131.54, 130.39, 129.25, 128.61, 128.23, 127.45, 115.93, 113.95, 71.24, 55.43. | $[M - OH]^+$ $C_{18}H_{17}O$ 249.12739 | 249.12616 |
| JN015 | $^1$H NMR (400 MHz) δ 12.61 (m, 1H), 7.50 (d, J = 8.0 Hz, 2H), 7.44-7.30 (m, 5H), 7.17 (d, J = 7.9 Hz, 2H), 6.96 (s, 1H), 3.30-3.19 (m, 2H), 3.12 (t, J = 6.8 Hz, 2H), 2.62 (d, J = 4.4 Hz, 6H). $^{13}$C NMR (101 MHz) δ 203.95, 143.62, 135.91, 134.52, 132.18, 130.23, 129.93, 129.26, 129.17, 126.75, 123.07, 52.50, 43.21, 38.53. | $C_{20}H_{20}BrNO$ 369.07173 | 358.07809 |
| JN016 | $^1$H NMR (400 MHz) δ 12.56 (m, 1H), 7.46-7.30 (m, 5H), 7.27-7.19 (m, 2H), 7.05 (s, 1H), 6.89 (d, J = 8.2 Hz, 2H), 3.82 (s, 3H), 3.26 (t, J = 7.2 Hz, 2H), 3.11 (t, J = 6.9 Hz, 2H), 2.61 (s, 6H); $^{13}$C NMR (101 MHz) δ 204.60, 160.17, 141.08, 136.55, 131.40, 130.12, 129.00, 128.54, 128.04, 126.64, 114.38, 55.46, 52.59, 43.04, 38.31. | $C_{20}H_{24}NO_2$ 310.18016 | 310.17848 |
| JN017 | $^1$H NMR δ 7.81 (d, J = 7.5 Hz, 2H), 7.62-7.53 (m, 3H), 7.45 (t, J = 7.7 Hz, 2H), 7.34 (d, J = 8.6 Hz, 2H), 7.30-7.27 (m, 2H), 7.25-7.21 (m, 3H), 7.19 (s, 1H), 3.60 (s, 2H), 3.52 (s, 2H), 2.17 (s, 3H); $^{13}$C NMR δ 198.54, 142.35, 139.67, 139.00, 138.01, 135.15, 133.86, 132.36, 131.77, 129.77, 129.19, 128.81, 128.51, 128.38, 127.19, 62.38, 54.00, 42.26. | $C_{24}H_{23}ClNO$ 376.14627 | 376.14430 |

TABLE 2-continued

Physical Properties of Synthesized Compounds

| Compound No. | NMR[1] | Formula[2] m/z (calc.) | m/z (meas.) |
|---|---|---|---|
| JN018 | $^1$H NMR (400 MHz) δ 12.78 (m, 1H), 7.69-7.63 (m, 2H), 7.49-7.43 (m, 3H), 7.40 (s, 1H), 7.39-7.36 (m, 3H), 7.19-7.14 (m, 4H), 7.12 (s, 1H), 7.04 (d, J = 8.6 Hz, 2H), 6.60 (s, 1H), 4.28 (dd, J = 13.1, 4.8 Hz, 1H), 4.18 (dd, J = 13.1, 5.4 Hz, 1H), 4.00 (dd, J = 13.1, 4.4 Hz, 1H), 3.93 (dd, J = 13.1, 6.8 Hz, 1H), 2.65 (d, J = 4.8 Hz, 3H); $^{13}$C NMR (101 MHz) δ 196.80, 139.80, 139.51, 138.43, 136.63, 135.65, 135.56, 132.63, 131.99, 131.52, 130.44, 129.62, 129.37, 129.30, 128.83, 128.73, 128.48, 60.37, 53.94, 39.65. | $C_{26}H_{25}ClNO$ 402.16192 | 402.16098 |
| JN019 | $^1$H NMR δ 12.62 (m, 1H), 7.63-7.57 (m, 2H), 7.48-7.41 (m, 3H), 7.40-7.29 (m, 6H), 7.22 (d, J = 8.2 Hz, 2H), 7.17-7.09 (m, 3H), 6.71 (s, 1H), 4.16 (dd, J = 13.5, 3.9 Hz, 1H), 4.01 (dd, J = 13.0, 5.1 Hz, 1H), 3.93-3.84 (m, 2H), 2.47 (d, J = 3.6 Hz, 3H); $^{13}$C NMR δ 199.43, 141.78, 140.66, 137.01, 136.97, 134.66, 134.16, 131.43, 130.39, 130.11, 129.86, 129.58, 129.32, 129.10 (2C), 128.34, 126.22, 60.10, 51.44, 39.08. | $C_{26}H_{25}ClNO$ 402.16192 | 402.16128 |
| JN020 | $^1$H NMR (400 MHz) δ 12.63 (m, 1H), 7.63-7.57 (m, 2H), 7.48-7.43 (m, 3H), 7.40-7.30 (m, 8H), 7.10 (s, 1H), 7.07 (d, J = 8.4 Hz, 2H), 6.72 (s, 1H), 4.19-4.11 (m, 1H), 4.01 (dd, J = 12.9, 5.3 Hz, 1H), 3.93-3.86 (m, 2H), 2.47 (d, J = 4.0 Hz, 3H); $^{13}$C NMR (101 MHz, CDCl$_3$) δ 199.41, 141.83, 140.81, 136.98, 134.65, 132.07, 131.45, 130.42, 130.13, 129.61, 129.34, 129.13, 128.36, 126.23, 122.89, two low-field carbons not distinguishable due to low sample concentration, 60.13, 51.48, 39.11. | $C_{26}H_{25}BrNO$ 446.11140 | 446.10903 |
| JN021 | $^1$H NMR (400 MHz) δ 12.75 (m, 1H), 7.69-7.63 (m, 2H), 7.48-7.43 (m, 3H), 7.41-7.34 (m, 4H), 7.31 (d, J = 8.6 Hz, 2H), 7.19-7.14 (m, 2H), 7.12 (s, 1H), 6.97 (d, J = 8.6 Hz, 2H), 6.59 (s, 1H), 4.28 (dd, J = 13.1, 4.7 Hz, 1H), 4.19 (dd, J = 13.0, 5.3 Hz, 1H), 4.00 (dd, J = 13.1, 4.2 Hz, 1H), 3.93 (dd, J = 13.2, 6.8 Hz, 1H), 2.65 (d, J = 4.6 Hz, 3H); $^{13}$C NMR (101 MHz) δ 196.75, 139.71, 139.63, 138.44, 136.64, 135.53, 133.07, 132.15, 131.78, 131.51, 130.41, 129.59, 129.35, 129.26, 128.72, 128.50, 124.03, 60.37, 53.92, 39.66. | $C_{26}H_{25}BrNO$ 446.11140 | 446.10948 |
| JN022 | $^1$H NMR (400 MHz) δ 7.82 (d, J = 8.0 Hz, 2H), 7.59-7.49 (m, 5H), 7.46 (t, J = 7.5 Hz, 2H), 7.32-7.20 (m, 5H), 7.17 (s, 1H), 3.60 (s, 2H), 3.52 (s, 2H), 2.17 (s, 3H); $^{13}$C NMR (101 MHz) δ 198.48, 142.23, 139.84, 138.98, 137.98, 134.30, 132.36, 131.97, 131.77, 129.75, 129.17, 128.51, 128.37, 127.17, 123.49, 62.36, 54.04, 42.23. | $C_{24}H_{23}BrNO$ 420.09575 | 420.09344 |
| JN023 | $^1$H NMR (400 MHz) δ 12.54 (m, 1H), 7.40-7.30 (m, 5H), 7.28-7.25 (m, 2H), 7.18 (d, J = 0.9 Hz, 1H), 7.14-7.10 (m, 3H), 6.66 (d, J = 0.8 Hz, 1H), 3.91 (s, 2H), 2.67 (s, 6H); $^{13}$C NMR (101 MHz) δ 199.29, 140.87, 140.50, 137.15, 136.98, 134.67, 134.18, 131.59, 130.23, 129.85, 129.33, 129.12, 126.21, 53.42, 42.78. | $C_{20}H_{21}ClNO$ 326.13062 | 326.13034 |
| JN024 | $^1$H NMR δ 7.87-7.83 (m, 2H), 7.60-7.54 (m, 3H), 7.47 (dd, J = 8.4, 7.0 Hz, 2H), 7.38 (d, J = 8.5 Hz, 2H), 7.20 (s, 1H), 3.46 (s, 2H), 2.29 (s, 6H); $^{13}$C NMR δ 198.29, two low-field carbons not distinguishable due to low sample concentration, 137.89, 135.24, 133.82, 132.47, 131.68, 129.94, 128.90, 128.53, 55.32, 45.54. | $C_{18}H_{19}ClNO$ 300.11497 | 300.11357 |
| JN025 | $^1$H NMR δ 7.42-7.29 (m, 5H), 7.26 (d, J = 8.5 Hz, 2H), 7.18 (d, J = 8.5 Hz, 2H), 7.02 (s, 1H), 5.99 (s, 1H), 5.81 (s, 1H), 1.94 (s, 3H); $^{13}$C NMR δ 201.53, 144.39, 141.85, 138.18, 134.58, 133.96, 130.30, 129.95, 128.99, 128.86, 128.49, 128.38, 126.31, 16.96. | $C_{18}H_{16}ClO$ 283.08842 | 283.08642 |

TABLE 2-continued

Physical Properties of Synthesized Compounds

| Compound No. | NMR[1] | Formula[2] m/z (calc.) | m/z (meas.) |
|---|---|---|---|
| JN026 | $^1$H NMR (400 MHz) δ 7.77-7.71 (m, 2H), 7.58-7.52 (m, 1H), 7.49-7.43 (m, 2H), 7.41-7.32 (m, 4H), 7.11 (q, J = 1.5 Hz, 1H), 2.25 (d, J = 1.5 Hz, 3H); $^{13}$C NMR (101 MHz) δ 199.27, 140.64, 138.40, 137.54, 134.62, 134.34, 131.93, 131.04, 129.60, 128.86, 128.39, 14.62. | $C_{16}H_{14}ClO$ 257.07277 | 257.07081 |
| JN027 | Purity >80%. $^1$H NMR (400 MHz) δ 7.87-7.81 (m, 2H), 7.57-7.51 (m, 3H), 7.46 (dd, J = 8.2, 6.8 Hz, 2H), 7.36 (d, J = 8.6 Hz, 2H), 7.11 (s, 1H), 3.60 (s, 2H), 2.37 (t, J = 7.4 Hz, 4H), 1.39-1.07 (m, 16H), 0.84 (t, J = 7.0 Hz, 6H); $^{13}$C NMR δ 198.66, impurity peak overlap in the aromatic region, 53.78, 51.37, 31.92, 27.33, 26.44, 22.78, 14.19. | $C_{28}H_{39}ClNO$ 440.27147 | 440.26916 |
| JN028 | $^1$H NMR (400 MHz) δ 7.88-7.82 (m, 2H), 7.62-7.53 (m, 3H), 7.51-7.43 (m, 2H), 7.37 (d, J = 8.5 Hz, 2H), 7.13 (s, 1H), 3.61 (s, 2H), 2.60-2.52 (m, 4H), 1.82-1.72 (m, 4H); $^{13}$C NMR (101 MHz) δ 198.42, 142.07, 139.95, 138.11, 135.06, 134.04, 132.34, 131.76, 129.94, 128.79, 128.46, 54.05, 51.71, 23.80. | $C_{20}H_{21}ClNO$ 326.13062 | 326.12820 |
| JN029 | $^1$H NMR (400 MHz) δ 7.84-7.78 (m, 2H), 7.61-7.53 (m, 3H), 7.47 (t, J = 7.5 Hz, 2H), 7.38 (d, J = 8.5 Hz, 2H), 7.22 (s, 1H), 3.69-3.63 (m 4H), 3.51 (s, 2H), 2.51-2.44 (m, 4H); $^{13}$C NMR (101 MHz) δ 198.29, 142.80, 138.68, 137.97, 135.28, 133.85, 132.41, 131.64, 129.70, 128.85, 128.54, 67.15, 54.66, 53.53. | $C_{20}H_{21}ClNO_2$ 342.12553 | 342.12403 |
| JN030 | $^1$H NMR (400 MHz) δ 7.84-7.79 (m, 2H), 7.69-7.62 (m, 2H), 7.59-7.52 (m, 1H), 7.49-7.43 (m, 2H), 7.32-7.23 (m, 5H), 7.22 (s, 1H), 7.06 (t, J = 8.7 Hz, 2H), 3.62 (s, 2H), 3.54 (s, 2H), 2.19 (s, 3H); $^{13}$C NMR (101 MHz) δ 198.66, 163.20 (d, J = 250.4 Hz), 142.90, 139.08, 138.82 (d, J = 1.4 Hz), 138.19, 132.55 (d, J = 8.3 Hz), 132.26, 131.56 (d, J = 3.3 Hz), 129.77, 129.23, 128.48, 128.37, 127.18, 115.65 (d, J = 21.5 Hz), 62.40, 53.91, 42.28. | $C_{24}H_{23}FNO$ 360.17582 | 360.17402 |
| JN031 | $^1$H NMR (400 MHz) δ 7.94 (dt, J = 1.5, 0.7 Hz, 1H), 7.83-7.77 (m, 2H), 7.60-7.53 (m, 1H), 7.49-7.41 (m, 4H), 7.31-7.21 (m, 5H), 7.13 (s, 1H), 3.59 (s, 2H), 3.54 (s, 2H), 2.16 (s, 3H); $^{13}$C NMR (101 MHz) δ 198.18, 140.94, 140.73, 138.84, 137.74, 135.41, 133.22, 132.87, 132.52, 132.23, 130.53, 129.75, 129.60, 129.17, 128.57, 128.39, 127.22, 62.30, 54.16, 41.90. | $C_{24}H_{22}Cl_2NO$ 410.10730 | 410.10514 |
| JN032 | $^1$H NMR δ 7.37-7.31 (m, 3H), 7.21-7.17 (m, 2H), 7.14 (d, J = 8.6 Hz, 2H), 7.11 (s, 1H), 6.99 (d, J = 8.3 Hz, 2H), 5.84 (p, J = 1.0 Hz, 1H), 5.81 (p, J = 1.5 Hz, 1H), 2.00 (dd, J = 1.5, 0.9 Hz, 3H); $^{13}$C NMR δ 199.00, 144.31, 141.27, 136.37, 136.27, 134.63, 133.50, 131.51, 129.40, 129.01, 128.63, 128.20, 126.40, 18.76. | $C_{18}H_{16}ClO$ 283.08842 | 283.08634 |
| JN033 | $^1$H NMR δ 7.33-7.28 (m, 3H), 7.15-7.11 (m, 2H), 7.06 (d, J = 8.6 Hz, 2H), 6.87 (d, J = 8.7 Hz, 2H), 6.71 (s, 1H), 4.91 (s, 2H), 4.89 (d, J = 4.8 Hz, 1H), 1.86 (d, J = 4.4 Hz, 1H), 1.78 (s, 3H); $^{13}$C NMR δ 144.51, 142.89, 137.97, 135.11, 132.63, 130.65, 129.24, 128.77, 128.25, 127.77, 126.62, 113.26, 80.62, 18.43. | $[M - OH]^+$ $C_{18}H_{16}Cl$ 267.09350 | 267.09195 |
| JN034 | $^1$H NMR δ 7.57-7.53 (m, 2H), 7.36-7.34 (m, 4H), 7.34-7.29 (m, 3H), 6.87 (s, 1H), 5.26 (d, J = 5.6 Hz, 1H), 5.10 (s, 1H), 4.95 (q, J = 1.6 Hz, 1H), 1.89 (d, J = 5.6 Hz, 1H), 1.63 (d, J = 1.4 Hz, 3H); $^{13}$C NMR δ 145.63, 142.52, 139.65, 135.44, 133.31, 131.82, 130.31, 128.74, 128.33, 128.21, 127.77, 111.38, 73.15, 20.10. | $[M - OH]^+$ $C_{18}H_{16}Cl$ 267.09350 | 267.09213 |

TABLE 2-continued

Physical Properties of Synthesized Compounds

| Compound No. | NMR[1] | Formula[2] m/z (calc.) | m/z (meas.) |
|---|---|---|---|
| JN035 | $^1$H NMR δ 7.84 (d, J = 7.7 Hz, 2H), 7.59-7.50 (m, 3H), 7.47 (t, J = 7.7 Hz, 2H), 7.36 (d, J = 8.5 Hz, 2H), 7.13 (s, 1H), 3.58 (s, 2H), 2.05 (d, J = 7.1 Hz, 4H), 1.66 (m, 2H), 0.77 (d, J = 6.6 Hz, 12H); $^{13}$C NMR δ 198.42, 141.15, 140.08, 137.94, 134.70, 134.06, 132.38, 131.36, 129.72, 128.71, 128.45, 64.20, 53.06, 26.35, 21.23. | $C_{24}H_{31}ClNO$ 384.20887 | 384.20656 |
| JN036 | $^1$H NMR (400 MHz) δ 7.84 (dt, J = 7.0, 1.4 Hz, 2H), 7.58-7.52 (m, 1H), 7.46 (ddt, J = 8.3, 6.6, 1.2 Hz, 2H), 7.41-7.33 (m, 4H), 6.97 (s, 1H), 3.67 (d, J = 1.3 Hz, 2H), 2.93 (septet, J = 6.7 Hz, 2H), 0.81 (d, J = 6.7 Hz, 12H); $^{13}$C NMR (101 MHz) δ 199.32, 143.85, 138.26, 135.85, 134.31, 134.10, 132.36, 130.89, 129.42, 128.63, 128.42, 47.10, 42.58, 20.37. | $C_{22}H_{27}ClNO$ 356.17757 | 356.17594 |
| JN037 | $^1$H NMR δ 7.85-7.80 (m, 2H), 7.61 (d, J = 8.6 Hz, 2H), 7.58-7.54 (m, 1H), 7.47 (dd, J = 8.4, 7.0 Hz, 2H), 7.37 (d, J = 8.5 Hz, 2H), 7.16 (s, 1H), 3.44 (s, 2H), 2.48-2.35 (m, 4H), 1.52 (p, J = 5.6 Hz, 4H), 1.44-1.37 (m, 2H); $^{13}$C NMR δ 198.57, 142.23, 139.78, 138.16, 135.02, 134.12, 132.24, 131.87, 129.78, 128.73, 128.44, 55.04, 54.47, 26.23, 24.43. | $C_{21}H_{23}ClNO$ 340.14627 | 340.14391 |
| JN038 | $^1$H NMR (400 MHz) δ 7.83-7.78 (m, 2H), 7.60-7.53 (m, 3H), 7.50-7.44 (m, 2H), 7.37 (d, J = 8.5 Hz, 2H), 7.19 (s, 1H), 3.50 (s, 2H), 2.60-2.46 (m, 4H), 2.45-2.28 (m, 4H), 2.25 (s, 3H); $^{13}$C NMR (101 MHz) δ 198.37, 142.39, 139.23, 138.06, 135.14, 133.95, 132.33, 131.70, 129.72, 128.80, 128.49, 55.31, 54.19, 52.99, 46.16. | $C_{21}H_{24}ClN_2O$ 355.15717 | 355.15532 |
| JN039 | $^1$H NMR (400 MHz) δ 7.86-7.79 (m, 2H), 7.63-7.55 (m, 3H), 7.49 (ddt, J = 8.2, 6.6, 1.2 Hz, 2H), 7.41-7.36 (m, 2H), 7.24 (s, 1H), 6.99-6.89 (m, 2H), 6.87-6.80 (m, 2H), 3.57 (s, 2H), 3.11-3.03 (m, 4H), 2.68-2.61 (m, 4H); $^{13}$C NMR (101 MHz) δ 198.38, carbon directly attached to F not distinguishable from noise due to low concentration), 148.09 (d, J = 2.3 Hz), 142.68, 138.92, 138.04, 135.26, 133.89, 132.41, 131.69, 129.72, 128.86, 128.55, 117.89 (d, J = 7.6 Hz), 115.60 (d, J = 22.0 Hz), 54.24, 53.07, 50.34. | $C_{26}H_{25}ClFN_2O$ 435.16340 | 435.16123 |
| JN040 | $^1$H NMR (400 MHz) δ 7.96 (t, J = 1.8 Hz, 1H), 7.85-7.79 (m, 2H), 7.59-7.54 (m, 1H), 7.54-7.43 (m, 4H), 7.30-7.19 (m, 6H), 7.17 (s, 1H), 3.62 (s, 2H), 3.54 (s, 2H), 2.15 (s, 3H); $^{13}$C NMR (101 MHz) δ 198.35, 141.61, 140.57, 138.98, 137.86, 137.52, 133.19, 132.44, 131.90, 130.05, 129.76, 129.17, 128.84, 128.53, 128.33, 127.12, 122.76, 62.27, 54.27, 41.89. | $C_{24}H_{23}BrNO$ 420.09575 | 420.09355 |
| JN041 | $^1$H NMR δ 12.95 (m, 1H), 8.10 (d, J = 7.8 Hz, 2H), 7.82 (dd, J = 7.7, 1.7 Hz, 1H), 7.68-7.59 (m, 4H), 7.59-7.52 (m, 3H), 7.41-7.36 (m, 3H), 7.34 (t, J = 7.6 Hz, 1H), 7.22 (td, J = 7.8, 1.7 Hz, 1H), 4.21 (dd, J = 13.1, 4.7 Hz, 1H), 4.18-4.11 (m, 2H), 4.03 (dd, J = 13.0, 5.9 Hz, 1H), 2.62 (d, J = 4.7 Hz, 3H); $^{13}$C NMR δ 196.65, 149.85, 136.02, 133.86, 133.72, 132.98, 131.73, 131.46, 131.15, 130.85, 130.43, 130.28, 129.45, 129.08, 128.55, 128.39, 123.22, 60.78, 49.38, 41.09. | $C_{24}H_{23}BrNO$ 420.09575 | 420.09567 |
| JN042 | $^1$H NMR (400 MHz) δ 12.95 (m, 1H), 8.11 (d, J = 7.1 Hz, 2H), 7.92 (d, J = 7.6 Hz, 1H), 7.68-7.58 (m, 3H), 7.59-7.50 (m, 3H), 7.46-7.33 (m, 4H), 7.17 (t, J = 7.9 Hz, 1H), 4.31 (dd, J = 12.9, 3.5 Hz, 1H), 4.11 (dd, J = 13.1, 6.7 Hz, 1H), 4.06-3.97 (m, 2H), 2.68 (d, J = 4.0 Hz, 3H); $^{13}$C NMR (101 MHz) δ 196.59, 146.81, 135.88, 133.95, 133.88, 133.61, 132.73, 131.50, 131.35, 131.26, 130.55, 130.35, 129.43, 129.23, 129.12, 128.45, 128.22, 61.38, 49.54, 42.00. | $C_{24}H_{22}Cl_2NO$ 410.10730 | 410.10514 |

TABLE 2-continued

Physical Properties of Synthesized Compounds

| Compound No. | NMR[1] | Formula[2] m/z (calc.) | m/z (meas.) |
|---|---|---|---|
| JN043 | $^1$H NMR δ 7.81 (d, J = 7.6 Hz, 2H), 7.59-7.52 (m, 3H), 7.45 (t, J = 7.6 Hz, 2H), 7.30-7.18 (m, 8H), 3.65 (s, 2H), 3.54 (s, 2H), 2.39 (s, 3H), 2.17 (s, 3H); $^{13}$C NMR δ 198.92, 144.20, 139.37, 139.31, 138.42, 138.36, 132.64, 132.10, 130.56, 129.77, 129.34, 129.17, 128.40, 128.31, 127.04, 62.28, 54.12, 42.12, 21.56. | $C_{25}H_{26}NO$ 356.20089 | 356.19927 |
| JN044 | $^1$H NMR (400 MHz) δ 7.87-7.83 (m, 2H), 7.72 (d, J = 8.3 Hz, 2H), 7.62 (d, J = 8.2 Hz, 2H), 7.60-7.55 (m, 1H), 7.50-7.44 (m, 2H), 7.30-7.17 (m, 6H), 3.61 (s, 2H), 3.51 (s, 2H), 2.17 (s, 3H); $^{13}$C NMR δ 198.28, 141.43, 140.86, 138.92, 138.83, 137.67, 132.60, 130.58 (q, J = 32.5 Hz), 130.41, 129.77, 129.15, 128.58, 128.38, 127.21, 125.45 (q, J = 3.8 Hz), 124.13 (q, J = 272.2 Hz), 62.41, 54.12, 42.33. | $C_{25}H_{23}F_3NO$ 410.17263 | 410.17055 |
| JN045 | $^1$H NMR δ 12.97 (m, 1H), 8.10 (d, J = 7.4 Hz, 2H), 7.96 (d, J = 8.3 Hz, 1H), 7.66-7.60 (m, 3H), 7.58-7.51 (m, 3H), 7.47-7.37 (m, 3H), 7.30 (d, J = 2.0 Hz, 1H), 7.18 (dd, J = 8.4, 2.0 Hz, 1H), 4.35 (dd, J = 12.9, 3.6 Hz, 1H), 4.10 (d, J = 13.0, 1H), 4.01-3.94 (m, 2H), 2.71 (d, J = 4.7 Hz, 3H); $^{13}$C NMR δ 196.72, 146.42, 136.30, 135.94, 133.90, 133.86, 132.76, 131.93, 131.59, 130.59, 130.38, 130.25, 129.57, 129.55, 129.15, 128.46, 128.05, 61.61, 49.39, 42.25. | $C_{24}H_{22}Cl_2NO$ 410.10730 | 410.10490 |
| JN046 | $^1$H NMR (400 MHz) δ 12.98 (m, 1H), 8.09 (d, J = 7.6 Hz, 2H), 7.91-7.82 (m, 1H), 7.72-7.60 (m, 4H), 7.59-7.52 (m, 2H), 7.43-7.33 (m, 4H), 7.31-7.27 (m, 2H), 4.25 (dd, J = 13.1, 4.4 Hz, 1H), 4.15 (d, J = 4.4 Hz, 2H), 4.04 (dd, J = 13.1, 5.9 Hz, 1H), 2.64 (d, J = 4.6 Hz, 3H); $^{13}$C NMR δ 196.78, 147.99, 136.07, 133.75, 133.36, 132.00, 131.96, 131.51, 131.06, 130.81, 130.47, 130.32, 129.82, 129.48, 129.10, 128.54, 127.78, 60.97, 49.55, 41.31. | $C_{24}H_{23}ClNO$ 376.14627 | 376.14607 |
| JN047 | $^1$H NMR δ 7.84 (dd, J = 7.8, 1.5 Hz, 2H), 7.63 (d, J = 7.0 Hz, 2H), 7.55 (t, J = 7.3 Hz, 1H), 7.45 (t, J = 7.6 Hz, 2H), 7.42-7.34 (m, 3H), 7.29-7.21 (m, 6H), 3.65 (s, 2H), 3.53 (s, 2H), 2.17 (s, 3H); $^{13}$C NMR δ 198.80, 143.43, 139.34, 139.19, 138.20, 135.46, 132.25, 130.38, 129.78, 129.18, 129.02, 128.57, 128.45, 128.31, 127.07, 62.33, 54.15, 42.21. | $C_{24}H_{24}NO$ 342.18524 | 342.18365 |
| JN048 | $^1$H NMR δ 7.84-7.79 (m, 3H), 7.56 (t, J = 7.4 Hz, 1H), 7.49-7.43 (m, 3H), 7.37-7.29 (m, 2H), 7.28-7.20 (m, 5H), 7.18 (s, 1H), 3.62 (s, 2H), 3.54 (s, 2H), 2.15 (s, 3H); $^{13}$C NMR δ 198.38, 141.72, 140.50, 138.96, 137.85, 137.21, 134.59, 132.44, 130.29, 129.78, 129.76, 129.18, 128.99, 128.52, 128.40, 128.33, 127.13, 62.32, 54.26, 41.88. | $C_{24}H_{23}ClNO$ 376.14627 | 376.14428 |
| JN049 | $^1$H NMR δ 7.92-7.88 (m, 2H), 7.60-7.54 (m, 2H), 7.47 (t, J = 7.7 Hz, 2H), 7.29-7.24 (m, 3H), 7.24-7.18 (m, 4H), 7.16-7.11 (m, 2H), 3.55 (s, 2H), 3.44 (s, 2H), 2.25 (s, 3H), 2.10 (s, 3H); $^{13}$C NMR δ 198.68, 140.37, 140.33, 139.15, 138.10, 136.86, 134.75, 132.41, 130.15, 129.83, 129.70, 129.00, 128.69, 128.47, 128.22, 126.96, 125.83, 62.21, 54.32, 42.18, 20.28. | $C_{25}H_{26}NO$ 356.20089 | 356.19898 |
| JN050 | $^1$H NMR δ 7.73 (d, J = 8.5 Hz, 2H), 7.56 (d, J = 8.5 Hz, 2H), 7.42 (d, J = 8.5 Hz, 2H), 7.35 (d, J = 8.5 Hz, 2H), 7.29-7.22 (m, 3H), 7.22-7.17 (m, 3H), 7.14 (s, 1H), 3.58 (s, 2H), 3.50 (s, 2H), 2.16 (s, 3H); $^{13}$C NMR δ 197.28, 141.97, 139.62, 138.84, 138.75, 136.28, 135.28, 133.63, 131.73, 131.05, 129.14, 128.87, 128.83, 128.39, 127.23, 62.41, 54.04, 42.38. | $C_{24}H_{22}Cl_2NO$ 410.10730 | 410.10412 |

TABLE 2-continued

Physical Properties of Synthesized Compounds

| Compound No. | NMR[1] | Formula[2] m/z (calc.) | m/z (meas.) |
|---|---|---|---|
| JN051 | Mixture of E and the Z isomers. Only the key and/or distinguishable peaks highlighted. $^1$H NMR (500 MHz, Chloroform-d) δ 7.72 (s, 2.6H), 7.69 (s, 1H), 7.52 (d, J = 16.1 Hz, 1H), 6.80 (d, J = 15.7 Hz, 1.8H), 6.69 (d, J = 16.1 Hz, 1H); $^{13}$C NMR (126 MHz, CDCl$_3$) δ 198.99, 190.38. | $C_{23}H_{17}F_2O$ 347.12420 | N/A[3] |
| JN054 | $^1$H NMR δ 12.71 (m, 1H), 7.69-7.62 (m, 2H), 7.49-7.41 (m, 4H), 7.41-7.32 (m, 3H), 7.19-7.13 (m, 2H), 7.13-7.06 (m, 3H), 6.86 (t, J = 8.7 Hz, 2H), 6.57 (s, 1H), 4.29 (dd, J = 13.1, 3.8 Hz, 1H), 4.19 (dd, J = 13.0, 4.3 Hz, 1H), 4.00 (dd, J = 13.3, 3.3 Hz, 1H), 3.94 (dd, J = 13.0, 5.7 Hz, 1H), 2.65 (d, J = 3.1 Hz, 3H); $^{13}$C NMR δ 196.84, 163.25 (d, J = 251.8 Hz), 140.38, 138.69 (d, J = 1.9 Hz), 137.99, 136.68, 135.68, 132.85 (d, J = 8.4 Hz), 131.49, 130.37, 130.31, 130.28, 129.57, 129.36, 129.33, 128.60, 115.69 (d, J = 21.6 Hz), 60.31, 54.06, 39.63. | $C_{26}H_{25}FNO$ 386.19147 | 386.19061 |
| JN055 | Purity >85%. $^1$H NMR δ 12.59 (m, 1H), 7.63-7.56 (m, 2H), 7.48-7.42 (m, 3H), 7.41-7.30 (m, 6H), 7.20-7.15 (m, 2H), 7.14 (s, 1H), 6.94 (t, J = 8.6 Hz, 2H), 6.73 (s, 1H), 4.17 (dd, J = 13.1, 4.0 Hz, 1H), 4.02 (dd, J = 13.1, 5.3 Hz, 1H), 3.95-3.85 (m, 2H), 2.46 (d, J = 3.9 Hz, 3H); $^{13}$C NMR δ 199.62, 162.64 (d, J = 250.0 Hz), overlap of impurity peaks, 115.97 (d, J = 21.83 Hz), 60.12, 51.44, 39.03. | $C_{26}H_{25}FNO$ 386.19147 | 386.19048 |
| JN056 | $^1$H NMR δ 12.53 (m, 1H), 7.62- 7.57 (m, 2H), 7.47-7.42 (m, 3H), 7.39-7.29 (m, 6H), 7.16 (s, 1H), 7.12 (d, J = 8.7 Hz, 2H), 6.75 (d, J = 8.7 Hz, 2H), 6.74 (s, 1H), 4.16 (dd, J = 13.0, 4.3 Hz, 1H), 4.00-3.91 (m, 3H), 3.70 (s, 3H), 2.49 (d, J = 4.7 Hz, 3H); $^{13}$C NMR δ 200.25, 159.88, 141.13, 138.19, 137.59, 137.17, 131.43 (2C), 130.31, 130.09, 129.53, 129.20, 128.62, 128.53, 128.30, 126.20, 114.27, (one low-field carbon is overlapped), 59.87, 55.34, 51.69, 39.15. | $C_{27}H_{28}NO_2$ 398.21200 | 398.21098 |
| JN057 | $^1$H NMR δ 12.77 (m, 1H), 7.68-7.62 (m, 2H), 7.48-7.41 (m, 3H), 7.41-7.34 (m, 3H), 7.31 (s, 1H), 7.23 (d, J = 8.4 Hz, 1H), 7.19-7.14 (m, 3H), 7.12 (s, 1H), 6.92 (dd, J = 8.4, 2.1 Hz, 1H), 6.59 (s, 1H), 4.27 (dd, J = 13.1, 4.7 Hz, 1H), 4.19 (dd, J = 13.1, 5.2 Hz, 1H), 4.00 (dd, J = 13.1, 4.1 Hz, 1H), 3.92 (dd, J = 13.0, 6.7 Hz, 1H), 2.65 (d, J = 4.6 Hz, 3H); $^{13}$C NMR δ 196.46, 140.61, 138.86, 137.79, 136.58, 135.05, 134.20, 133.53, 132.73, 132.19, 131.50, 130.44, 130.43, 129.69, 129.60, 129.45, 129.12, 128.97, 128.44, 60.41, 53.74, 39.71. | $C_{26}H_{24}Cl_2NO$ 436.12295 | 436.12196 |
| JN058 | $^1$H NMR δ 12.69 (m, 1H), 7.63-7.59 (m, 2H), 7.48-7.43 (m, 4H), 7.40-7.30 (m, 6H), 7.27 (d, J = 2.0 Hz, 1H), 7.09-7.04 (m, 2H), 6.71 (s, 1H), 4.17 (dd, J = 13.1, 4.4 Hz, 1H), 4.05 (dd, J = 12.9, 5.7 Hz, 1H), 3.97-3.85 (m, 2H), 2.51 (d, J = 4.6 Hz, 3H); $^{13}$C NMR δ 199.16, 141.96, 141.78, 137.01, 136.68, 135.61, 133.01, 132.85, 131.47, 130.98, 130.45, 130.04, 129.61, 129.41, 129.38, 128.62, 128.28, 127.95, 126.24, 60.25, 51.37, 39.08. | $C_{26}H_{24}Cl_2NO$ 436.12295 | 436.12192 |
| JN059 | $^1$H NMR δ 12.78 (m, 1H), 7.68-7.63 (m, 2H), 7.47-7.43 (m, 3H), 7.38 (d, J = 7.9 Hz, 2H), 7.33 (s, 1H), 7.30-7.27 (m, 3H), 7.19-7.11 (m, 3H), 6.94 (td, J = 7.6, 1.2 Hz, 1H), 6.83 (d, J = 7.8, 1.6 Hz, 1H), 6.79 (s, 1H), 4.31 (dd, J = 13.1, 4.6 Hz, 1H), 4.16 (dd, J = 13.1, 5.6 Hz, 1H), 4.03 (dd, J = 13.2, 4.6 Hz, 1H), 3.98 (dd, J = 13.1, 6.5 Hz, 1H), 2.64 (d, J = 4.8 Hz, 3H); $^{13}$C NMR δ 196.83, 140.71, 139.92, 136.56, 135.88, 134.84, 134.77, 133.19, | $C_{26}H_{25}ClNO$ 402.16192 | 402.15995 |

TABLE 2-continued

Physical Properties of Synthesized Compounds

| Compound No. | NMR[1] | Formula[2] m/z (calc.) | m/z (meas.) |
|---|---|---|---|
| | 131.50, 131.10, 130.37, 130.12, 129.69, 129.57, 129.41, 128.95, 128.63, 128.52, 126.49, 60.13, 53.22, 39.21. | | |
| JN060 | $^1$H NMR δ 12.80 (m, 1H), 7.69-7.62 (m, 2H), 7.48-7.43 (m, 3H), 7.40-7.35 (m, 3H), 7.30 (s, 1H), 7.22-7.15 (m, 4H), 7.11 (t, J = 7.9 Hz, 1H), 7.05 (t, J = 1.9 Hz, 1H), 6.99 (dt, J = 7.8, 1.4 Hz, 1H), 6.63 (s, 1H), 4.28 (dd, J = 13.2, 4.7 Hz, 1H), 4.18 (dd, J = 13.1, 5.3 Hz, 1H), 4.00 (dd, J = 13.2, 4.3 Hz, 1H), 3.93 (dd, J = 13.0, 6.7 Hz, 1H), 2.64 (d, J = 4.5 Hz, 3H); $^{13}$C NMR δ 196.71, 140.30, 138.88, 138.77, 136.57, 135.96, 135.29, 134.40, 131.50, 130.41, 130.36, 129.72, 129.60, 129.48, 129.34, 129.20, 128.83, 128.76, 128.48, 60.34, 53.69, 39.57. | $C_{26}H_{25}ClNO$ 402.16192 | 402.15993 |
| JN061 | 1:0.4 E:Z isomer mixture. $^1$H NMR δ 12.69 (overlapped, m, 1.4H), 7.73-7.67 (Z, m, 0.8H), 7.67-7.62 (E, m, 2H), 7.49-7.28 (overlapped region), 7.21 (E, d, J = 7.1 Hz, 2H), 7.16 (Z, d, J = 1.8 Hz, 0.4H), 7.11 (E, s, 1H), 6.83 (Z, s, 0.4H), 6.72 (Z, s, 0.4 H), 6.50 (E, s, 1H), 6.44 (Z, d, J = 3.4 Hz, 0.4 H), 6.38 (Z, dd, J = 3.5, 1.8 Hz, 0.4 H), 6.30 (E, dd, J = 3.7, 1.7 Hz, 1H), 5.93 (E, d, J = 3.6 Hz, 1H), 4.48-3.86 (overlapped, m, 5.6H), 2.70 (Z, d, J = 3.9 Hz, 1.2H), 2.65 (E, d, J = 4.0 Hz, 3H); $^{13}$C NMR δ 198.78 (Z), 195.60 (E), overlap in aromatic region, 60.15 (E), 59.90 (Z), 54.39 (E), 51.79 (Z), 39.43 (E), 39.23 (Z). | $C_{24}H_{24}NO_2$ 358.18016 | 358.17818 |
| JN062 | $^1$H NMR δ 12.72 (m, 1H), 7.69-7.62 (m, 2H), 7.47-7.42 (m, 3H), 7.41 (s, 1H), 7.39-7.33 (m, 3H), 7.25-7.21 (m, 1H), 7.21-7.14 (m, 5H), 7.10 (d, J = 7.7 Hz, 2H), 6.62 (s, 1H), 4.30 (dd, J = 13.1, 4.4 Hz, 1H), 4.18 (dd, J = 13.1, 5.3 Hz, 1H), 4.01 (dd, J = 13.1, 4.2 Hz, 1H), 3.95 (dd, J = 13.1, 6.5 Hz, 1H), 2.65 (d, J = 4.3 Hz, 3H); $^{13}$C NMR δ 197.04, 141.23, 138.98, 138.21, 136.65, 135.90, 134.08, 131.50, 130.79, 130.34, 129.70, 129.55, 129.39, 129.20, 128.54, 128.52, 128.49, 60.23, 53.90, 39.47. | $C_{26}H_{26}NO$ 368.20089 | 368.19980 |
| JN063 | Purity >88%. $^1$H NMR δ 12.55 (m, 1H), 7.62-7.57 (m, 2H), 7.46-7.42 (m, 3H), 7.40-7.30 (m, 7H), 7.25-7.14 (m, 5H), 6.72 (s, 1H), 4.14 (dd, J = 13.1, 4.5 Hz, 1H), 3.97 (dd, J = 13.0, 5.9 Hz, 1H), 3.93-3.84 (m, 2H), 2.41 (d, J = 4.7 Hz, 3H); $^{13}$C NMR δ 199.82, impurity overlap in the aromatic region, 60.02, 51.54, 39.00. | $C_{26}H_{26}NO$ 368.20089 | 368.19978 |
| JN064 | $^1$H NMR δ 12.77 (m, 1H), 7.68-7.63 (m, 2H), 7.47-7.44 (m, 3H), 7.42 (d, J = 8.4 Hz, 2H), 7.39 (s, 1H), 7.38-7.34 (m, 3H), 7.21 (d, J = 8.2 Hz, 2H), 7.19-7.14 (m, 3H), 6.63 (s, 1H), 4.28 (d, J = 13.9 Hz, 1H), 4.20 (d, J = 14.0 Hz, 1H), 4.01 (d, J = 13.7 Hz, 1H), 3.94 (d, J = 13.2 Hz, 1H), 2.65 (s, 3H); $^{13}$C NMR δ 196.65, 141.08, 139.09, 138.25, 137.72, 136.59, 135.17, 131.48, 130.89 (q, J = 32.7 Hz), 130.70, 130.39, 129.58, 129.38, 129.18, 128.89, 128.47, 125.37 (q, J = 3.8 Hz), 123.85 (q, J = 272.2 Hz), 60.39, 53.62, 39.68. | $C_{27}H_{26}F_3NO$ 436.18828 | 436.18597 |
| JN065 | $^1$H NMR δ 12.68 (m, 1H), 7.61-7.56 (m, 2H), 7.52 (d, J = 8.1 Hz, 2H), 7.47-7.43 (m, 3H), 7.42-7.34 (m, 6H), 7.32 (d, J = 8.0 Hz, 2H), 7.18 (s, 1H), 6.73 (s, 1H), 4.14 (dd, J = 13.0, 4.5 Hz, 1H), 4.02 (dd, J = 13.0, 5.7 Hz, 1H), 3.93-3.84 (m, 2H), 2.44 (d, J = 4.7 Hz, 3H); $^{13}$C NMR δ 199.03, 142.18, 142.15, 139.25, 136.95, 136.68, 131.42, 130.46, 130.46 (q, J = 32.8 Hz), 129.68, 129.60, 129.42, 129.41, 128.86, 128.23, 126.27, 125.82 (q, J = 3.8 Hz), 123.81 (q, J = 272.3 Hz), 60.19, 51.31, 39.02. | $C_{27}H_{25}F_3NO$ 436.18828 | 436.18596 |

TABLE 2-continued

Physical Properties of Synthesized Compounds

| Compound No. | NMR[1] | Formula[2] m/z (calc.) | m/z (meas.) |
|---|---|---|---|
| JN066 | $^1$H NMR δ 12.68 (m, 1H), 7.69-7.63 (m, 2H), 7.47-7.42 (m, 4H), 7.41-7.32 (m, 3H), 7.20-7.15 (m, 2H), 7.13 (s, 1H), 6.98 (s, 4H), 6.58 (s, 1H), 4.30 (dd, J = 13.2, 4.4 Hz, 1H), 4.18 (dd, J = 13.1, 5.2 Hz, 1H), 4.00 (dd, J = 13.2, 4.2 Hz, 1H), 3.95 (dd, J = 12.9, 6.4 Hz, 1H), 2.65 (d, J = 4.2 Hz, 3H), 2.28 (s, 3H); $^{13}$C NMR δ 197.03, 141.99, 140.32, 138.08, 137.67, 136.68, 136.17, 131.50, 131.23, 130.93, 130.32, 129.54, 129.44, 129.29, 129.20, 128.56, 128.38, 60.18, 54.10, 39.45, 21.52. | $C_{27}H_{28}NO$ 382.21654 | 382.21427 |
| JN067 | $^1$H NMR δ 12.53 (m, 1H), 7.61-7.56 (m, 2H), 7.47-7.42 (m, 3H), 7.39-7.31 (m, 6H), 7.20 (s, 1H), 7.07 (d, J = 8.0 Hz, 2H), 7.03 (d, J = 8.0 Hz, 2H), 6.73 (s, 1H), 4.10 (dd, J = 13.0, 4.3 Hz, 1H), 3.95-3.89 (m, 3H), 2.46 (d, J = 4.6 Hz, 3H), 2.20 (s, 3H); $^{13}$C NMR δ 200.06, 141.22, 139.20, 138.85, 137.42, 137.18, 133.01, 131.66, 131.40, 130.28, 129.56, 129.52, 129.21, 128.75, 128.58, 126.25, (one low-field carbon is overlapped), 59.77, 51.68, 39.16, 21.25. | $C_{27}H_{28}NO$ 382.21654 | 382.21436 |
| JN068 | $^1$H NMR δ 12.79 (m, 1H), 7.69-7.63 (m, 2H), 7.48-7.43 (m, 3H), 7.41-7.37 (m, 3H), 7.23-7.19 (m, 2H), 7.19-7.13 (m, 3H), 6.95 (d, J = 1.8 Hz, 2H), 6.62 (s, 1H), 4.32-4.24 (m, 1H), 4.19 (dd, J = 13.4, 4.8 Hz, 1H), 4.04-3.97 (m, 1H), 3.96-3.89 (m, 1H), 2.64 (d, J = 4.1 Hz, 3H); $^{13}$C NMR δ 196.36, 141.51, 139.36, 137.15, 136.68, 136.53, 135.03, 134.74, 131.50, 130.43, 129.60, 129.45, 129.12, 129.02, 128.60 (one low-field carbon is overlapped), 128.44, 60.43, 53.52, 39.66. | $C_{26}H_{24}Cl_2NO$ 436.12295 | 436.12319 |
| JN069 | $^1$H NMR δ 12.76 (m, 1H), 7.68-7.63 (m, 2H), 7.48-7.43 (m, 3H), 7.40-7.33 (m, 4H), 7.20-7.14 (m, 4H), 6.94 (dd, J = 8.6, 2.4 Hz, 2H), 6.72 (dt, J = 10.2, 2.1 Hz, 1H), 6.63 (s, 1H), 4.29 (dd, J = 13.1, 4.8 Hz, 1H), 4.18 (dd, J = 13.1, 5.4 Hz, 1H), 4.00 (dd, J = 13.2, 4.4 Hz, 1H), 3.94 (dd, J = 13.2, 6.8 Hz, 1H), 2.65 (d, J = 4.8 Hz, 3H). $^{13}$C NMR δ 196.76, 162.47 (q, J = 246.2 Hz), 140.13, 139.09 (q, J = 2.6 Hz), 138.80, 136.57, 136.27 (q, J = 7.8 Hz), 135.32, 131.50, 130.40, 130.04 (q, J = 8.4 Hz), 129.59, 129.35, 129.20, 128.82, 128.48, 126.80 (q, J = 2.9 Hz), 116.86 (q, J = 22.6 Hz), 116.55 (q, J = 21.4 Hz), 60.34, 53.73, 39.58. | $C_{26}H_{25}FNO$ 386.19147 | 386.18954 |
| JN070 | $^1$H NMR δ 12.64 (m, 1H), 7.65-7.59 (m, 2H), 7.48-7.43 (m, 3H), 7.42-7.35 (m, 4H), 7.35-7.30 (m, 4H), 7.18-7.14 (m, 2H), 7.12 (s, 1H), 6.69 (s, 1H), 4.16 (dd, J = 13.0, 4.6 Hz, 1H), 4.04 (dd, J = 13.0, 5.8 Hz, 1H), 3.98-3.85 (m, 2H), 2.49 (d, J = 4.9 Hz, 3H); $^{13}$C NMR δ 199.43, 141.39, 141.32, 137.86, 137.19, 136.89, 131.58, 131.51, 131.14, 130.55, 130.39, 129.63, 129.56, 129.33, 129.23, 128.39, 127.38, 126.31, 122.86, 60.25, 51.46, 39.05. | $C_{26}H_{25}BrNO$ 446.11140 | 446.11181 |
| JN071 | $^1$H NMR δ 12.76 (m, 1H), 7.68-7.62 (m, 2H), 7.49-7.41 (m, 3H), 7.41-7.32 (m, 4H), 7.29 (s, 1H), 7.21 (d, J = 1.7 Hz, 1H), 7.19-7.13 (m, 3H), 7.08-6.99 (m, 2H), 6.62 (s, 1H), 4.28 (dd, J = 13.1, 4.6 Hz, 1H), 4.19 (dd, J = 13.0, 5.2 Hz, 1H), 4.00 (dd, J = 13.2, 4.2 Hz, 1H), 3.94 (dd, J = 13.0, 6.6 Hz, 1H), 2.64 (d, J = 4.4 Hz, 3H); $^{13}$C NMR δ 196.66, 140.32, 138.86, 138.66, 136.57, 136.23, 135.26, 133.32, 132.36, 131.50, 130.39, 129.95, 129.58, 129.33, 129.19, 129.14, 128.82, 128.48, 122.48, 60.32, 53.68, 39.56. | $C_{26}H_{25}BrNO$ 446.11140 | 446.11180 |

TABLE 2-continued

Physical Properties of Synthesized Compounds

| Compound No. | NMR[1] | Formula[2] m/z (calc.) | m/z (meas.) |
|---|---|---|---|
| JN072 | $^1$H NMR δ 12.65 (m, 1H), 7.64-7.58 (m, 2H), 7.51-7.33 (m, 13H), 7.18 (s, 1H), 6.70 (s, 1H), 4.16 (dd, J = 13.0, 4.6 Hz, 1H), 4.05 (dd, J = 13.0, 5.7 Hz, 1H), 3.88 (dd, J = 13.4, 7.0 Hz, 1H), 3.83 (dd, J = 13.4, 4.8 Hz, 1H), 2.46 (d, J = 4.8 Hz, 3H); $^{13}$C NMR δ 199.35, 141.82, 141.71, 137.10, 136.81, 136.47, 131.96, 131.48, 131.15 (q, J = 32.4 Hz), 130.42, 129.67, 129.58, 129.56, 129.39, 129.34, 128.26, 126.28, 125.21 (q, J = 3.7 Hz), 124.99 (q, J = 3.7 Hz), 123.8 (q, J = 272.6 Hz), 60.34, 51.27, 38.92. | $C_{27}H_{25}F_3NO$ 436.18828 | 436.18593 |
| JN073 | $^1$H NMR δ 12.80 (m, 1H), 7.69-7.64 (m, 2H), 7.49-7.43 (m, 4H), 7.39 (s, 1H), 7.38-7.36 (m, 3H), 7.32-7.29 (m, 3H), 7.19-7.15 (m, 3H), 6.64 (s, 1H), 4.29 (dd, J = 13.1, 4.6 Hz, 1H), 4.20 (dd, J = 13.1, 5.2 Hz, 1H), 4.01 (dd, J = 13.2, 4.1 Hz, 1H), 3.94 (dd, J = 13.1, 6.7 Hz, 1H), 2.65 (d, J = 4.4 Hz, 3H); $^{13}$C NMR δ 196.59, 140.74, 138.98, 138.44, 136.58, 135.14, 134.95, 133.75, 131.50, 130.91 (q, J = 32.4 Hz), 130.41, 129.59, 129.42, 129.12, 129.01, 128.91, 128.48, 127.12 (q, J = 3.9 Hz), 125.90 (q, J = 3.6 Hz), 123.70 (q, J = 272.4 Hz), 60.37, 53.65, 39.63. | $C_{27}H_{25}F_3NO$ 436.18828 | 436.18844 |
| JN074 | $^1$H NMR δ 12.79 (m, 1H), 7.68-7.64 (m, 2H), 7.49 (s, 1H), 7.47-7.44 (m, 3H), 7.35 (d, J = 8.5 Hz, 2H), 7.18 (d, J = 8.6 Hz, 2H), 7.11 (d, J = 8.4 Hz, 2H), 7.09 (s, 1H), 7.06 (d, J = 8.6 Hz, 2H), 6.56 (s, 1H), 4.28 (dd, J = 13.2, 4.4 Hz, 1H), 4.21 (dd, J = 13.0, 4.7 Hz, 1H), 4.01 (dd, J = 13.1, 3.6 Hz, 1H), 3.92 (dd, J = 13.0, 6.6 Hz, 1H), 2.66 (d, J = 4.0 Hz, 3H); $^{13}$C NMR δ 196.44, 140.93, 138.20, 138.11, 136.65, 135.95, 134.76, 133.91, 132.27, 131.97, 131.49, 130.86, 130.44, 129.60, 129.58, 128.96, 128.42, 60.46, 54.02, 39.82. | $C_{26}H_{24}Cl_2NO$ 436.12295 | 436.11996 |
| JN075 | $^1$H NMR δ 12.80 (m, 1H), 7.68-7.63 (m, 2H), 7.51 (s, 1H), 7.48-7.44 (m, 3H), 7.37-7.29 (m, 3H), 7.21-7.16 (m, 3H), 7.10 (s, 1H), 7.08-7.03 (m, 3H), 6.57 (s, 1H), 4.28 (dd, J = 13.3, 4.3 Hz, 1H), 4.21 (dd, J = 13.1, 4.8 Hz, 1H), 4.01 (dd, J = 13.1, 3.7 Hz, 1H), 3.93 (dd, J = 13.0, 6.4 Hz, 1H), 2.67 (d, J = 3.9 Hz, 3H); $^{13}$C NMR δ 196.21, 141.18, 138.21, 137.83, 137.31, 136.60, 136.09, 135.14, 132.10, 132.04, 131.49, 130.57, 130.44, 129.61, 129.38, 128.97, 128.85, 128.42, 127.69, 60.48, 54.01, 39.81. | $C_{26}H_{24}Cl_2NO$ 436.12295 | 436.12001 |
| JN076 | $^1$H NMR δ 12.71 (m, 1H), 7.69 (s, 1H), 7.68-7.63 (m, 2H), 7.48-7.42 (m, 4H), 7.35 (td, J = 7.7, 1.7 Hz, 1H), 7.26 (td, J = 7.5, 1.3 Hz, 1H), 7.17 (d, J = 8.6 Hz, 2H), 7.10 (dd, J = 7.6, 1.7 Hz, 2H), 7.03 (d, J = 8.6 Hz, 2H), 6.63 (s, 1H), 4.29 (br s, 1H), 4.22 (br s, 1H), 3.99 (br s, 2H), 2.67 (s, 3H); $^{13}$C NMR δ 195.77, 143.10, 137.85, 137.24, 136.25, 136.15, 135.25, 133.57, 132.28, 131.86, 131.80, 131.50, 130.29, 130.25, 130.10, 129.50, 128.93, 128.56, 127.70, 60.31, 54.34, 39.67. | $C_{26}H_{24}Cl_2NO$ 436.12295 | 436.12032 |
| JN077 | $^1$H NMR δ 12.22 (m, 1H), 7.40-7.34 (m, 3H), 7.31 (s, 1H), 7.28 (s, 1H), 7.19-7.13 (m, 4H), 7.02 (d, J = 8.6 Hz, 2H), 6.64 (s, 1H), 3.92 (d, J = 5.3 Hz, 2H), 3.46 (br d, J = 12.1 Hz, 2H), 2.76-2.65 (m, 2H), 2.35-2.22 (m, 2H), 1.92-1.79 (m, 3H), 1.46-1.34 (m, 1H); $^{13}$C NMR δ 196.87, 139.49, 139.26, 139.00, 136.14, 135.55, 135.53, 132.61, 131.88, 129.33, 129.23, 128.80, 128.69, 55.11, 53.39, 22.68, 22.16. | $C_{23}H_{25}ClNO$ 366.16192 | 366.16080 |
| JN078 | $^1$H NMR δ 12.55 (m, 1H), 7.42-7.33 (m, 3H), 7.35-7.31 (m, 3H), 7.29-7.26 (m, 2H), 7.15-7.11 (m, 3H), 6.63 (d, J = 0.9 Hz, 1H), 3.93 (d, J = 5.7 Hz, 2H), 3.57-3.49 (m, 2H), 2.78-2.65 (m, 2H), 2.22-2.12 (m, 2H), | $C_{22}H_{23}ClNO$ 352.14627 | 352.14423 |

TABLE 2-continued

Physical Properties of Synthesized Compounds

| Compound No. | NMR[1] | Formula[2] m/z (calc.) | m/z (meas.) |
|---|---|---|---|
| | 2.09-1.99 (m, 2H); $^{13}$C NMR δ 199.58, 140.75, 140.20, 137.94, 137.04, 134.60, 134.37, 130.05, 129.92, 129.31, 129.10, 129.07, 126.22, 53.54, 50.79, 23.40. | | |
| JN079 | $^1$H NMR δ 13.18 (m, 1H), 7.42-7.35 (m, 3H), 7.33 (s, 1H), 7.25 (s, 1H), 7.19-7.14 (m, 4H), 7.03 (d, J = 8.6 Hz, 2H), 6.65 (s, 1H), 4.29 (t, J = 12.1 Hz, 2H), 3.96 (s, 2H), 3.95 (d, J = 12.2 Hz, 2H), 3.36 (d, J = 12.2 Hz, 2H), 3.03-2.92 (m, 2H); $^{13}$C NMR δ 196.71, 139.49, 139.39 (2C), 135.67, 135.55, 135.47, 132.52, 131.91, 129.39, 129.24, 128.84, 128.78, (one low-field carbon is overlapped), 63.68, 55.70, 52.07. | [M − H]$^-$ $C_{22}H_{22}ClN_2O$ 365.14261 | 365.11749 |
| JN080 | $^1$H NMR δ 12.77 (m, 1H), 7.70-7.63 (m, 2H), 7.49-7.43 (m, 4H), 7.18 (d, J = 8.4 Hz, 2H), 7.16 (d, J = 8.2 Hz, 2H), 7.10 (s, 1H), 7.07 (d, J = 8.4 Hz, 2H), 7.03 (d, J = 8.1 Hz, 2H), 6.57 (s, 1H), 4.28 (dd, J = 13.2, 4.6 Hz, 1H), 4.21 (dd, J = 13.3, 4.9 Hz, 1H), 4.06-3.98 (m, 1H), 3.92 (m, 1H), 2.66 (d, J = 4.4 Hz, 3H); $^{13}$C NMR δ 196.68, 140.58, 140.55, 138.43, 138.33, 136.67, 135.82, 132.46, 132.04, 131.95, 131.51, 131.01, 130.45, 129.62, 128.93, 128.43, 119.93, 60.48, 54.05, 39.83. | $C_{26}H_{24}ClN_4O$ 443.16332 | 443.16152 |
| JN081 | $^1$H NMR δ 12.61 (m, 1H), 7.63-7.57 (m, 2H), 7.49-7.44 (m, 3H), 7.36 (s, 1H), 7.33 (d, J = 8.6 Hz, 2H), 7.22 (d, J = 8.4 Hz, 2H), 7.12 (m, 3H), 7.02 (d, J = 8.5 Hz, 2H), 6.69 (s, 1H), 4.15 (dd, J = 13.0, 4.2 Hz, 1H), 4.03 (dd, J = 13.0, 5.5 Hz, 1H), 3.88 (d, J = 5.4 Hz, 2H), 2.47 (d, J = 4.3 Hz, 3H); $^{13}$C NMR δ 199.36, 141.74, 140.97, 139.61, 137.02, 134.80, 134.07, 133.59, 131.45, 130.47, 129.87, 129.85, 129.63, 129.16, 128.28, 127.73, 119.89, 60.21, 51.49, 39.19, 29.84. | $C_{26}H_{24}ClN_4O$ 443.16332 | 443.16275 |
| JN082 | $^1$H NMR δ 12.76 (m, 1H), 7.70-7.62 (m, 2H), 7.47-7.43 (m, 3H), 7.40-7.37 (m, 3H), 7.35 (s, 1H), 7.22 (t, J = 8.0 Hz, 1H), 7.16 (dd, J = 6.6, 2.9 Hz, 2H), 7.11 (s, 1H), 6.90 (dd, J = 8.4, 1.9 Hz, 1H), 6.81 (dd, J = 10.4, 1.9 Hz, 1H), 6.59 (s, 1H), 4.23 (m, 2H), 3.96 (m, 2H), 2.64 (s, 3H); $^{13}$C NMR δ 196.52, 157.75 (d, J = 249.3 Hz), 140.54, 138.80, 138.09, 136.59, 135.03, 134.69 (d, J = 7.1 Hz), 131.47, 130.65, 130.41, 129.59, 129.47, 129.11, 128.99, 128.45, 127.40 (d, J = 3.5 Hz), 122.26 (d, J = 17.8 Hz), 117.96 (d, J = 22.4 Hz), 60.44, 53.80, 39.76. | $C_{26}H_{24}ClFNO$ 420.15250 | 420.15142 |
| JN083 | $^1$H NMR δ 12.73 (m, 1H), 7.69-7.62 (m, 2H), 7.47-7.42 (m, 3H), 7.37-7.32 (m, 3H), 7.28 (d, J = 9.5 Hz, 2H), 7.18-7.13 (m, 2H), 7.07 (dd, J = 9.9, 2.0 Hz, 1H), 6.82 (dd, J = 8.6, 2.0 Hz, 1H), 6.74 (t, J = 8.2 Hz, 1H), 6.65 (s, 1H), 4.29 (dd, J = 13.1, 4.7 Hz, 1H), 4.17 (dd, J = 13.1, 5.5 Hz, 1H), 4.01 (dd, J = 13.2, 4.5 Hz, 1H), 3.93 (dd, J = 13.1, 6.7 Hz, 1H), 2.64 (d, J = 4.7 Hz, 3H); $^{13}$C NMR δ 196.47, 160.90 (d, J = 254.7 Hz), 141.22, 139.55, 136.47, 136.18 (d, J = 10.6 Hz), 135.13, 131.50, 131.24 (d, J = 3.1 Hz), 130.37, 130.10 (d, J = 4.6 Hz), 129.56, 129.31, 129.09, 128.91, 128.48, 124.48 (d, J = 3.5 Hz), 121.05 (d, J = 12.5 Hz), 116.67 (d, J = 25.4 Hz), 60.20, 53.31, 39.33. | $C_{26}H_{24}ClFNO$ 420.15250 | 420.15095 |
| JN084 | Purity >80%, with the impurity being the Z isomer. $^1$H NMR δ 12.82 (m, 1H), 7.69-7.64 (m, 2H), 7.53-7.45 (m, 6H), 7.20-7.13 (m, 4H), 7.10 (s, 1H), 7.06 (d, J = 8.5 Hz, 2H), 6.58 (s, 1H), 4.28 (dd, J = 13.1, 4.8 Hz, 1H), 4.20 (dd, J = 13.1, 5.1 Hz, 1H), 4.00 (dd, J = 13.2, 3.9 Hz, 1H), 3.92 (dd, J = 13.1, 6.9 Hz, 1H), 3.14 (s, 1H), 2.66 (d, J = 4.7 Hz, 3H); $^{13}$C NMR δ 196.43, impurity peak overlap in the aromatic region, 83.18, 78.54, 60.51, 54.02, 39.82. | $C_{28}H_{25}ClNO$ 426.16192 | 426.16082 |

TABLE 2-continued

Physical Properties of Synthesized Compounds

| Compound No. | NMR[1] | Formula[2] m/z (calc.) | m/z (meas.) |
|---|---|---|---|
| JN088 | $^1$H NMR δ 7.81 (s, 1H), 7.43-7.35 (m, 3H), 7.22-7.17 (m, 2H), 7.14 (dd, J = 8.5, 1.4 Hz, 2H), 6.98 (dd, J = 8.5, 1.4 Hz, 2H), 4.33 (dt, J = 5.1, 1.7 Hz, 2H), 4.07 (q, J = 5.3 Hz, 1H), 3.54 (ddd, J = 11.1, 5.2, 1.2 Hz, 1H), 3.49 (ddd, J = 11.1, 5.5, 1.1 Hz, 1H), 2.40 (d, J = 5.9 Hz, 1H); $^{13}$C NMR δ 167.66, 140.05, 135.44, 135.38, 132.90, 132.52, 132.00, 129.60, 129.03, 128.72, 128.37, 69.76, 66.01, 45.98. | $C_{18}H_{17}Cl_2O_3$ 351.05493 | 351.05448 |
| JN089 | $^1$H NMR (DMSO-$d_6$) δ 7.44-7.39 (m, 4H), 7.37 (t, J = 5.6 Hz, 1H), 7.24 (d, J = 8.6 Hz, 2H), 7.21-7.17 (m, 2H), 6.99 (d, J = 8.7 Hz, 2H), 5.35 (d, J = 5.3 Hz, 1H), 3.83-3.74 (m, 1H), 3.58 (dd, J = 11.2, 4.4 Hz, 1H), 3.47 (dd, J = 11.2, 6.0 Hz, 1H), 3.34-3.28 (m, 1H), 3.19 (ddd, J = 13.4, 6.7, 5.6 Hz, 1H); $^{13}$C NMR (DMSO-$d_6$) δ 167.32, 137.21, 135.65, 133.96, 132.78, 132.71, 131.30, 129.40, 129.07, 128.27, 128.23, 69.06, 47.88, 43.19 | $C_{18}H_{18}Cl_2NO_2$ 350.07091 | 350.06477 |
| JN090 | $^1$H NMR δ 12.91-12.74 (m, 1H), 7.70-7.64 (m, 2H), 7.49-7.44 (m, 4H), 7.20-7.12 (m, 4H), 7.11-7.03 (m, 5H), 6.58 (s, 1H), 4.28 (dd, J = 13.1, 4.8 Hz, 1H), 4.21 (dd, J = 13.1, 5.3 Hz, 1H), 4.01 (dd, J = 13.1, 4.2 Hz, 1H), 3.92 (dd, J = 13.0, 6.9 Hz, 1H), 2.66 (d, J = 4.8 Hz, 3H); $^{13}$C NMR δ 196.65, 162.84 (d, J = 248.9 Hz), 140.76, 138.31, 138.22, 136.66, 135.86, 132.41, 131.96, 131.50, 131.35 (d, J = 3.4 Hz), 131.28 (d, J = 8.1 Hz), 130.45, 129.62, 128.92, 128.43, 116.47 (d, J = 21.7 Hz), 60.48, 54.05, 39.82. | $C_{26}H_{24}ClFNO$ 420.15250 | 420.15194 |
| JN091 | $^1$H NMR δ 12.77-12.55 (m, 1H), 7.63-7.57 (m, 2H), 7.49-7.43 (m, 3H), 7.37 (s, 1H), 7.32 (dd, J = 8.5, 5.1 Hz, 2H), 7.23 (d, J = 8.2 Hz, 2H), 7.14-7.04 (m, 5H), 6.70 (s, 1H), 4.14 (dd, J = 13.0, 4.4 Hz, 1H), 4.02 (dd, J = 13.0, 5.7 Hz, 1H), 3.87 (d, J = 5.6 Hz, 2H), 2.47 (d, J = 4.6 Hz, 3H); $^{13}$C NMR δ 199.32, 163.17 (d, J = 250.0 Hz), 141.73, 139.56, 136.98, 134.81, 134.05, 133.12 (d, J = 3.4 Hz), 131.45, 130.46, 130.19, 129.85, 129.63, 129.16, 128.28, 128.15 (d, J = 8.4 Hz), 116.40 (d, J = 21.8 Hz), 60.20, 51.47, 39.17. | $C_{26}H_{24}ClFNO$ 420.15250 | 420.15197 |
| JN092 | $^1$H NMR δ 12.90-12.72 (m, 1H), 7.69-7.64 (m, 2H), 7.50 (s, 1H), 7.47-7.43 (m, 3H), 7.35 (td, J = 8.0, 5.9 Hz, 1H), 7.17 (d, J = 8.5 Hz, 2H), 7.11 (s, 1H), 7.05 (d, J = 8.4 Hz, 3H), 6.94 (d, J = 7.6 Hz, 1H), 6.90 (dt, J = 9.3, 2.0 Hz, 1H), 6.58 (s, 1H), 4.28 (dd, J = 13.1, 5.0 Hz, 1H), 4.21 (dd, J = 13.1, 5.3 Hz, 1H), 4.01 (dd, J = 13.1, 4.2 Hz, 1H), 3.93 (dd, J = 13.1, 6.9 Hz, 1H), 2.66 (d, J = 4.8 Hz, 3H); $^{13}$C NMR δ 196.22, 163.20 (d, J = 248.0 Hz), 140.96, 138.27, 138.01 (d, J = 1.9 Hz), 137.59 (d, J = 7.8 Hz), 136.59, 136.03, 132.16, 131.99, 131.50, 130.95 (d, J = 8.5 Hz), 130.45, 129.62, 128.95, 128.42, 125.18 (d, J = 3.1 Hz), 116.51 (d, J = 21.9 Hz), 115.72 (d, J = 20.9 Hz), 60.47, 53.98, 39.79. | $C_{26}H_{24}ClFNO$ 420.15250 | 420.15203 |
| JN093 | $^1$H NMR δ 12.74-12.62 (m, 1H), 7.63-7.56 (m, 2H), 7.48-7.43 (m, 3H), 7.40 (s, 1H), 7.38-7.31 (m, 1H), 7.23 (d, J = 8.2 Hz, 2H), 7.16-7.09 (m, 4H), 7.08-7.02 (m, 2H), 6.70 (s, 1H), 4.15 (dd, J = 13.0, 4.6 Hz, 1H), 4.02 (dd, J = 13.0, 5.8 Hz, 1H), 3.89 (d, J = 5.9 Hz, 2H), 2.47 (d, J = 4.8 Hz, 3H); $^{13}$C NMR δ 198.91, 163.17 (d, J = 247.6 Hz), 141.86, 139.40 (d, J = 2.3 Hz), 138.95 (d, J = 7.6 Hz), 136.95, 135.03, 133.76, 131.44, 131.14, 130.97 (d, J = 8.3 Hz), 130.46, 129.90, 129.63, 129.21, 128.26, 121.96 (d, J = 2.9 Hz), 116.05 (d, J = 21.3 Hz), 113.26 (d, J = 22.8 Hz), 60.19, 51.38, 39.10. | $C_{26}H_{24}ClFNO$ 420.15250 | 420.15212 |

TABLE 2-continued

Physical Properties of Synthesized Compounds

| Compound No. | NMR[1] | Formula[2] m/z (calc.) | m/z (meas.) |
|---|---|---|---|
| JN094 | $^1$H NMR δ 12.80-12.68 (m, 1H), 7.68-7.65 (m, 2H), 7.64 (s, 1H), 7.48-7.43 (m, 3H), 7.41-7.34 (m, 1H), 7.19 (d, J = 8.3 Hz, 2H), 7.15-7.08 (m, 5H), 7.06 (s, 1H), 6.54 (s, 1H), 4.30 (dd, J = 13.1, 4.8 Hz, 1H), 4.19 (dd, J = 13.1, 5.5 Hz, 1H), 4.01 (dd, J = 13.1, 4.4 Hz, 1H), 3.95 (dd, J = 13.1, 6.8 Hz, 1H), 2.66 (d, J = 4.8 Hz, 3H); $^{13}$C NMR δ 195.94, 159.87 (d, J = 246.5 Hz), 142.77, 137.91, 136.27, 136.09, 133.55, 132.41, 131.70, 131.60 (d, J = 3.1 Hz), 131.50, 131.00 (d, J = 8.1 Hz), 130.38, 129.58, 128.97, 128.53, 125.00 (d, J = 3.5 Hz), 123.73 (d, J = 15.9 Hz), 116.35 (d, J = 21.5 Hz), 60.30, 54.19, 39.62. | $C_{26}H_{24}ClFNO$ 420.15250 | 420.15138 |
| JN095 | $^1$H NMR δ 12.59-12.47 (m, 1H), 7.64-7.59 (m, 2H), 7.47-7.42 (m, 4H), 7.35 (tdd, J = 7.7, 5.3, 1.6 Hz, 1H), 7.28 (s, 1H), 7.26-7.22 (m, 3H), 7.20 (t, J = 7.6 Hz, 1H), 7.10-7.01 (m, 3H), 6.71 (s, 1H), 4.26 (dd, J = 13.1, 4.4 Hz, 1H), 4.00 (dd, J = 13.1, 6.2 Hz, 1H), 3.85 (d, J = 5.8 Hz, 2H), 2.52 (d, J = 4.9 Hz, 3H); $^{13}$C NMR δ 198.49, 159.60 (d, J = 248.0 Hz), 140.45, 136.36 (d, J = 1.4 Hz), 135.20 (d, J = 2.9 Hz), 134.66, 134.08, 131.45, 131.04 (d, J = 8.6 Hz), 130.33 (2C), 130.02, 129.87 (d, J = 3.2 Hz), 129.55, 129.16, 128.58, 126.14 (d, J = 13.3 Hz), 125.15 (d, J = 3.2 Hz), 116.30 (d, J = 22.1 Hz), 59.86, 51.98, 38.93. | $C_{26}H_{24}ClFNO$ 420.15250 | 420.15132 |
| JN096 | $^1$H NMR δ 7.58 (s, 1H), 7.45-7.38 (m, 2H), 7.36-7.27 (m, 5H), 7.27-7.22 (m, 1H), 7.16 (d, J = 7.3 Hz, 2H), 7.12 (d, J = 8.2 Hz, 2H), 6.95 (d, J = 8.2 Hz, 2H), 3.65 (s, 2H), 2.29 (s, 3H), 2.25 (s, 4H); $^{13}$C NMR δ 199.24, 141.40, 137.37 (2C), 136.74, 135.25, 133.22, 132.10, 129.52, 129.33, 129.05, 128.68, 128.31, 128.26, 126.94, 59.53, 40.56, 28.15. | $C_{25}H_{25}ClNO$ 390.16192 | 390.25269 |
| JN097 | $^1$H NMR δ 7.61 (s, 1H), 7.46-7.38 (m, 3H), 7.19-7.15 (m, 2H), 7.13 (d, J = 8.6 Hz, 2H), 6.95 (d, J = 8.5 Hz, 2H), 3.34 (tdd, J = 5.6, 4.0, 2.7 Hz, 1H), 2.90-2.82 (m, 2H), 2.68 (dd, J = 17.5, 5.3 Hz, 1H), 2.45 (dd, J = 4.8, 2.7 Hz, 1H); $^{13}$C NMR δ 198.46, 140.56, 137.64, 136.21, 135.53, 132.98, 132.25, 129.58, 129.53, 128.74, 128.51, 48.45, 47.02, 43.63. | $C_{18}H_{16}ClO_2$ 299.08333 | 299.08304 |
| JN098 | $^1$H NMR (400 MHz) δ 7.38-7.29 (m, 5H), 7.15 (d, J = 8.6 Hz, 2H), 7.02 (d, J = 8.8 Hz, 2H), 6.43 (s, 1H), 3.33 (tdd, J = 5.7, 3.9, 2.6 Hz, 1H), 2.87 (dd, J = 4.9, 3.9 Hz, 1H), 2.72 (d, J = 5.7 Hz, 2H), 2.60 (dd, J = 4.9, 2.6 Hz, 1H); $^{13}$C NMR δ 168.91, 148.01, 134.14, 133.23, 132.70, 130.35, 129.41, 128.92, 128.76, 128.63, 119.29, 47.93, 46.81, 38.23. | $C_{18}H_{16}ClO_3$ 315.07825 | 315.07759 |
| JN099 | $^1$H NMR δ 7.63 (s, 1H), 7.48-7.39 (m, 3H), 7.20-7.12 (m, 4H), 6.96 (d, J = 8.2 Hz, 2H), 4.38-4.29 (m, 1H), 3.59 (dd, J = 11.0, 5.3 Hz, 2H), 3.30 (d, J = 4.4 Hz, 1H), 2.93-2.80 (m, 1H); $^{13}$C NMR δ 200.55, 140.62, 138.25, 135.91, 135.77, 132.80, 132.33, 129.57 (2C), 128.80, 128.62, 68.17, 48.30, 43.45. | $C_{18}H_{17}Cl_2O_2$ 335.06001 | 335.06131 |
| JN100 | $^1$H NMR δ 12.88-12.74 (m, 1H), 7.70 (s, 1H), 7.69-7.64 (m, 2H), 7.49-7.43 (m, 3H), 7.21 (d, J = 8.3 Hz, 2H), 7.15-7.08 (m, 1H), 7.11 (d, J = 8.7 Hz, 2H), 7.05 (s, 1H), 6.92-6.84 (m, 2H), 6.54 (s, 1H), 4.29 (dd, J = 13.3, 4.4 Hz, 1H), 4.21 (dd, J = 13.2, 4.8 Hz, 1H), 4.02 (dd, J = 13.1, 3.6 Hz, 1H), 3.93 (dd, J = 13.1, 6.4 Hz, 1H), 2.67 (d, J = 3.9 Hz, 3H); $^{13}$C NMR δ 195.86, 163.42 (dd, J = 251.67, 11.87 Hz), 160.11 (dd, J = 249.06, 11.99 Hz), 143.60, 137.91, 136.30, 132.58, 132.56 (dd, J = 9.52, 4.71 Hz), 132.21, 131.66, 131.49, 130.42, 129.60, 129.08, 128.47, one carbon overlapped, 119.71 (dd, J = 16.24, 4.11 Hz), 112.42 (dd, J = 21.38, 3.53 Hz), 104.92 (t, J = 25.50 Hz), 60.44, 54.25, 39.79. | $C_{26}H_{23}ClF_2NO$ 438.14307 | 438.14182 |

TABLE 2-continued

Physical Properties of Synthesized Compounds

| Compound No. | NMR[1] | Formula[2] m/z (calc.) | m/z (meas.) |
|---|---|---|---|
| JN101 | $^1$H NMR δ 12.61-12.46 (m, 1H), 7.64-7.58 (m, 2H), 7.49-7.39 (m, 4H), 7.29 (s, 1H), 7.24 (d, J = 8.3 Hz, 2H), 7.20 (s, 1H), 7.07 (d, J = 8.1 Hz, 2H), 6.95 (ddd, J = 9.0, 6.5, 2.7 Hz, 1H), 6.81 (td, J = 9.8, 2.5 Hz, 1H), 6.69 (s, 1H), 4.30-4.20 (m, 1H), 4.05-3.96 (m, 1H), 3.87-3.80 (m, 2H), 2.51 (br s, 3H); $^{13}$C NMR δ 198.37, 163.43 (dd, J = 252.71, 12.77 Hz), 159.77 (dd, J = 250.76, 12.10 Hz), 140.50, 136.35, 135.34, 134.73, 134.22, 133.95, 131.44, 130.95 (m), 130.36, 130.01, 129.56, 129.21, 128.51, 122.49 (m), 112.49 (d, J = 24.32 Hz), 104.77 (t, J = 25.93 Hz), 59.94, 51.97, 38.98. | $C_{26}H_{23}ClF_2NO$ 438.14307 | 438.14167 |
| JN102 | $^1$H NMR δ 8.22 (br s, 1H), 7.91 (s, 1H), 7.58-7.48 (m, 3H), 7.34-7.29 (m, 2H), 7.14 (d, J = 8.7 Hz, 2H), 6.96 (d, J = 8.7 Hz, 2H), 5.34 (q, J = 1.6 Hz, 1H), 5.26 (s, 1H), 1.79 (s, 3H); $^{13}$C NMR δ 165.51, 163.94, 140.09, 139.45, 135.63, 134.97, 134.10, 132.74, 132.02, 130.47, 129.73, 129.65, 128.79, 121.80, 18.13. | $C_{19}H_{17}ClNO_2$ 326.09423 | 326.09264 |
| JN103 | $^1$H NMR (400 MHz) δ 8.16 (br s, 1H), 7.87 (s, 1H), 7.35-7.20 (m, 4H), 7.16 (d, J = 8.6 Hz, 2H), 6.95 (d, J = 8.5 Hz, 2H), 5.41-5.37 (m, 1H), 5.32 (s, 1H), 1.83 (s, 3H); $^{13}$C NMR (DMSO-d$_6$) δ 168.86, 167.99, 161.87 (d, J = 245.4 Hz), 139.20, 136.05, 134.77, 133.44, 133.35, 131.75, 131.65 (d, J = 8.4 Hz), 131.50, 131.44 (d, J = 3.4 Hz), 128.45, 123.05, 115.79 (d, J = 21.5 Hz), 18.09. | $C_{19}H_{16}ClFNO_2$ 344.08481 | 344.08296 |
| JN104 | $^1$H NMR δ 7.60 (s, 1H), 7.18-7.09 (m, 6H), 6.95 (d, J = 8.5 Hz, 2H), 5.96 (ddt, J = 17.1, 10.2, 6.7 Hz, 1H), 5.17 (dq, J = 10.2, 1.4 Hz, 1H), 5.08 (dq, J = 17.2, 1.5 Hz, 1H), 3.36 (dt, J = 6.7, 1.4 Hz, 2H); $^{13}$C NMR δ 198.90, 162.75 (d, J = 248.3 Hz), 139.82, 138.02, 135.50, 133.00, 132.16 (d, J = 3.4 Hz), 132.07, 131.57 (d, J = 7.9 Hz), 131.16, 128.81, 118.73, 116.48 (d, J = 21.5 Hz), 44.67. | $C_{18}H_{15}ClFO$ 301.07900 | 301.07641 |
| JN105 | $^1$H NMR δ 7.38-7.31 (m, 2H), 7.16 (dd, J = 8.5, 1.2 Hz, 2H), 7.05-6.95 (m, 4H), 6.43 (s, 1H), 3.37-3.28 (m, 1H), 2.87 (t, J = 4.4 Hz, 1H), 2.74 (ddd, J = 16.5, 5.0, 1.0 Hz, 1H), 2.69 (ddd, J = 16.5, 6.4, 1.1 Hz, 1H), 2.60 (ddd, J = 4.8, 2.5, 1.0 Hz, 1H); $^{13}$C NMR δ 168.91, 163.10 (d, J = 250.1 Hz), 147.02, 133.39, 132.50, 130.97 (d, J = 8.4 Hz), 130.30, 130.23 (d, J = 3.4 Hz), 128.74, 119.45, 115.94 (d, J = 21.8 Hz), 47.89, 46.79, 38.20. | $C_{18}H_{15}ClFO_3$ 333.06883 | 333.06602 |
| JN106 | 78% purity. $^1$H NMR δ 7.61 (s, 1H), 7.19-7.08 (m, 6H), 6.96 (d, J = 8.5 Hz, 2H), 3.38-3.32 (m, 1H), 2.91 (dd, J = 17.3, 5.9 Hz, 1H), 2.86 (dd, J = 4.8, 4.0 Hz, 1H), 2.75 (dd, J = 17.3, 5.1 Hz, 1H), 2.49 (dd, J = 4.9, 2.6 Hz, 1H); $^{13}$C NMR δ 198.22, 162.80 (d, J = 248.4 Hz), 139.75, 138.56, 135.74, 132.80, 132.15, 131.81 (d, J = 3.8 Hz), 131.53 (d, J = 8.1 Hz), 128.86, 116.60 (d, J = 21.5 Hz), 48.47, 47.01, 43.27. | $C_{18}H_{15}ClFO_2$ 317.07391 | 317.07150 |
| JN107 | $^1$H NMR δ 7.61 (s, 1H), 7.18-7.04 (m, 7H), 6.98 (d, J = 8.6 Hz, 2H), 6.71 (dt, J = 15.4, 2.2 Hz, 1H), 4.38 (t, J = 2.8 Hz, 2H); $^{13}$C NMR δ 190.51, 162.75 (d, J = 248.2 Hz), 146.68, 140.66, 138.31, 135.40, 133.23, 132.07 (d, J = 3.7 Hz), 132.00, 131.61 (d, J = 8.1 Hz), 128.79, 124.34, 116.46 (d, J = 21.5 Hz), 62.46. | $C_{18}H_{15}ClFO_2$ 317.07391 | 317.07201 |
| JN108 | $^1$H NMR δ 7.38-7.33 (m, 3H), 7.32-7.29 (m, 4H), 7.25-7.19 (m, 4H), 7.15 (d, J = 8.6 Hz, 2H), 7.01 (d, J = 8.6 Hz, 2H), 5.80 (d, J = 0.7 Hz, 1H), 5.72 (q, J = 1.0 Hz, 1H), 3.66 (s, 2H), 3.37 (d, J = 1.0 Hz, 2H); $^{13}$C NMR δ 197.43, 144.46, 141.32, 138.04, 137.75, 136.06, 134.92, 133.36, 131.68, 129.57, 129.16, 129.06, 128.69, 128.67, 128.31, 127.25, 125.52, 36.29, 32.71. | $C_{25}H_{22}ClOS$ 405.10744 | 405.10542 |

TABLE 2-continued

Physical Properties of Synthesized Compounds

| Compound No. | NMR[1] | Formula[2] m/z (calc.) | m/z (meas.) |
|---|---|---|---|
| JN109 | $^1$H NMR δ 7.44-7.31 (m, 7H), 7.29-7.23 (m, 2H), 7.06 (s, 1H), 6.15 (s, 1H), 5.96 (d, J = 1.1 Hz, 1H), 3.71 (q, J = 5.8 Hz, 2H), 3.48 (d, J = 0.9 Hz, 2H), 2.78-2.74 (m, 1H), 2.52 (t, J = 5.8 Hz, 2H); $^{13}$C NMR δ 199.43, 143.76, 141.05, 137.87, 134.19, 134.14, 131.55, 130.22, 129.05, 129.00, 128.94, 128.64, 126.34, 60.50, 35.14, 30.33. | $C_{20}H_{20}ClO_2S$ 359.08670 | 359.08415 |
| JN110 | $^1$H NMR δ 7.58 (s, 1H), 7.45-7.35 (m, 3H), 7.16 (dd, J = 7.8, 1.7 Hz, 2H), 7.13 (d, J = 8.6 Hz, 2H), 6.95 (d, J = 8.5 Hz, 2H), 2.29 (s, 3H); $^{13}$C NMR δ 199.25, 141.40, 137.37, 136.74, 135.26, 133.22, 132.11, 129.52, 129.33, 128.68, 128.27, 28.15. | $C_{16}H_{14}ClO$ 257.07277 | 257.07216 |
| JN111 | $^1$H NMR δ 7.59 (s, 1H), 7.16 (d, J = 8.6 Hz, 2H), 7.13-7.09 (m, 4H), 6.96 (d, J = 8.5 Hz, 2H), 2.34 (s, 3H); $^{13}$C NMR δ 198.95, 162.68 (d, J = 247.9 Hz), 140.54, 138.28, 135.45, 133.04, 132.26 (d, J = 3.5 Hz), 132.00, 131.45 (d, J = 8.0 Hz), 128.80, 116.38 (d, J = 21.5 Hz), 27.79. | $C_{16}H_{13}ClFO$ 275.06335 | 275.06146 |
| JN112 | $^1$H NMR δ 7.37-7.30 (m, 3H), 7.20 (dd, J = 7.9, 1.7 Hz, 2H), 7.08 (d, J = 8.5 Hz, 2H), 6.91 (d, J = 8.6 Hz, 2H), 6.64 (d, J = 1.5 Hz, 1H), 4.46 (d, J = 1.5 Hz, 2H); $^{13}$C NMR δ 142.37, 138.24, 135.06, 132.59, 130.55, 129.08, 128.77, 128.29, 127.93, 125.21, 68.43. | $C_{15}H_{14}ClO$ 245.07277 | N/A[3] |
| JN113 | $^1$H NMR δ 7.35-7.28 (m, 3H), 7.22-7.17 (m, 2H), 7.07 (d, J = 8.6 Hz, 2H), 6.91 (d, J = 8.5 Hz, 2H), 6.65 (d, J = 1.3 Hz, 1H), 4.38 (dd, J = 13.4, 1.5 Hz, 1H), 4.33 (dd, J = 13.4, 1.5 Hz, 1H), 3.83 (dd, J = 11.6, 3.0 Hz, 1H), 3.50 (dd, J = 11.5, 5.8 Hz, 1H), 3.18 (ddt, J = 5.7, 4.1, 2.8 Hz, 1H), 2.80 (dd, J = 5.0, 4.1 Hz, 1H), 2.61 (dd, J = 5.0, 2.7 Hz, 1H); $^{13}$C NMR δ 139.40, 138.54, 135.08, 132.60, 130.63, 128.90, 128.74, 128.25, 127.77, 126.65, 76.37, 71.06, 50.98, 44.42. | $C_{18}H_{18}ClO_2$ 301.09898 | 301.07830 |
| JN114 | $^1$H NMR δ 7.70 (s, 1H), 7.21-7.12 (m, 6H), 6.98 (d, J = 8.5 Hz, 2H), 6.81 (t, J = 4.5 Hz, 1H), 5.80 (t, J = 1.0 Hz, 1H), 5.40-5.37 (m, 1H), 4.39 (d, J = 4.3 Hz, 2H), 1.99 (dd, J = 1.6, 1.0 Hz, 3H); $^{13}$C NMR δ 195.32, 168.23, 163.01 (d, J = 248.9 Hz), 139.42, 137.46, 136.24, 134.92, 132.36, 132.34, 131.50 (d, J = 8.1 Hz), 130.77 (d, J = 3.8 Hz), 128.98, 120.61, 116.84 (d, J = 21.5 Hz), 47.73, 18.65. | $C_{20}H_{18}ClFNO_2$ 358.10046 | 358.09728 |
| JN115 | $^1$H NMR δ 7.36-7.28 (m, 3H), 7.19 (dd, J = 7.9, 1.7 Hz, 2H), 7.08 (d, J = 8.6 Hz, 2H), 6.92 (d, J = 8.6 Hz, 2H), 6.61 (s, 1H), 4.41-4.29 (m, 2H), 3.96 (h, J = 5.3 Hz, 1H), 3.67-3.60 (m, 2H), 3.57 (dd, J = 11.1, 5.5 Hz, 1H), 3.53 (dd, J = 11.1, 5.7 Hz, 1H), 2.39 (d, J = 5.8 Hz, 1H); $^{13}$C NMR δ 139.24, 138.30, 134.84, 132.80, 130.64, 128.97, 128.69, 128.32, 127.89, 127.15, 76.74, 70.77, 70.37, 46.07. | [M − H]$^-$ $C_{18}H_{17}Cl_2O_2$ 335.06111 | 335.04236 |
| JN116 | $^1$H NMR (DMSO-d$_6$) δ 7.64 (s, 1H), 7.47-7.38 (m, 3H), 7.28 (d, J = 8.6 Hz, 2H), 7.14 (dd, J = 7.8, 1.7 Hz, 2H), 7.09 (d, J = 8.7 Hz, 2H), 6.97 (dt, J = 15.3, 3.7 Hz, 1H), 6.75 (dt, J = 15.3, 2.1 Hz, 1H), 5.07 (t, J = 5.2 Hz, 1H), 4.17 (ddd, J = 5.6, 3.7, 2.1 Hz, 2H). $^{13}$C NMR (DMSO-d$_6$) δ 190.00, 149.01, 141.70, 136.76, 136.16, 133.71, 133.57, 131.97, 129.33, 129.03, 128.38, 128.07, 123.43, 60.59. | $C_{18}H_{16}ClO_2$ 299.08333 | 299.08181 |
| JN117 | $^1$H NMR δ 8.33 (br s, 1H), 7.48 (dd, J = 8.9, 5.2 Hz, 2H), 7.35-7.29 (m, 4H), 7.08 (t, J = 8.7 Hz, 2H), 6.88 (s, 1H), 5.48 (q, J = 1.6 Hz, 1H), 5.46 (q, J = 1.0 Hz, 1H), 1.83 (dd, J = 1.6, 0.9 Hz, 3H). $^{13}$C NMR δ 170.12, 165.12, 163.07 (d, J = 248.6 Hz), 139.29, 137.28, 134.50, 133.91, 132.42 (d, J = 3.4 Hz), 129.69, 129.07, 128.62, 128.61 (d, J = 8.1 Hz), 123.07, 115.96 (d, J = 21.7 Hz), 18.22. | $C_{19}H_{16}ClFNO_2$ 344.08481 | 344.08448 |

TABLE 2-continued

Physical Properties of Synthesized Compounds

| Compound No. | NMR[1] | Formula[2] m/z (calc.) | m/z (meas.) |
|---|---|---|---|
| JN118 | $^1$H NMR δ 8.11 (br s, 1H), 7.93 (s, 1H), 7.29-7.20 (m, 1H), 7.20 (d, J = 8.6 Hz, 2H), 7.06-6.97 (m, 2H), 6.99 (d, J = 8.5 Hz, 2H), 5.46-5.42 (m, 2H), 1.88 (dd, J = 1.6, 0.9 Hz, 3H). $^{13}$C NMR δ 166.16, 163.84, 163.78 (dd, J = 253.7, 11.3 Hz), 160.24 (dd, J = 251.8, 11.9 Hz), 141.88, 140.07, 135.97, 132.83 (dd, J = 9.5, 4.0 Hz), 132.34, 131.25, 128.93, 127.25, 121.84, 118.21 (dd, J = 16.5, 4.2 Hz), 113.25 (dd, J = 21.5, 3.8 Hz), 105.58 (t, J = 25.3 Hz), 18.15. | $C_{19}H_{15}ClF_2NO_2$ 362.07539 | 362.07385 |
| JN119 | $^1$H NMR δ 8.25 (br s, 1H), 7.89 (s, 1H), 7.58-7.50 (m, 3H), 7.31 (dd, J = 7.7, 1.7 Hz, 2H), 7.20 (ddd, J = 8.1, 2.1, 1.0 Hz, 1H), 7.10 (t, J = 7.9 Hz, 1H), 6.99 (t, J = 1.9 Hz, 1H), 6.93 (d, J = 7.8 Hz, 1H), 5.35 (q, J = 1.6 Hz, 1H), 5.27 (q, J = 1.0 Hz, 1H), 1.80 (dd, J = 1.6, 0.9 Hz, 3H). $^{13}$C NMR δ 165.52, 163.84, 140.10, 139.24, 136.08, 135.00, 134.75, 134.41, 130.58, 130.47, 129.75, 129.70, 129.68, 129.56, 128.93, 121.86, 18.16. | $C_{19}H_{17}ClNO_2$ 326.09423 | 326.09292 |
| JN120 | $^1$H NMR δ 8.66-8.56 (br s, 1H), 7.51 (dd, J = 8.3, 1.5 Hz, 2H), 7.42-7.34 (m, 4H), 7.31-7.27 (m, 1H), 7.26-7.24 (m, 2H), 6.92 (s, 1H), 5.50 (q, J = 1.0 Hz, 1H), 5.46 (q, J = 1.5 Hz, 1H), 1.82 (dd, J = 1.6, 0.9 Hz, 3H). $^{13}$C NMR δ 170.37, 165.35, 139.24, 139.08, 137.45, 136.11, 134.66, 130.05, 128.94, 128.83, 128.42, 128.40, 128.17, 126.72, 126.50, 123.11, 18.22. | $C_{19}H_{17}ClNO_2$ 326.09423 | 326.09283 |
| JN121 | $^1$H NMR δ 8.26 (br s, 1H), 7.96 (s, 1H), 7.58-7.51 (m, 3H), 7.42 (d, J = 8.3 Hz, 2H), 7.31 (dd, J = 7.6, 1.9 Hz, 2H), 7.15 (d, J = 8.2 Hz, 2H), 5.36 (q, J = 1.6 Hz, 1H), 5.27 (s, 1H), 1.81-1.79 (m, 3H). $^{13}$C NMR δ 165.47, 163.79, 140.06, 138.94, 137.75, 135.96, 134.62, 131.04 (q, J = 32.3 Hz), 130.86, 130.51, 129.83, 129.67, 125.39 (q, J = 3.8 Hz), 123.85 (q, J = 272.3 Hz), 121.95, 18.15. | $C_{20}H_{17}F_3NO_2$ 360.12059 | 360.11921 |
| JN122 | $^1$H NMR δ 8.50 (br s, 1H), 7.59 (d, J = 8.0 Hz, 2H), 7.55-7.50 (m, 4H), 7.45-7.34 (m, 3H), 7.01 (s, 1H), 5.47 (d, J = 0.8 Hz, 1H), 5.46 (q, J = 1.6 Hz, 1H), 1.82 (dd, J = 1.6, 0.9 Hz, 3H). $^{13}$C NMR δ 170.25, 165.17, 139.87, 139.24, 139.20, 135.95, 130.17 (q, J = 32.4 Hz), 129.02, 128.99, 128.67, 128.13, 126.76, 125.71 (q, J = 3.8 Hz), 124.09 (q, J = 272.1 Hz), 123.14, 18.18. | $C_{20}H_{17}F_3NO_2$ 360.12059 | 360.11870 |
| JN123 | $^1$H NMR δ 7.30-7.22 (m, 4H), 7.22-7.18 (m, 4H), 7.15 (d, J = 8.3 Hz, 2H), 7.00 (dd, J = 7.9, 1.6 Hz, 2H), 6.96 (d, J = 8.3 Hz, 2H), 6.00 (s, 1H), 5.71 (d, J = 1.4 Hz, 1H), 4.49 (t, J = 7.3 Hz, 1H), 3.45 (d, J = 13.1 Hz, 1H), 3.39 (dd, J = 13.8, 7.5 Hz, 1H), 3.33-3.22 (m, 2H), 2.95 (d, J = 14.4 Hz, 1H), 2.89 (dd, J = 13.8, 7.2 Hz, 1H), 1.99 (s, 3H). $^{13}$C NMR δ 201.05, 145.53, 139.05, 138.81, 138.45, 131.94, 130.63, 129.09, 128.92, 128.40, 128.37, 128.35, 127.28, 127.15, 126.39, 62.27, 58.06, 55.72, 42.18, 39.17. | $C_{26}H_{27}ClNO$ 404.17757 | 404.17636 |
| JN124 | $^1$H NMR δ 12.54-12.45 (m, 1H), 12.45-12.37 (m, 1H), 7.56-7.47 (m, 4H), 7.45-7.38 (m, 6H), 7.32-7.27 (m, 3H), 7.25-7.20 (m, 3H), 7.19-7.09 (m, 9H), 7.04 (s, 1H), 7.02-6.96 (m, 4H), 6.69 (s, 2H), 4.62 (dd, J = 8.4, 6.6 Hz, 2H), 4.00 (ddd, J = 13.6, 9.6, 4.3 Hz, 2H), 3.92-3.71 (m, 6H), 3.38 (dt, J = 13.7, 8.4 Hz, 2H), 2.98 (dd, J = 13.7, 6.5 Hz, 2H), 2.30 (d, J = 4.7 Hz, 3H), 2.25 (d, J = 4.6 Hz, 3H). $^{13}$C NMR δ 199.32, 199.25, 138.35, 137.94, 137.91, 137.56, 137.52, 136.73, 136.51, 132.53, 132.50, 131.35, 130.57, 130.52, 130.32, 130.29, 129.51, 129.48, 128.65, 128.43, 128.37, 128.08, 128.02, | $C_{26}H_{27}ClNO$ 404.17757 | 404.17670 |

TABLE 2-continued

Physical Properties of Synthesized Compounds

| Compound No. | NMR[1] | Formula[2] m/z (calc.) | m/z (meas.) |
|---|---|---|---|
| | 127.94, 59.87, 59.74, 54.77, 54.69, 52.43, 52.25, 39.27, 39.21, 38.88, 38.36. | | |
| JN125 | $^1$H NMR δ 7.62 (dd, J = 8.3, 1.4 Hz, 2H), 7.59 (s, 1H), 7.45-7.31 (m, 6H), 7.19 (dd, J = 7.9, 1.7 Hz, 2H), 7.13 (d, J = 8.6 Hz, 2H), 6.95 (d, J = 8.6 Hz, 2H), 3.64 (dd, J = 13.0, 4.6 Hz, 2H), 3.57 (dd, J = 13.4, 9.6 Hz, 2H), 3.26 (tt, J = 9.5, 4.8 Hz, 1H). $^{13}$C NMR δ 201.65, 154.51, 140.81, 137.90, 136.13, 136.09, 135.50, 133.07, 132.23, 130.28, 129.58, 129.54, 128.73, 128.60, 128.58, 126.31, 45.02, 39.19. | $C_{25}H_{22}ClN_2O$ 401.14152 | 401.13986 |
| JN126 | $^1$H NMR δ 8.59 (br s, 1H), 8.01 (s, 1H), 7.57 (dd, J = 5.2, 1.2 Hz, 1H), 7.23-7.21 (m, 1H), 7.20 (d, J = 8.5 Hz, 2H), 7.10 (dd, J = 3.5, 1.2 Hz, 1H), 7.06 (d, J = 8.6 Hz, 2H), 5.41 (q, J = 1.6 Hz, 1H), 5.39 (d, J = 1.0 Hz, 1H), 1.85 (t, J = 1.2 Hz, 3H). $^{13}$C NMR δ 165.49, 163.28, 142.92, 140.10, 136.26, 135.03, 132.41, 132.09, 129.43 (2C), 128.94, 128.86, 126.37, 122.04, 18.17. | $C_{17}H_{15}ClNO_2S$ 332.05065 | 332.04811 |
| JN127 | $^1$H NMR δ 8.35 (br s, 1H), 7.36-7.29 (m, 4H), 7.28 (dd, J = 5.1, 1.1 Hz, 1H), 7.11 (dd, J = 3.7, 1.1 Hz, 1H), 7.02 (dd, J = 5.1, 3.7 Hz, 1H), 6.97 (s, 1H), 5.48 (q, J = 1.6 Hz, 1H), 5.44 (q, J = 1.1 Hz, 1H), 1.85 (dd, J = 1.6, 0.9 Hz, 3H). $^{13}$C NMR δ 168.24, 165.25, 139.99, 139.49, 134.57, 133.43, 132.24, 129.72, 129.13, 128.05, 126.75, 126.25, 126.10, 122.89, 18.22. | $C_{17}H_{15}ClNO_2S$ 332.05065 | 332.04786 |
| JN128 | $^1$H NMR δ 8.21 (s, 1H), 8.19 (br s, 1H), 7.63-7.55 (m, 3H), 7.36 (dd, J = 7.7, 1.8 Hz, 2H), 7.27 (dt, J = 5.1, 1.1 Hz, 1H), 7.23 (dd, J = 3.8, 1.1 Hz, 1H), 6.96 (dd, J = 5.1, 3.7 Hz, 1H), 5.33 (q, J = 1.6 Hz, 1H), 5.25 (q, J = 0.9 Hz, 1H), 1.78 (dd, J = 1.7, 0.9 Hz, 3H). $^{13}$C NMR δ 165.57, 163.56, 140.18, 138.57, 134.53, 134.50, 134.34, 131.39, 130.75, 130.37, 130.29, 130.10, 127.12, 121.65, 18.16. | $C_{17}H_{16}NO_2S$ 298.08963 | 298.08741 |
| JN129 | $^1$H NMR δ 8.10 (br s, 1H), 7.83 (s, 1H), 7.33 (dt, J = 9.8, 8.2 Hz, 1H), 7.20 (d, J = 8.6 Hz, 2H), 7.15 (ddd, J = 10.0, 7.4, 2.1 Hz, 1H), 7.07 (ddt, J = 8.0, 3.6, 1.7 Hz, 1H), 6.96 (d, J = 8.6 Hz, 2H), 5.45 (q, J = 1.6 Hz, 1H), 5.39 (q, J = 1.2 Hz, 1H), 1.87 (t, J = 1.2 Hz, 3H). $^{13}$C NMR δ 165.85, 164.06, 151.29 (dd, J = 253.3, 12.8 Hz), 150.99 (dd, J = 253.2, 12.3 Hz), 140.28, 140.16, 136.10, 132.42, 132.21, 131.83, 131.64 (dd, J = 5.8, 4.7 Hz), 129.06, 126.45 (dd, J = 6.2, 3.8 Hz), 122.06, 119.36 (2C, dd, J = 24.9, 17.3 Hz), 18.29. | $C_{19}H_{15}ClF_2NO_2$ 362.07539 | 362.07240 |
| JN130 | $^1$H NMR δ 8.12 (br s, 1H), 7.97 (s, 1H), 7.48 (d, J = 8.2 Hz, 2H), 7.25-7.21 (m, 1H), 7.17 (d, J = 8.3 Hz, 2H), 7.05-6.97 (m, 2H), 5.53-5.38 (m, 2H), 1.89 (dd, J = 1.6, 0.9 Hz, 3H). $^{13}$C NMR δ 166.18, 164.01 (dd, J = 254.1 11.5 Hz), 163.89, 160.37 (dd, J = 251.9, 11.9 Hz), 141.44, 140.13, 137.54, 132.91 (dd, J = 9.6, 4.0 Hz), 131.41 (q, J = 32.7 Hz), 130.18, 129.36, 125.65 (q, J = 3.8 Hz), 123.78 (q, J = 273.4 Hz), 122.15, 118.02 (dd, J = 16.4, 4.1 Hz), 113.41 (dd, J = 21.5, 3.7 Hz), 105.74 (t, J = 25.3 Hz), 18.28. | $C_{20}H_{15}F_5NO_2$ 396.10175 | 396.09825 |
| JN131 | $^1$H NMR δ 8.46 (br s, 1H), 7.59 (d, J = 8.1 Hz, 2H), 7.52-7.44 (m, 3H), 7.07 (s, 1H), 6.96-6.91 (m, 1H), 6.86 (ddd, J = 11.1, 8.7, 2.6 Hz, 1H), 5.42 (q, J = 1.6 Hz, 1H), 5.39 (d, J = 1.0 Hz, 1H), 1.79 (t, J = 1.2 Hz, 3H). $^{13}$C NMR δ 169.33, 165.43, 163.30 (dd, J = 251.7, 12.1 Hz), 160.30 (dd, J = 252.5, 11.9 Hz), 139.18, 138.83, 133.77, 132.36 (d, J = 3.0 Hz), 131.23 (dd, J = 9.7, 4.4 Hz), 130.60 (q, J = 32.8 Hz), 128.90, 125.68 (q, J = 3.8 Hz), 124.01 (q, J = 272.2 Hz), 123.05, 121.12 (dd, J = 12.7, 4.0 Hz), 112.10 (dd, J = 21.4, 3.5 Hz), 104.67 (t, J = 25.8 Hz), 18.10. | $C_{20}H_{15}F_5NO_2$ 396.10175 | 396.09787 |

TABLE 2-continued

Physical Properties of Synthesized Compounds

| Compound No. | NMR[1] | Formula[2] m/z (calc.) | m/z (meas.) |
|---|---|---|---|
| JN132 | $^1$H NMR δ 8.15 (br s, 1H), 7.86 (s, 1H), 7.53 (d, J = 8.2 Hz, 1H), 7.28-7.20 (m, 1H), 7.21-7.19 (m, 1H), 7.08-6.97 (m, 3H), 5.49-5.46 (m, 2H), 1.89 (dd, J = 1.6, 0.9 Hz, 3H). $^{13}$C NMR δ 166.09, 164.12 (dd, J = 254.6 11.5 Hz), 163.84, 160.25 (dd, J = 252.0, 12.0 Hz), 140.01, 139.60, 139.02, 132.98-132.60 (2C, m), 132.43, 130.78, 128.95 (q, J = 31.8 Hz), 127.81 (q, J = 5.2 Hz), 127.69, 122.55 (q, J = 273.4 Hz), 122.35, 117.52 (dd, J = 16.3, 4.1 Hz), 113.47 (dd, J = 21.5, 3.7 Hz), 105.81 (t, J = 25.3 Hz), 18.26. | $C_{20}H_{14}ClF_5NO_2$ 430.06277 | 430.05878 |
| JN133 | $^1$H NMR δ 7.50-7.42 (m, 2H), 7.21 (d, J = 1.6 Hz, 1H), 7.04-6.98 (m, 1H), 6.97-6.89 (m, 1H), 6.80 (ddd, J = 10.2, 8.7, 2.6 Hz, 1H), 6.69 (s, 1H), 4.15 (m, 1H), 3.37 (m, 1H), 1.45 (br s, 6H), 1.05 (br s, 6H). $^{13}$C NMR δ 169.00, 163.40 (dd, J = 251.8, 11.9 Hz), 159.04 (dd, J = 251.1, 11.8 Hz), 140.96, 135.54, 132.37 (d, J = 2.0 Hz), 131.96 (dd, J = 9.6, 4.7 Hz), 131.37, 128.27, 127.55 (q, J = 5.2 Hz), 127.44 (d, J = 31.0 Hz), 126.49, 122.82 (q, J = 272.8 Hz), 119.13 (dd, J = 15.2, 4.0 Hz), 112.53 (dd, J = 21.3, 3.5 Hz), 104.81 (t, J = 25.7 Hz), 50.80, 46.02, 20.48. | $C_{22}H_{22}ClF_5NO$ 446.13046 | 446.12989 |
| JN134 | $^1$H NMR (DMSO-$d_6$) δ 7.42 (s, 1H), 7.33 (br s, 1H), 7.28 (d, J = 8.6 Hz, 2H), 7.25-7.15 (m, 4H), 7.06 (br s, 1H), 7.00 (d, J = 8.6 Hz, 2H). $^{13}$C NMR (DMSO-$d_6$) δ 168.75, 161.78 (d, J = 244.4 Hz), 136.52, 133.92, 133.00, 132.80, 132.38 (d, J = 3.2 Hz), 131.54 (d, J = 8.3 Hz), 131.29, 128.35, 115.86 (d, J = 21.2 Hz). | $C_{15}H_{12}ClFNO$ 276.05860 | 276.05836 |
| JN135 | $^1$H NMR δ 8.08 (br s, 1H), 7.96 (s, 1H), 7.24 (d, J = 8.6 Hz, 2H), 7.04 (d, J = 8.5 Hz, 2H), 6.80 (dd, J = 8.6, 6.9 Hz, 2H), 5.54 (d, J = 1.0 Hz, 1H), 5.49 (q, J = 1.6 Hz, 1H), 1.95-1.90 (m, 3H); $^{13}$C NMR δ 166.84, 164.19, 163.82 (dt, J = 253.8, 15.0 Hz), 160.70 (ddd, J = 252.4, 14.7, 9.3 Hz), 143.98, 140.21, 136.40, 132.65, 130.68, 129.21, 122.12, 121.61, 108.31 (td, J = 21.0, 4.8 Hz), 101.71 (td, J = 25.9, 3.3 Hz), 18.36. | $C_{19}H_{14}ClF_3NO_2$ 380.06597 | 380.06580 |
| JN136 | $^1$H NMR δ 7.33-7.27 (m, 2H), 7.25-7.21 (m, 1H), 7.16 (d, J = 8.4 Hz, 2H), 7.14-7.11 (m, 2H), 6.97 (d, J = 8.4 Hz, 2H), 5.54 (br t, J = 5.9 Hz, 1H), 5.43 (m, 1H), 5.20 (m, 1H), 3.81 (ddd, J = 13.6, 7.0, 5.5 Hz, 1H), 3.34 (ddd, J = 13.5, 9.3, 4.9 Hz, 1H), 3.16-3.05 (m, 1H), 2.96 (dd, J = 13.8, 6.6 Hz, 1H), 2.89 (dd, J = 13.8, 8.4 Hz, 1H), 1.81 (dd, J = 1.6, 1.0 Hz, 3H); $^{13}$C NMR δ 168.41, 141.64, 140.09, 138.01, 132.04, 130.45, 128.92, 128.51, 127.93, 127.23, 119.43, 47.48, 44.54, 39.96, 18.62. | $C_{19}H_{21}ClNO$ 314.13062 | 314.12985 |
| JN137 | $^1$H NMR δ 7.49 (dd, J = 8.9, 5.2 Hz, 2H), 7.43-7.38 (m, 2H), 7.32 (d, J = 8.5 Hz, 2H), 7.08 (dd, J = 8.9, 8.4 Hz, 2H), 6.89 (s, 1H), 5.79 (d, J = 9.4 Hz, 1H), 5.41 (dq, J = 9.3, 5.9 Hz, 1H), 3.57-3.51 (m, 1H), 3.51-3.46 (m, 1H), 1.19 (d, J = 5.9 Hz, 3H), 1.14 (t, J = 7.0 Hz, 3H); $^{13}$C NMR δ 168.93, 163.06 (d, J = 248.9 Hz), 138.36, 134.44, 133.97, 132.98 (d, J = 3.3 Hz), 129.97, 128.92, 128.22 (d, J = 8.2 Hz), 127.66 (d, J = 1.7 Hz), 115.99 (d, J = 21.8 Hz), 76.98, 64.06, 21.60, 15.29. | [M − OEt]$^+$ $C_{17}H_{14}ClFNO$ 302.07425 | 302.07457 |

[1]Unless otherwise specified, the NMR data are given in chloroform-d at 500 MHz for $^1$H NMR, and at 126 MHz for $^{13}$C NMR.
[2]Unless otherwise specified, formula is for [M + H]$^+$ where M represents the compound in its charge neutral form.
[3]Not available. Molecule was unstable under the ionization conditions.

Example 3: Biological Assays Conducted on Exemplary Compounds

The inhibitory activity of JN018 was further evaluated in experiments in which the AR transactivation domain (TAD) or the c-Jun or CREB TAD was fused to the heterologous GAL4 DNA-binding domain and thereby drive reporter gene expression governed by the GAL4 response element (FIG. 1). JN018 selectively inhibits the AR-GAL4-DBD fusion protein, which indicates that JN018 targets AR activity through the AR TAD.

Figure 2:
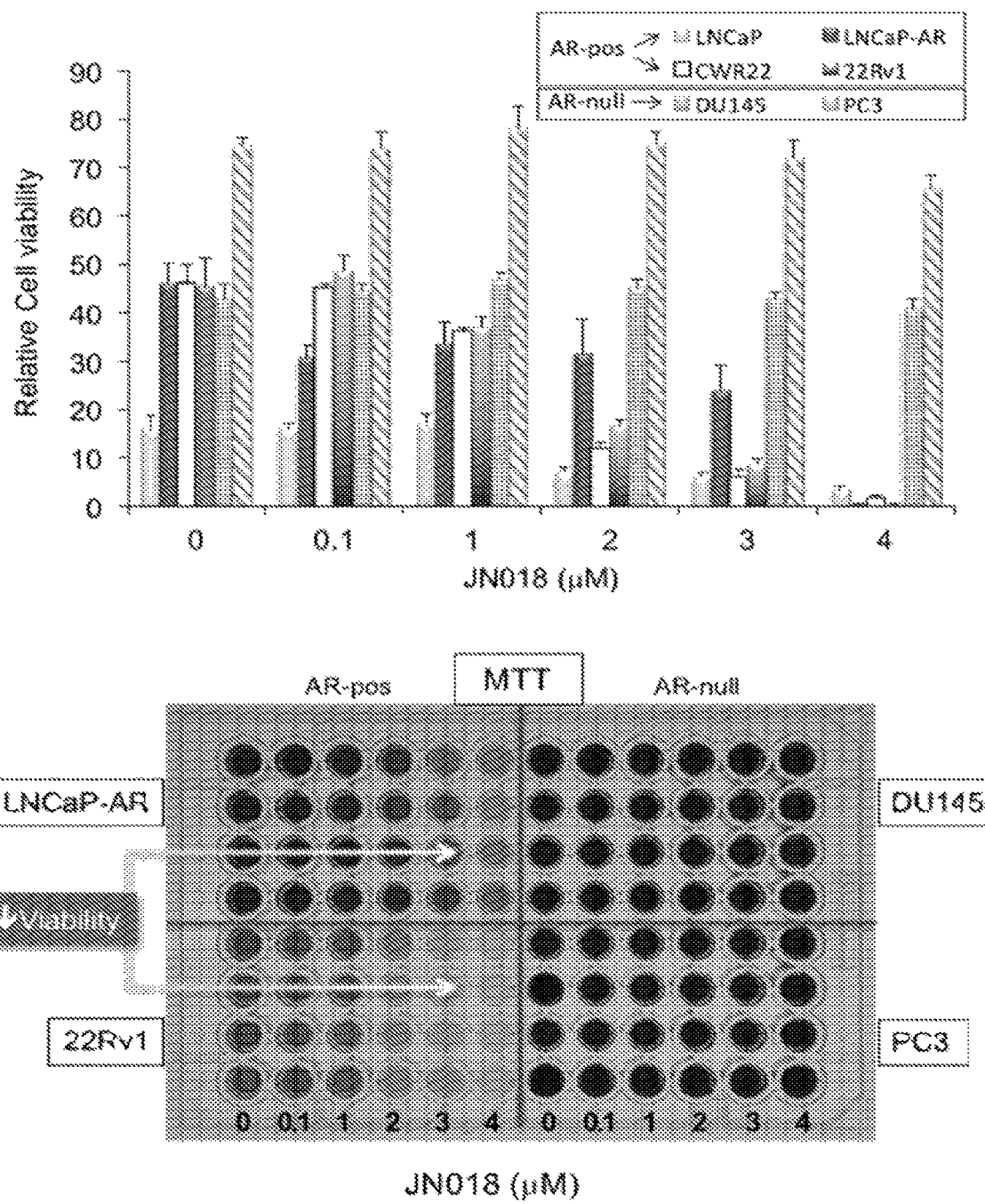
FIG. 2. shows the biologic activity of JN018 on AR positive (LNCaP, first column for each concentration; LNCaP-AR, second column; CWR22, third column; and 22Rv1, fourth column) and AR-null (DU145, fifth column; PC3, sixth column) PCa cells after a 5 day exposure. The results are means of quadruplicate expts±s.d. Top panel: CellTiter GLO luminescent bioassay (arbitrary units on vertical axis). Bottom panel: classical MTT assay ([blue/yellow]=[viable/non-viable]).

Next, the effects of the compounds on growth of prostate cancer cell lines in vitro were evaluated. JN018 inhibits the growth of AR expressing prostate cancer cells including those that express the AR splice variants, but not AR null cells (FIG. 2).

Similar assays were performed on the compounds prepared above, as well as enzalutamide (MVDV3100). The results are summarized in Table 3.

TABLE 3

Assay Results

| | MMTV | ARE | GRE | AR-TAD | JUN-TAD | CREB-TAD | CRE | AP1 | MTT AR-Pos | MTT AR-Neg |
|---|---|---|---|---|---|---|---|---|---|---|
| MDV3100 | HIGH | HIGH | LOW | LOW | LOW | LOW | | HIGH | HIGH | LOW |
| JN001 | LOW | | | | | | | | | |
| JN002 | LOW | | | | | | | | | |
| JN003 | HIGH | | LOW | HIGH | LOW | LOW | | | LOW | LOW |
| JN004 | LOW | | | | | | | | | |
| JN005 | MED | | | | | | | | | |
| JN006 | LOW | | | | | | | | | |
| JN007 | MED | | | | | | | | | |
| JN008 | LOW | | | | | | | | | |
| JN009 | LOW | | | | | | | | | |
| JN010 | LOW | | | | | | | | | |
| JN011 | MED | | | | | | | | | |
| JN012 | LOW | | | | | | | | | |
| JN013 | MED | | | | | | | | | |
| JN014 | MED | | | | | | | | | |
| JN015 | HIGH | MED | MED | HIGH | LOW | LOW | | | MED | MED |
| JN016 | HIGH | | | | | | | | | |
| JN017 | LOW | LOW | | HIGH | LOW | LOW | | | HIGH | MED |
| JN018 | HIGH | HIGH | LOW | HIGH | LOW | LOW | LOW | LOW | HIGH | LOW |
| JN019 | | | | | | | | | LOW | LOW |
| JN020 | LOW | | | | | | | | LOW | LOW |
| JN021 | LOW | | | | | | | | LOW | MED |
| JN022 | HIGH | LOW | | HIGH | HIGH | LOW | | | HIGH | HIGH |
| JN023 | LOW | | | | | | | | LOW | LOW |
| JN024 | HIGH | HIGH | | HIGH | HIGH | HIGH | | | HIGH | MED |
| JN025 | HIGH | HIGH | | | | | | | LOW | MED |
| JN026 | LOW | LOW | | | | | | | | |
| JN027 | MED | MED | | | | | | | MED | MED |
| JN028 | HIGH | HIGH | | | | | | | | |
| JN029 | HIGH | HIGH | | | | | | | | |
| JN030 | MED | MED | | | | | | | | |
| JN031 | LOW | LOW | | | | | | | | |
| JN032 | HIGH | | | | | | | | HIGH | LOW |
| JN033 | MED | | | | | | | | LOW | LOW |
| JN034 | MED | | | | | | | | MED | LOW |
| JNO35 | HIGH | | | | | | | | | |
| JN036 | HIGH | | | | | | | | MED/HIGH | LOW/MED |
| JN037 | MED | | | | | | | | | |
| JN038 | HIGH | | | | | | | | HIGH | MED |
| JN039 | | | | | | | | | | |
| JN040 | HIGH | | | | | | | | | |
| JN041 | HIGH | | | | | | | | | |
| JN042 | HIGH | | | | | | | | | |
| JN043 | HIGH | HIGH | HIGH | HIGH | LOW | MED | | | HIGH | MED |
| JN044 | MED | HIGH | HIGH | HIGH | LOW | MED | | | HIGH | MED |
| JN045 | HIGH | | | | | | | | | |
| JN046 | HIGH | | | | | | | | | |
| JN047 | HIGH | | | | | | | | | |
| JN048 | HIGH | HIGH | LOW | HIGH | LOW | LOW | | | HIGH | LOW |
| JN049 | HIGH | | | | | | | | | |
| JN050 | HIGH | HIGH | HIGH | HIGH | LOW | MED | | | HIGH | MED |
| JN051 | HIGH | HIGH | HIGH | | | | | | HIGH | HIGH |
| JN052 | MED | | | | | | | | LOW | MED |
| JN054 | MED | | | | | | | | LOW | HIGH |
| JN055 | MED | MED | HIGH | | | | | | | |
| JN056 | LOW | | | | | | | | | |
| JN057 | MED | | HIGH | | | | | | MED | MED |
| JN058 | LOW | | | | | | | | | |
| JN059 | | | | | | | | | | |
| JN060 | HIGH | HIGH | HIGH | | | | | | HIGH | HIGH |
| JN061 | LOW | | | | | | | | | |

TABLE 3-continued

Assay Results

| | MMTV | ARE | GRE | AR-TAD | JUN-TAD | CREB-TAD | CRE | AP1 | MTT AR-Pos | MTT AR-Neg |
|---|---|---|---|---|---|---|---|---|---|---|
| JN062 | LOW | | | | | | | | HIGH | HIGH |
| JN063 | MED | | | | | | | | | |
| JN065 | HIGH | | | | | | | | MED | LOW |
| JN066 | LOW | | | | | | | | | |
| JN067 | LOW | | | | | | | | | |
| JN068 | LOW | | | | | | | | | |
| JN069 | MED | | | | | | | | | |
| JN070 | MED | | | | | | | | | |
| JN071 | LOW | | | | | | | | | |
| JN072 | LOW | | | | | | | | | |
| JN073 | LOW | | | | | | | | | |
| JN074 | HIGH | | | | | | | | HIGH | HIGH |
| JN075 | MED | | | | | | | | HIGH | HIGH |
| JN076 | HIGH | | | | | | | | HIGH | MED |
| JN077 | HIGH | | | | | | | | LOW | LOW |
| JN078 | LOW | | | | | | | | | |
| JN079 | LOW | | | | | | | | | |
| JN080 | HIGH | | | | | | | | LOW | LOW |
| JN081 | MED | | | | | | | | | |
| JN082 | LOW | LOW | | | | | | | LOW | LOW |
| JN083 | HIGH | LOW | | | | | | | MED | MED |

Example 4: Further Evaluation of JN018

Figure 3:
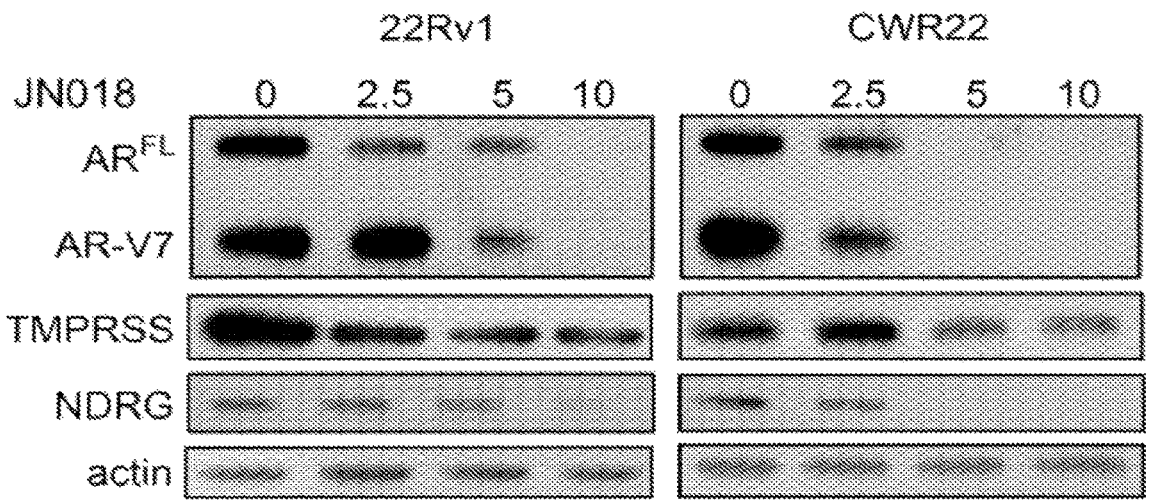
FIG. 3. shows Western blots demonstrating the effects of JN018 on expression of AR-regulated genes $AR^{FL}$, AR-V7, TMPRSS, and NDRG. 22Rv1 and CWR22 cells were exposed to JN018 at the indicated concentrations (in M) for 24 hours before protein extraction for Western blotting.

JN018 was further evaluated to identify a mechanism for its activity in prostate cancer cell lines. It was discovered that JN018 inhibits the expression of AR regulated genes. Specifically, JN018 reduces expression of TMPRSS and NDRG in a dose-dependent fashion (FIG. 3). Interestingly, JN018 also reduces both full length AR and AR-V7 expression. In principle, decreased AR expression can be attributed to several different effects, such as gene transcription, mRNA stability, translation, or protein stability.

Figure 4:
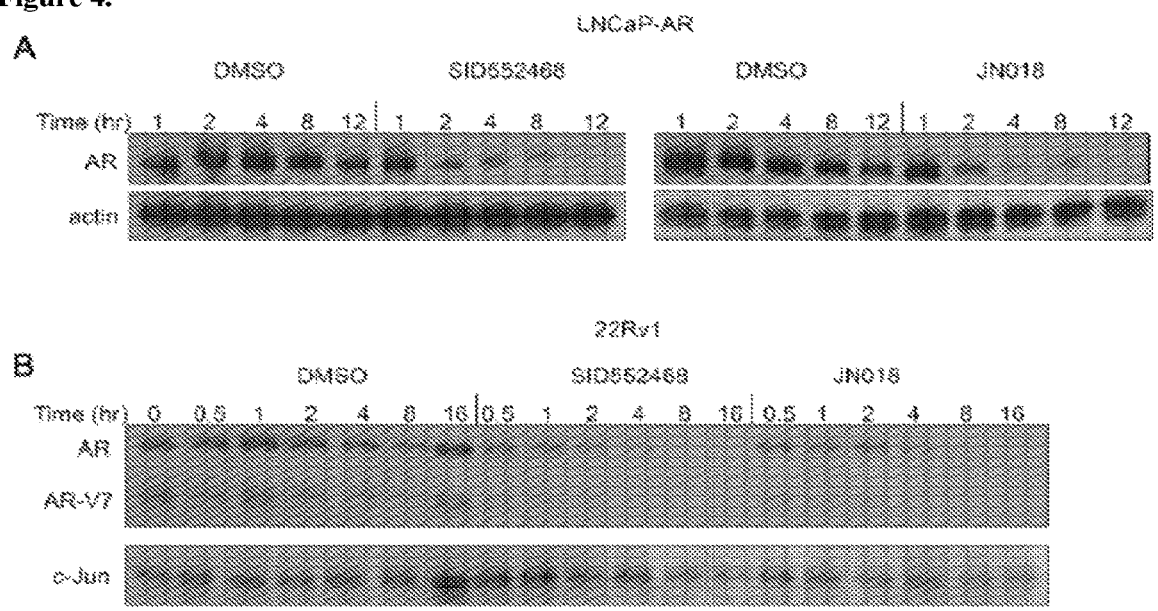
FIG. 4. shows Western blots demonstrating the effects of JN018 on AR/AR-V7 degradation. A) LNCaP-AR cells were exposed to the indicated compounds or vehicle (DMSO) in the presence of cycloheximide for the indicated times. Western blots were performed for the indicated proteins. B) Same as A but in 22Rv1 cells.

In protein stability experiments with cycloheximide to inhibit protein translation, JN018 reduced the half-life ($t_{1/2}$) of full length AR in LNCaP-AR cells (FIG. 4A). Given that JN018 seems to function through the AR TAD (see FIG. 1), the impact of JN018 on full-length and splice variant AR was studied next. JN018 potently reduced the $t_{1/2}$ of both full length and splice variant AR (FIG. 4B). JN018 also enhanced degradation of an AR splice variant known as AR Δ567 that was stably introduced into PC3 cells, which lack endogenous AR expression. This indicates that the effect of JN018 on AR splice variant degradation does not require the presence of the full-length AR. Not only did JN018 induce degradation of the AR in a time-dependent fashion, but also in a dose-dependent fashion. JN018 did not affect the $t_{1/2}$ of c-Jun or actin (FIG. 4), nor that of the closely related glucocorticoid receptor. These results suggest that JN018 may be an effective therapy for heavily treated CRPC, in which expression of the constitutively active splice variant represents a mechanism of resistance to novel AR targeting agents such as enzalutamide and abiraterone acetate. Because JN018 targets the N-terminal domain of the AR, JN018 may demonstrate growth inhibitory effects in prostate cancer cells that exhibit resistance to AR targeting therapies in a mechanism that is independent of constitutively active splice variants. $IC_{50}$s and $K_D$s determined during these studies are listed in Table 4.

TABLE 4

Inhibition and Binding Parameters of JN018

| $IC_{50}$ for AR inhibition | $IC_{50}$ for Growth Inhibition | $K_D$ for AR Binding | $IC_{50}$ for AR Degradation |
|---|---|---|---|
| 0.11 µM | 1.5 µM | $7.3 \times 10^{-9}$ | ~2.0 µM |

Example 5: Further Evaluation of Additional Compounds

A number of variations on JN018 have been prepared and tested, as described herein, for example, a series of compounds was prepared the β-dialkylamino dienone $R_1$ (hereafter referred to as $R_1$) moiety has undergone SAR analysis. The first compound in this series is JN097; other analogues are denoted with numbers >097. Based on SAR analysis performed to date, $Ar_1$ and $Ar_2$ are critical to the specificity of JN018, whereas $R_1$ is hypothesized to function as the "warhead" that confers androgen receptor inhibitory activity.

Figure 7:
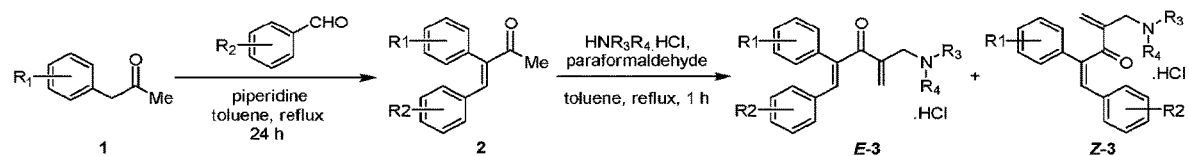
FIG. 7. Synthesis strategy of JN018 (yields; step 1=55%, step 2=62% (E), and 18% (Z)) and its analogues.
Figure 8:
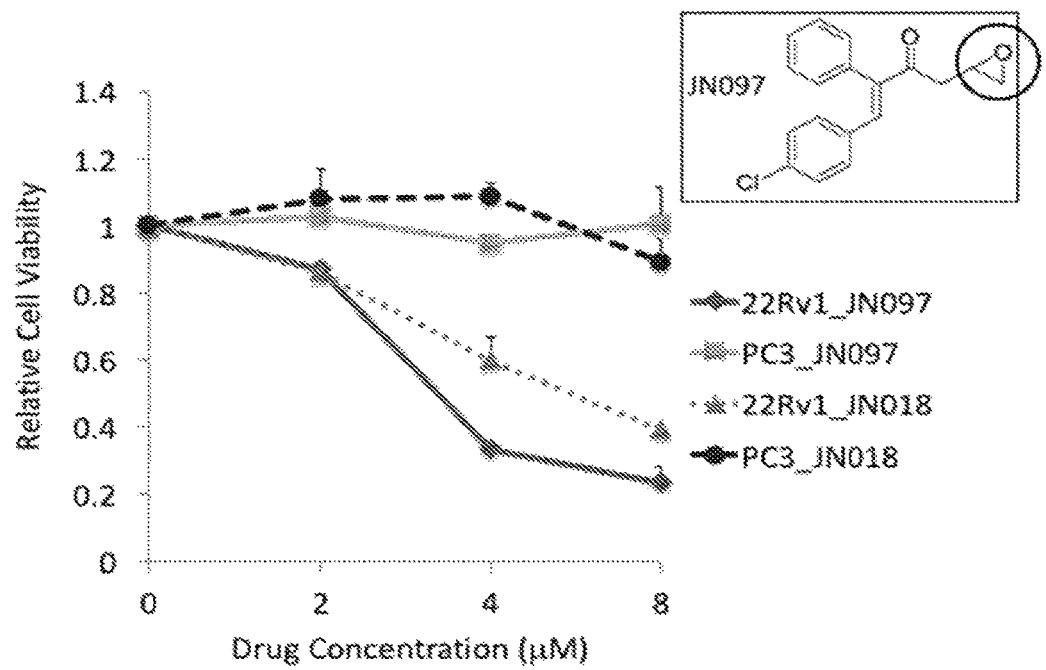
FIG. 8. JN097 exhibits improved performance characteristics of analogues of JN018. Cells were treated with JN018 or JN097 for 6 days and cell viability was measured by MTT assay. Circle highlights epoxide replacement of amine. Experiments were performed in quadruplicate; results are means+/−s.d. 22Rv1 are castration resistant and express $AR^{FL}$ and AR-V7, the most commonly detected $AR^{SV}$ in patient specimens. PC3 cells are also castration resistant and are AR null.

The synthetic approach to JN018 and its analogs is shown in FIG. 7. Phenylacetones are reacted with benzaldehydes to undergo Knoevenagel condensation, giving rise to (E)-3,4-diarylbut-3-en-2-ones of general structure 2. These methyl ketones are then reacted under Mannich reaction conditions to yield β-dialkylamino dienones 3 as a separable mixture of E (active) and Z (inactive) stereoisomers. In this series of compounds, substitutions have been made to the right-hand part of the molecule (i.e. $R_1$). JN097, in which an epoxide has replaced the β-dialkylamino enone, exhibits enhanced growth inhibitory effects as compared to JN018 (FIG. 8).

Figure 10A:
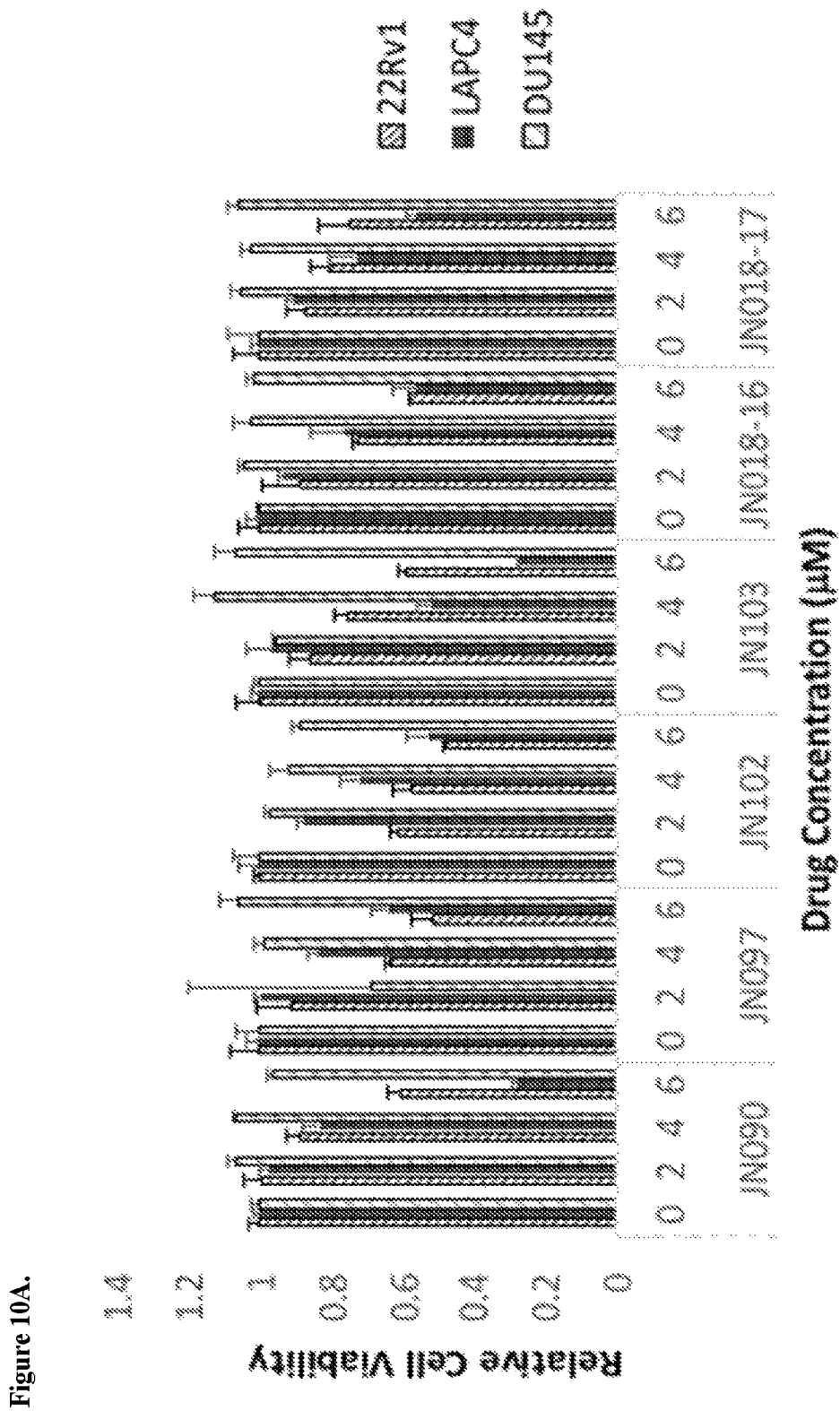
FIG. 10A. JN102 and 103 suppressed growth of AR expressing cells (LAPC4 and 22Rv1), but did not influence growth of AR null prostate cancers (DU145). For each compound and concentration in the figure, the bars represent relative cell viability of 22Rv1, LAPC4, and DU145, from left to right.
Figure 10B:
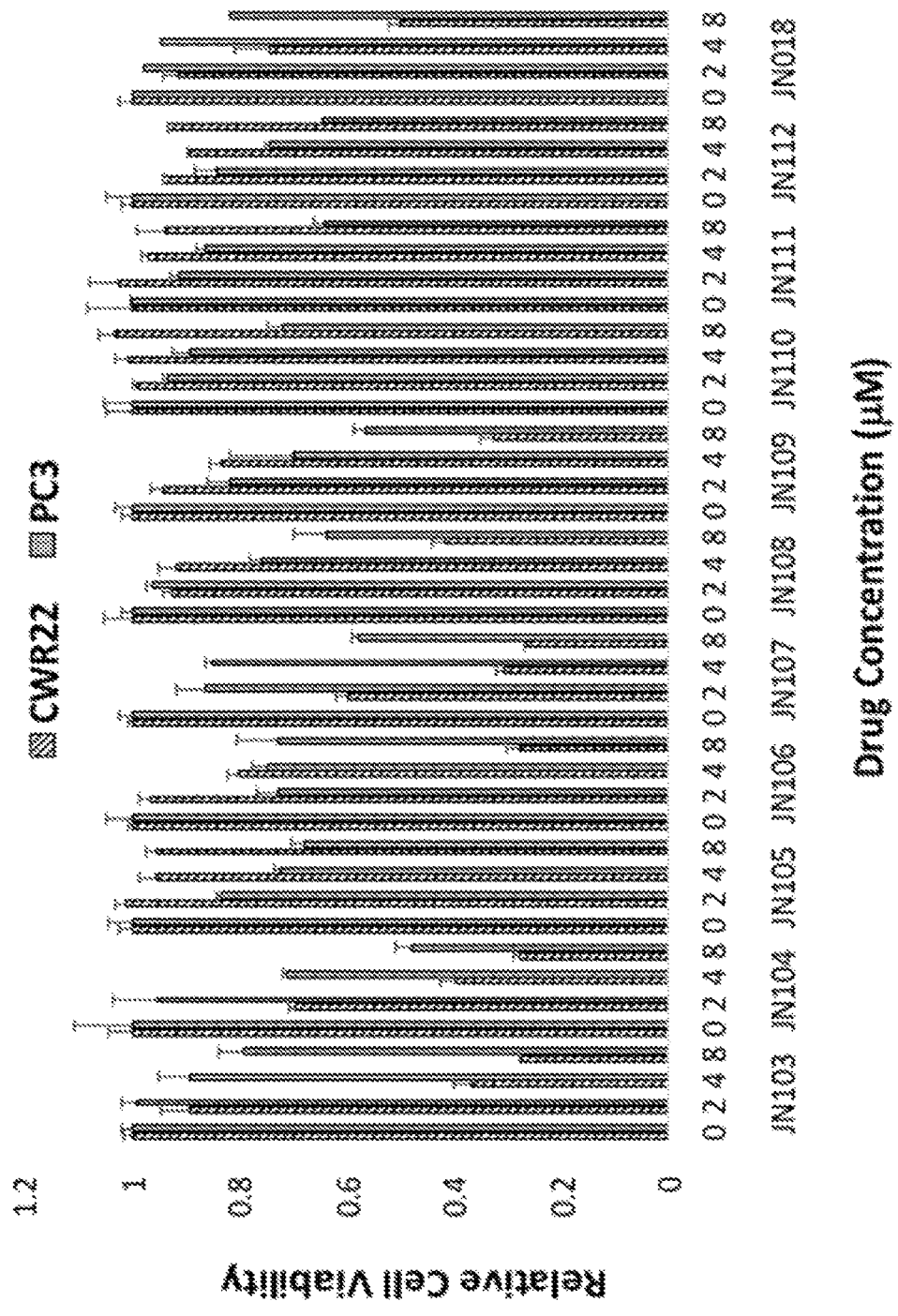
FIG. 10B. JN103 suppressed growth of AR expressing cells (CWR22), but did not influence growth of AR null prostate cancers (PC3). For each compound and concentration in the figure, the bars represent relative cell viability of CWR22 and PC3, from left to right.
Figure 11A:
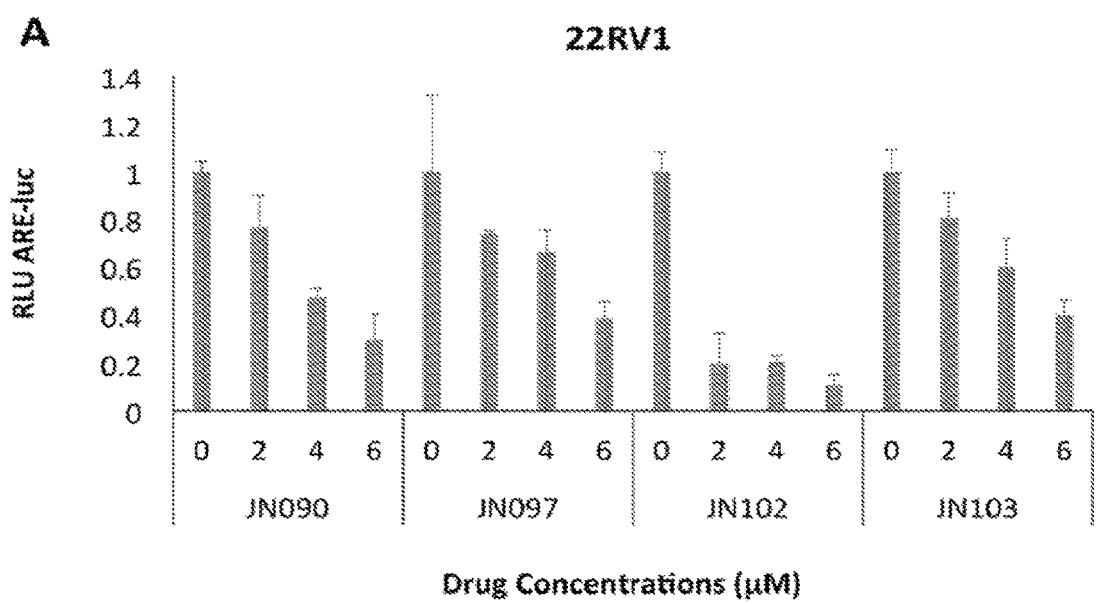
FIG. 11A. Effects of JN series compounds in reporter assays for androgen response element. Experiments were performed in triplicate and results are means+/−s.d.
Figure 11B:
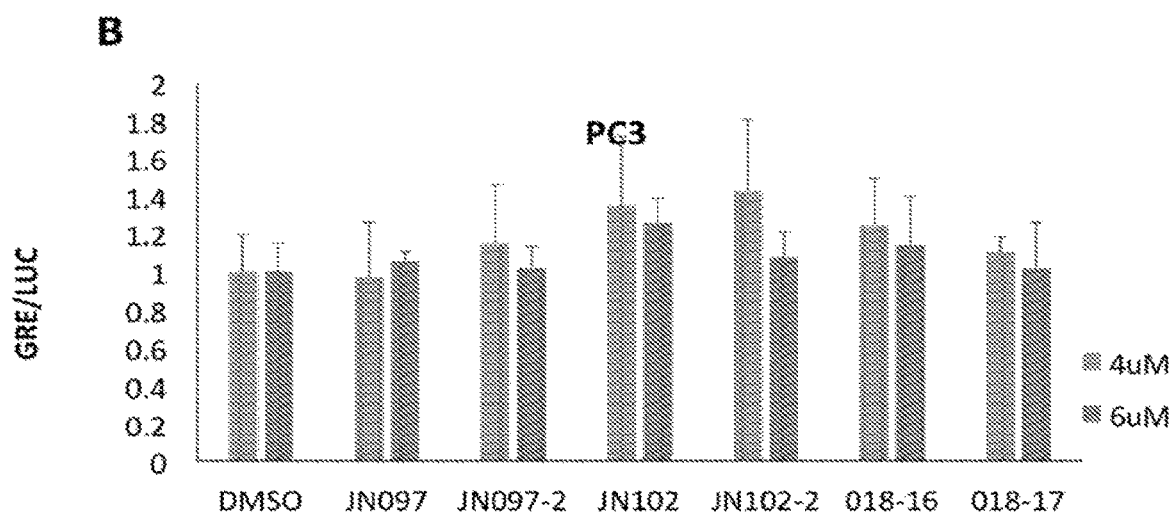
FIG. 11B. Effects of JN series compounds in reporter assays for glucocorticoid response element. Experiments were performed in triplicate and results are means+/−s.d. For each concentration in the figure, the bars represent the results of the reporter assay at a compound concentration of 4 M and 6 M, from left to right.

Further modifications of $R_1$ yielded compounds with a spectrum of growth suppressive effects. Of note, JN102 and JN103 exhibited improved growth suppressive effects, but JN104-112 did not (FIG. 10). JN102 and 103 suppressed growth of AR expressing cells (LAPC4, 22Rv1, CWR22, and LNCaP-AR), but did not influence growth of AR null prostate cancers (PC3 and DU145) or lung cancer cells (A549, not shown).

Figure 9A:
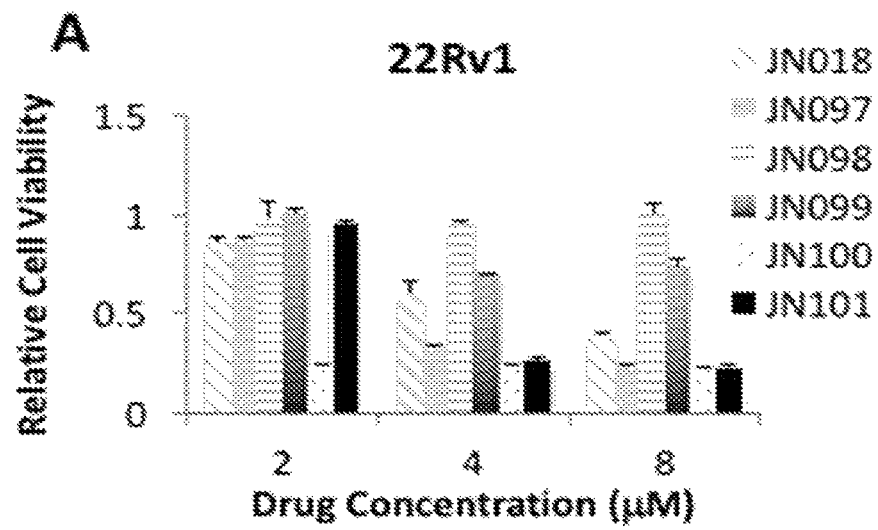
FIG. 9A. Growth inhibitory effects of JN97-101. 22Rv1 cells were exposed to the indicated compounds for 6 days; cell viability was measured by MTT assay. Results were normalized to that of vehicle control. Experiments were performed in quadruplicate; results are means+/−s.d. For each concentration in the figure, the bars represent relative cell viability for JN018, JN097, JN098, JN099, JN100, and JN101, from left to right.
Figure 9B:
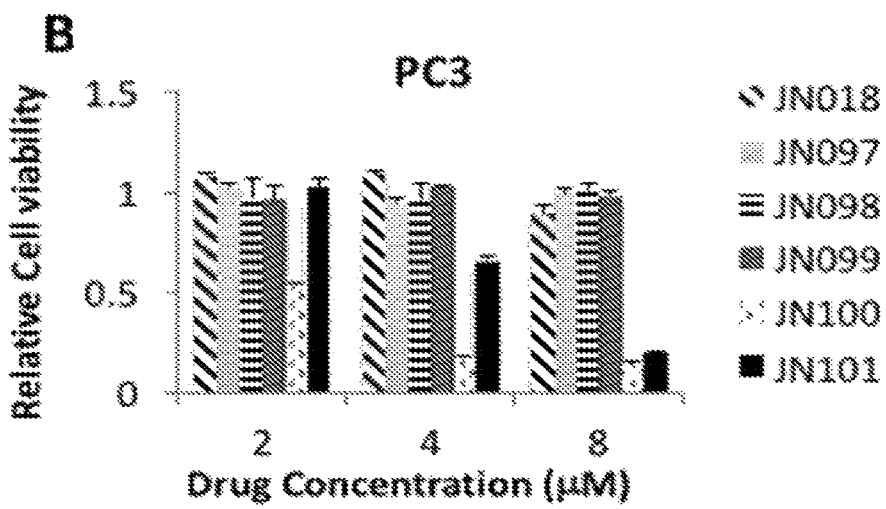
FIG. 9B. Growth inhibitory effects of JN97-101. AR null PC3 cells were exposed to the indicated compounds for 6 days; cell viability was measured by MTT assay. Results were normalized to that of vehicle control. Experiments were performed in quadruplicate; results are means+/−s.d. For each concentration in the figure, the bars represent relative cell viability for JN018, JN097, JN098, JN099, JN100, and JN101, from left to right.

JN097, 102 and 103 inhibited reporter activity driven by tandem copies of the androgen response element (ARE) but not the glucocorticoid response element (GRE) (FIG. 9). Analogous to JN018, JN097, 102, and 103 accelerated the degradation (i.e. shorten the half-life) of the AR (not shown).

Additional compounds have been generated with sequential numbering through JN136. In vitro biologic activity and biochemical activity/selectivity for AR inhibition have been tested for JN104-133. JN118 and 121 demonstrated improved in vitro growth inhibitory effects with reduced off target effects on AR-expressing and AR-null prostate cancer cell lines, respectively, compared to the parent compound JN018. JN128 has also shown selective growth inhibitory effects. In addition to the excellent growth inhibitory profile of JN118 and JN121, these two compounds also demonstrated excellent inhibitory effects on AR transcriptional activity in several reporter systems (MMTV reporter, ARE reporter, and PSA promoter/enhancer reporter) with minimal effects on non-AR-dependent reporter systems.

Figure 12A:
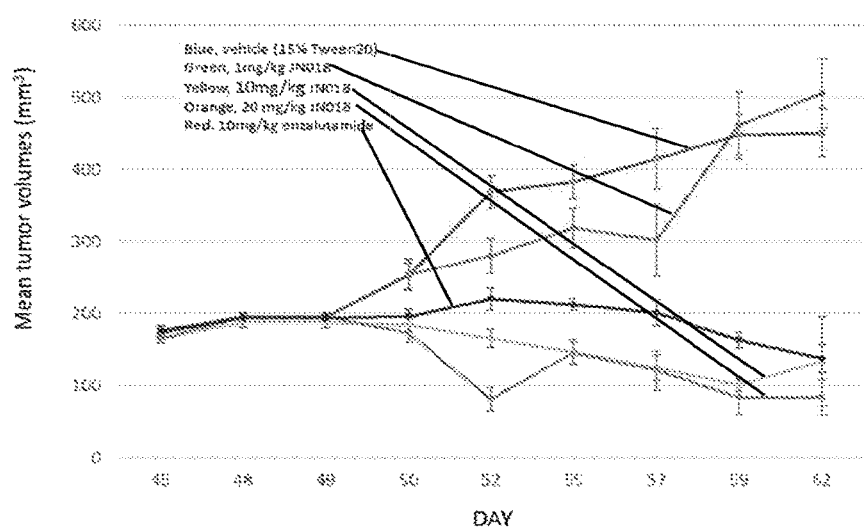
FIG. 12A. In vivo effects of JN series compounds. JN018 inhibits growth of LNCaP-AR model in castrated nude mice. Mice were administered JN018 at the indicated doses daily (M-F), vehicle or enzalutamide (MDV3100).

Selected compounds were tested in a mouse xenograft model. In this model, the LNCaP-AR castration resistant cell line was grown subcutaneously in the flanks of castrated nude mice. When tumors reached 150-200 mm³, mice were administered selected JN series compounds, vehicle or positive control by oral gavage once per day for five days per week (Mon-Fri). JN018 exhibited similar activity as enzalutamide (FIG. 12A), although some mice exhibited signs of toxicity with increased duration of drug treatment. JN090, JN103, and JN121 were subsequently tested and demonstrated anti-tumor effects (FIG. 12B) with limited or no outward signs of toxicity (FIG. 12B).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention.

The invention claimed is:

1. A compound represented by formula VIIb or a pharmaceutically acceptable salt thereof:

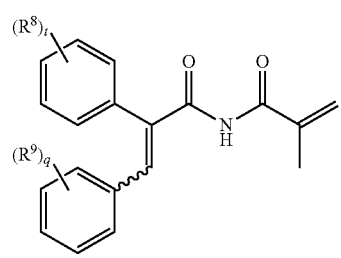

(VIIb)

wherein:
each $R^8$ is independently selected from halo, alkyl, or alkyloxy;
each $R^9$ is independently selected from halo, alkyl, or alkyloxy;
t is 1 or 2; and
q is 1 or 2.

2. The compound of claim 1, wherein each $R^8$ is independently fluoro or chloro.

3. The compound of claim 1, wherein each $R^9$ is independently fluoro or chloro.

4. The compound of claim 2, wherein t is 1.

5. The compound of claim 3, wherein q is 1.

6. The compound of claim 1 selected from:

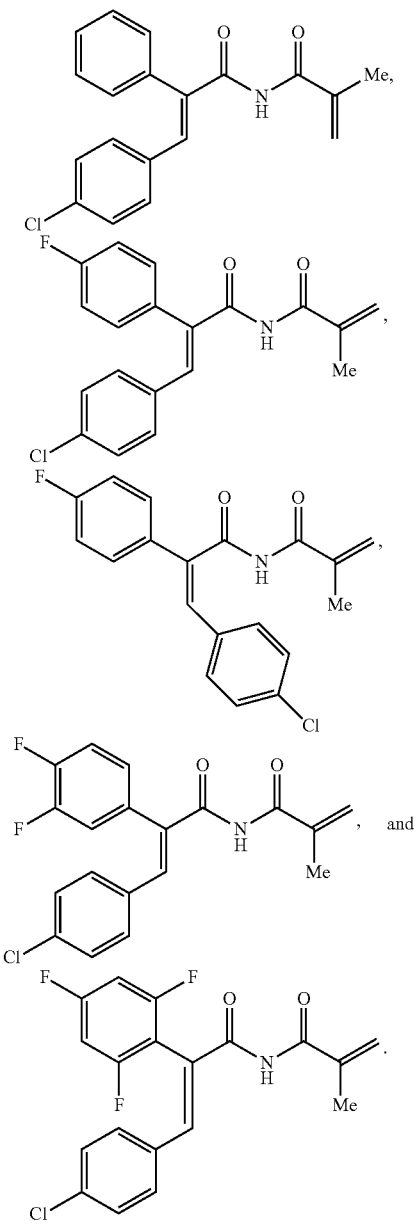

7. A pharmaceutical composition comprising the compound of claim 1 and a pharmaceutically acceptable excipient.

8. A method of inhibiting an androgen receptor, comprising contacting the androgen receptor with a compound of claim 1 or composition of claim 7.

9. A method of inducing degradation of an androgen receptor, comprising contacting the androgen receptor with a compound of claim 1 or composition of claim 7.

10. A method of treating a mammal suffering from prostate cancer, comprising administering a compound of claim 1 or composition of claim 7.

11. The method of claim 10, wherein the prostate cancer is castration-resistant prostate cancer.

12. The compound of claim 1, selected from

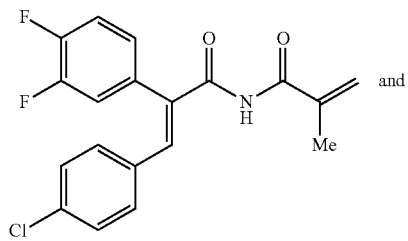 and

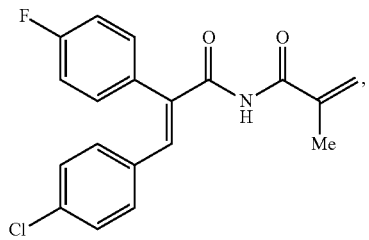

or a pharmaceutically acceptable salt thereof.

13. The compound of claim 12, wherein the compound is

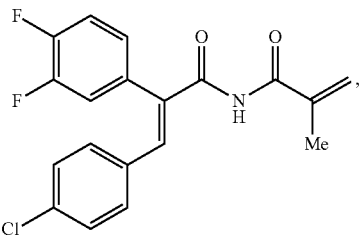 [SMILES: C=C(C)C(=O)NC(=O)/C(=C/c1ccc(Cl)cc1)c1ccc(F)c(F)c1]

or a pharmaceutically acceptable salt thereof.

14. The compound of claim 12, wherein the compound is

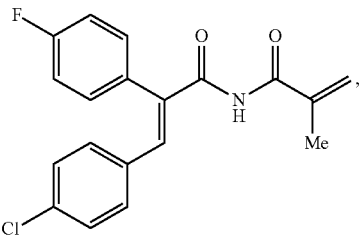 [SMILES: C=C(C)C(=O)NC(=O)/C(=C/c1ccc(Cl)cc1)c1ccc(F)cc1]

or a pharmaceutically acceptable salt thereof.

15. The compound of claim 1, wherein the compound is

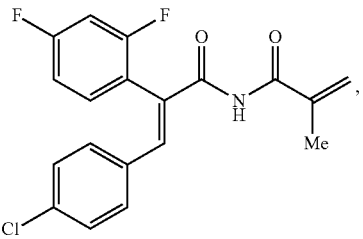 [SMILES: C=C(C)C(=O)NC(=O)/C(=C/c1ccc(Cl)cc1)c1ccc(F)cc1F]

or a pharmaceutically acceptable salt thereof.

\* \* \* \* \*

UNITED STATES PATENT AND TRADEMARK OFFICE
CERTIFICATE OF CORRECTION

PATENT NO. : 12,162,818 B2
APPLICATION NO. : 17/575027
DATED : December 10, 2024
INVENTOR(S) : Matthew Rettig et al.

It is certified that error appears in the above-identified patent and that said Letters Patent is hereby corrected as shown below:

In the Claims

Column 122

In Claim 6, Line 20, cancel the following structure: 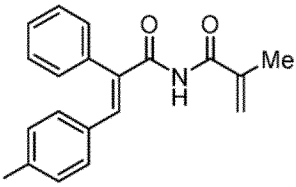 . In Claim 6, Line 40, insert the following structure: -- 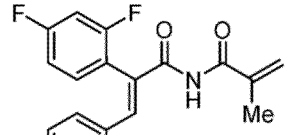 --.

Signed and Sealed this
Eighteenth Day of March, 2025

Coke Morgan Stewart
*Acting Director of the United States Patent and Trademark Office*